(12) United States Patent
Mookhtiar et al.

(10) Patent No.: US 8,940,900 B2
(45) Date of Patent: *Jan. 27, 2015

(54) 2,2,2-TRI-SUBSTITUTED ACETAMIDE DERIVATIVES AS GLUCOKINASE ACTIVATORS, THEIR PROCESS AND PHARMACEUTICAL APPLICATION

(75) Inventors: Kasim A. Mookhtiar, Maharashtra (IN); Debnath Bhuniya, Bangalore (IN); Bhavesh Dave, Bangalore (IN); Gobind S. Kapkoti, Bangalore (IN); Sujay Basu, Bangalore (IN); Anita Chugh, Bangalore (IN); Siddhartha De, Bangalore (IN); Venkata P. Palle, Bangalore (IN)

(73) Assignee: Advinus Therapeutics Private Limited, Bangalore, IN (US)

( * ) Notice: Subject to any disclaimer, the term of this patent is extended or adjusted under 35 U.S.C. 154(b) by 393 days.

This patent is subject to a terminal disclaimer.

(21) Appl. No.: 12/528,770

(22) PCT Filed: Feb. 25, 2008

(86) PCT No.: PCT/IN2008/000109
§ 371 (c)(1),
(2), (4) Date: Jan. 29, 2010

(87) PCT Pub. No.: WO2008/104994
PCT Pub. Date: Sep. 4, 2008

(65) Prior Publication Data
US 2010/0144772 A1 Jun. 10, 2010

(30) Foreign Application Priority Data
Feb. 28, 2007 (IN) .............................. 409/CHE/2007

(51) Int. Cl.
| | | |
|---|---|---|
| C07D 417/12 | (2006.01) |
| C07D 277/82 | (2006.01) |
| C07D 277/44 | (2006.01) |
| A61K 31/44 | (2006.01) |
| A61K 31/425 | (2006.01) |
| C07D 277/46 | (2006.01) |
| C07D 213/40 | (2006.01) |
| C07D 213/75 | (2006.01) |
| C07D 213/76 | (2006.01) |
| C07D 213/80 | (2006.01) |
| C07D 213/82 | (2006.01) |
| C07D 239/42 | (2006.01) |
| C07D 257/06 | (2006.01) |
| C07D 261/14 | (2006.01) |
| C07D 285/135 | (2006.01) |

(52) U.S. Cl.
CPC ............ *C07D 277/46* (2013.01); *C07D 213/40* (2013.01); *C07D 213/75* (2013.01); *C07D 213/76* (2013.01); *C07D 213/80* (2013.01); *C07D 213/82* (2013.01); *C07D 239/42* (2013.01); *C07D 257/06* (2013.01); *C07D 261/14* (2013.01); *C07D 277/82* (2013.01); *C07D 285/135* (2013.01); *C07D 417/12* (2013.01)

USPC ..................... 546/270.7; 546/270.1; 548/159; 548/161; 548/171; 548/187; 548/195; 514/338; 514/342; 514/367; 514/371

(58) Field of Classification Search
None
See application file for complete search history.

(56) References Cited

U.S. PATENT DOCUMENTS

| | | |
|---|---|---|
| 3,776,917 A | 12/1973 | Mann et al. |
| 3,891,445 A * | 6/1975 | Arai et al. ..................... 430/552 |
| 4,146,631 A | 3/1979 | Ford et al. |
| 5,556,873 A * | 9/1996 | Huang et al. .................. 514/407 |
| 6,486,184 B2 | 11/2002 | Kester et al. |
| 7,034,049 B1 * | 4/2006 | Pevarello et al. ............. 514/404 |
| 2007/0270386 A1 | 11/2007 | Green et al. |

FOREIGN PATENT DOCUMENTS

| | | | |
|---|---|---|---|
| DE | 2924900 A1 * | 1/1981 |
| ES | 439155 A1 * | 7/1975 |
| GB | 1384684 A * | 2/1975 |
| JP | 55 064592 | 5/1980 |
| JP | 61126071 A * | 6/1986 |
| JP | 08 173525 | 7/1996 |

(Continued)

OTHER PUBLICATIONS

Stella, Valentino J, Expert Opinion of Therapeutic Patents, Prodrugs as therapeutics, 2004 14(3): 277-280.*

(Continued)

*Primary Examiner* — Nyeemah A Grazier
(74) *Attorney, Agent, or Firm* — Perkins Coie LLP

(57) ABSTRACT

Compounds of the present disclosure are 2,2,2-tri-substituted acetamide derivatives of formula (I), its polymorphs, stereoisomers, prodrugs, solvates, pharmaceutically acceptable salts and formulations thereof, useful as Glucokinase activator.

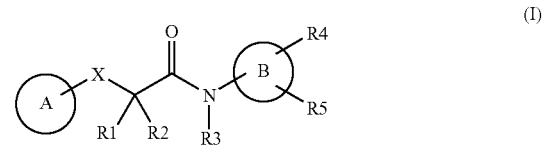

(I)

Processes of their preparation are also described in the disclosure. The disclosure also describes method to characterize partial glucokinase activators.

16 Claims, 4 Drawing Sheets

(56) References Cited

FOREIGN PATENT DOCUMENTS

| | | |
|---|---|---|
| JP | 2003-507329 | 2/2003 |
| JP | 2005-525291 | 8/2005 |
| JP | 2008-115149 | 5/2008 |
| JP | 2009-544755 | 12/2009 |
| WO | WO 9420467 A1 * | 9/1994 |
| WO | WO 00/58293 | 10/2000 |
| WO | 01/12189 | 2/2001 |
| WO | WO 01/19788 | 3/2001 |
| WO | WO 01/36415 | 5/2001 |
| WO | WO 01/44216 | 6/2001 |
| WO | WO 01/83465 | 11/2001 |
| WO | WO 01/85706 | 11/2001 |
| WO | WO 01/85707 | 11/2001 |
| WO | WO 02/08209 | 1/2002 |
| WO | WO 03/015774 | 2/2003 |
| WO | WO 03/055482 | 7/2003 |
| WO | WO 2004/000807 | 12/2003 |
| WO | WO 2004/002481 | 1/2004 |
| WO | WO 2004/014825 | 2/2004 |
| WO | WO 2004/063179 | 7/2004 |
| WO | WO 2005/027837 | 3/2005 |
| WO | 2005/033072 | 4/2005 |
| WO | WO 2005/123132 | 12/2005 |
| WO | WO 2006001750 A1 * | 1/2006 |
| WO | WO 2006/040528 | 4/2006 |
| WO | WO 2007089034 A1 * | 8/2007 |
| WO | WO 2007/102059 | 9/2007 |
| WO | WO 2008/014199 | 1/2008 |

OTHER PUBLICATIONS

Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Heilmann et al. Chemiker-Zeitung (1991), 115 (7-8), 219-221.*
Machon et al. Archivum Immunologiae et Therapiae Experimentalis (1981), 29(6), 813-821.*
Deng et al. Yaoxue Xuebao (1981), 16(1), 14-18.*
Sheehan et al. Journal of Organic Chemistry (1973), 38(5), 940-943.*
L. Agius, et al., Biochemical Journal, vol. 266(1), pp. 91-102 (1990).
A.V. Anisimov, et al., Russian J. Org. Chem., vol. 42(6), pp. 918-921 (2006).
T.C. Asthana, et al., Indian J. Chem., vol. 8(12), pp. 1086-1095 (1970).
G.J. Atwell, et al., J. Med. Chem., vol. 37(3), pp. 371-380 (1994).
K.J. Brocklehurst, et al., Diabetes, vol. 53, pp. 535-541 (2004).
Chemical Abstracts, No. 1981:30782 (1981).
Chemical Abstracts, No. 1971:110153n (vol. 74(21), May 24, 1971).
N. G. Clark, et al., Biochem. J., vol. 55, pp. 839-851 (1953).
Communication from the EPO Examining Division regarding corresponding national stage application EP 08738368.3 (Aug. 20, 2010).
A.M. Efanov, et al., Endocrinology, vol. 146, pp. 3696-3701 (2005).
S.A.M. El-Hawash, et al., Archives of Pharm. Chem. and Life Sci., vol. 339(8), pp. 437-447 (Aug. 1, 2006).
W.J. Evans, et al., J. Chem. Soc., pp. 329-331 (1936).
L. Field, et al., J. Am. Chem. Soc., vol. 78, pp. 4389-4394 (1956).
R. Ford, et al., J. Med. Chem., vol. 29(4), pp. 538-549 (1986).
M.C.T. Fyfe, Diabetologia, vol. 50, pp. 1277-1287 (2007).
B. Glaser, et al., N. Engl. J. Med., vol. 338, pp. 226-230 (1998).
A.L. Gloyn, Hum. Mutat., vol. 22, pp. 353-362 (2003).
A.L. Gloyn, et al., Diabetes, vol. 52, pp. 2433-2440 (2003).
J. Grimsby, et al., Science, vol. 301, pp. 370-373 (2003).
Grothe, Archiv. Pharmazie (Weinheim), vol. 238, pp. 600-614 (1908).
N. Hariharan, et al., Diabetes, vol. 46, pp. 11-16 (1997).
X. Huang, et al., Synthetic Communications, vol. 20(15), pp. 2291-2295 (1990).
B. Iddon, et al., J. Chem .Soc. Perkin Trans. I, pp. 1370-1380 (1980).
International Search Report for corresponding PCT application (PCT/IN2008/000109, published as WO 2008/104994 A3 on Apr. 2, 2009).
International Preliminary Report on Patentability for corresponding PCT application (PCT/IN2008/000109, Sep. 1, 2009).
T.L. Jetton, et al., J. Biol. Chem., vol. 269, pp. 3641-3654 (1994).
K. Kamata, et al., Structure, vol. 12, pp. 429-438 (2004).
E. Kolemainen, et al., Magnetic Resonance in Chem., vol. 38, pp. 384-385 (2000).
A.M. Mahmood, et al., J. Indian. Chem. Soc., vol. 59, pp. 675-677 (1982).
D. McKerrecher, et al., Bioorg. Med. Chem. Lett., vol. 15, pp. 2103-2106 (2005).
C. Postic, et al., J. Biol. Chem., vol. 274, pp. 305-315 (1999).
R.L. Printz & D.K. Granner, Endocrinology, vol. 146, pp. 3693-3695 (2005).
R. Sarabu, et al., Drug Discovery Today: Therapeutic Strategies, vol. 4(2), pp. 111-115 (Feb. 1, 2007).
H. Schaefer, et al., J. Praktische Chemie, vol. 321(4), pp. 695-698 (1979).
R.C. Tweit, et al., J. Med. Chem., vol. 16(10), pp. 1161-1169 (1973).
G. Yang, et al., Heteroatom Chem., vol. 12, pp. 491-496 (2001).
S.-Q. Zhang, et al., Synlett, vol. 5, pp. 590-596 (2001).
Communication Under Art. 94(3) EPC from the European Patent Office for European Application No. 08 738 368.3 dated Apr. 19, 2011.
Japanese Office Action for Japanese Application No. 2009-551312, dated Apr. 23, 2013.

* cited by examiner

2,2,2-TRI-SUBSTITUTED ACETAMIDE DERIVATIVES AS GLUCOKINASE ACTIVATORS, THEIR PROCESS AND PHARMACEUTICAL APPLICATION

FIELD OF THE INVENTION

This disclosure relates to a series of 2,2,2-tri-substituted acetamide derivatives, their polymorphs, stereoisomers, prodrugs, solvates, pharmaceutically acceptable salts and formulations thereof. The disclosure also relates to the process of preparation of 2,2,2-tri-substituted acetamide derivatives along with their glucokinase activating effects, which are beneficial for the prophylaxis, management, treatment, control of progression, or adjunct treatment of diseases and/or medical conditions where the activation of glucokinase would be beneficial, such as diabetes, dyslipidemia, metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

This disclosure further relates to a method of identifying compounds that are partial GK activators. It also relates to compounds with partial Glucokinase activities identified by the method, useful for the treatment of hyperglycemia, diabetes, obesity, dyslipidemia, metabolic syndrome and like, in mammals and have minimum hypoglycemic potential.

BACKGROUND OF THE INVENTION

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic elevation of blood glucose level leads to damage of blood vessels. In diabetes, the resultant problems are grouped under "microvascular disease" (due to damage to small blood vessels) and "macrovascular disease" (due to damage to the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Glucokinase (GK), also known as hexokinase IV or D, is one of four glucose-phosphorylating enzymes called hexokinases that catalyze the first step of glycolysis, the conversion of glucose to glucose 6-phosphate (G6P), in vertebrate tissues. GK functions in a dual role, with distinct functions in the pancreas and liver; (a) as a molecular glucose sensor in the insulin-producing pancreatic β-cells, and (b) as the high-capacity enzymatic step initiating the storage of glucose in the form of glycogen in the liver and uptake of glucose during hyperglycemia. Therefore, GK plays a central role in glucose homeostasis, through the phosphorylation of glucose in the liver, and the modulation of insulin secretion in the pancreas (Postic, C. et al (1999) *J. Biol. Chem.* 274: 305-315). GK also functions as a sensor in other neuroendocrine cells of the gastrointestinal tract and in various brain cells including specific cells in the hypothalamus (Jetton, T. A. et al (1994) *J. Biol. Chem.* 269: 3641-3654).

The physiological concentration of glucose in human plasma is approximately 5.5 mM under fasting conditions, and increases to about 12 mM in the fed state. This concentration is dependent on and maintained by the activity of GK, which senses glucose and controls metabolic flux in key cell types. The glucose concentration at which GK activity is at half of its maximal velocity or $V_{max}$ is defined as its $S_{0.5}$. The $S_{0.5}$ of GK for glucose lies in the middle of the physiological glucose concentration range at approximately 8 mM, allowing this enzyme to act as a molecular glucose sensor crucial for glucose homeostasis. The limited tissue distribution and unique kinetic properties of GK allow it to play a critical role in pancreatic β-cell insulin secretion and hepatic glucose utilization. GK differs from the other members of the mammalian hexokinase family in its unique sigmoidal kinetics with respect to glucose, a high $S_{0.5}$ that lies in the physiological glucose concentration range (the other three mammalian hexokinases have $S_{0.5}$ values less than 0.5 mM), the lack of product inhibition by G6P, and its tissue distribution in cell types that are thought to be responsive to changing plasma glucose levels.

Tissue-specific differences have been observed between the regulation of GK in the liver and the pancreas. In the liver, GK is allosterically inhibited by the glucokinase regulatory protein (GKRP), which results in its sequestration in the nucleus and subsequent protection from proteolytic degradation. This inhibition is reversed by high concentrations of glucose and by fructose 1-phosphate, and is potentiated by fructose 6-phosphate. In the pancreatic β-cells, GK expression is believed to be constitutive. GK is also known to be expressed in the hypothalamus, where it may exert effects on feeding behavior, and in the intestine, where it may contribute to the secretion of enteroincretins such as glucagon-like peptide-1 (GLP-1).

Given the role of GK as a molecular glucose sensor, it is not surprising that GK mutations have a profound influence on glucose homeostasis. About 2000 GK mutations that have been identified in humans result in impaired glucose-mediated insulin secretion and maturity-onset diabetes of the young type 2 (MODY-2). Some of these mutations result in decreased accumulation of hepatic glycogen, while others decrease GK activity by reducing the stability of the enzyme or by decreasing its V. Mutations that result in activation of GK are implicated in the onset of persistent hyperinsulinemic hypoglycemia of infancy (PHHI). Single point mutations (e.g. V62M, D158A, Y214A, V455M, and F456V) in regions distinct from the substrate binding site of the enzyme lead to modulation of GK activity (Glaser, B. et al (1998) *N. Engl. J. Med.* 338: 226-230; Gloyn, A. L. (2003) *Hum. Mutat.* 22: 353-362; Gloyn, A. L. et al (2003) *Diabetes* 52: 2433-2440). These observations highlight that GK activity can be regulated through allosteric modulation.

Homozygous knock out of GK in mice results in severe diabetes and death, while heterozygous disruption results in a milder diabetic phenotype, decreased hepatic glucose uptake and impaired insulin secretion in response to glucose. Conversely, overexpression of GK in fat-induced diabetic as well as non-diabetic mice results in improved glucose tolerance. Transgenic mice overexpressing GK in the liver show a modest (20%) increase in fasting GK activity, which correlates with lower fasting plasma glucose and insulin, and improved glucose tolerance (Hariharan, N. et al (1997) *Diabetes* 46: 11-16).

The enzymatic properties of GK can be described in terms of its velocity (i.e. its rate of converting glucose to G6P) and its $S_{0.5}$ for glucose (i.e. the apparent glucose concentration at which GK converts glucose to G6P at half of its maximal velocity). The $S_{0.5}$ of human GK for glucose is approximately 8 mM in enzyme based assay. GKAs induce increased conversion by GK of glucose to G6P by either decreasing the $S_{0.5}$ of GK for glucose, increasing its $V_{max}$, or by a combination of both, and can potentially lower blood glucose concentrations to hypoglycemic levels.

Several patent applications and publications describe the discovery of small-molecule glucokinase activators (GKAs) that allosterically modulate the activity of GK (Kamata, K. et al (2004) *Structure* 12: 429-438; WO 2003/055482 A1; WO 2005/123132 A2; WO 2004/002481 A2; U.S. Pat. No. 6,486, 184 B2; WO 2006/040528 A1; Fyfe, M. C. T. (2007) *Diabetologia,* 50: 1277-1287; McKerrecher, D. et al *Bioorg. Med. Chem. Lett.* 15 (2005) 2103-2106; Efanov, A. M. et al (2005) *Endocrinology* 146: 3696-3701; Printz, R. L. and Granner, D. K. (2005) *Endocrinology* 146: 3693-3695; Brockelhurst, K. J. et al (2004) *Diabetes,* 53: 535-541; Grimsby, J. et al (2003) *Science* 301: 370-373). These GKAs increase GK activity by decreasing its $S_{0.5}$ for glucose, and, in some cases, also increasing its $V_{max}$. However, for many of these compounds, hypoglycemia has been reported in animal studies which may be a consequence of excessive GK activation. For example, GK activators like Ro-28-1675 cause hypoglycemia in animal efficacy models (Kamata, K. et al (2004) *Structure* 12: 429-438). Similar hypoglycemic potential is seen in another GK activator, PSN-GK1, at higher dose (Fyfe, M. C. T. (2007) *Diabetologia,* 50: 1277-1287).

A concept of minimizing hypoglycemic potential by liver selective glucokinase activation has been mentioned in patent application WO 2005/123132. This concept relied on tissue specific role of glucokinase regulatory protein (GKRP) in liver which is absent in pancreas. A series of small molecule glucokinase activators have also been described as liver selective activators of glucokinase in patent application WO 2004/002481, and these molecules will have less hypoglycemic potential. However, there is no biological data disclosed in this application to support this hypothesis.

The present disclosure provides a novel class of compounds characterized as glucokinase activators and their potential use as medicament for the prophylactic or therapeutic treatment of hyperglycemia, diabetes, obesity, dyslipidemia, metabolic syndrome and like.

This present disclosure also provides a method of identifying compounds that are partial GK activators. Such partial GK activators identified using the said method will be useful for the treatment of hyperglycemia, diabetes, obesity, dyslipidemia, metabolic syndrome and like, in mammals and have minimum hypoglycemic potential.

SUMMARY OF THE INVENTION

The present disclosure provides a series of 2,2,2-tri-substituted acetamide derivatives of Formula (I), its polymorphs, stereoisomers, prodrugs, solvates or pharmaceutically acceptable salts thereof as Glucokinase Activators (GKAs);

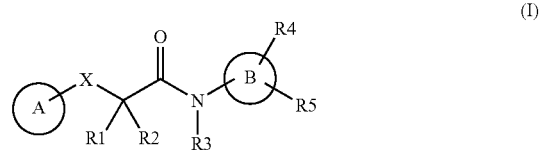

(I)

wherein,
Ring-A is selected from a group consisting of aryl, heteroaryl, heterocyclyl, cycloalkyl, wherein said group is optionally either partially or fully saturated; ring A is further substituted with 0 to 4 numbers of substitutions independently selected from a group consisting of alkyl, alkenyl, alkynyl, halo, mono, di or per haloalkyl, nitrile, nitro, oxo, —NR$^6$R$^7$, —OR$^6$, —SR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —(CR$^8$R$^9$)$_n$(CO)OR$^6$, —(CR$^8$R$^9$)$_n$C(O)R$^6$, —S(O)$_p$(NR$^6$)R$^7$, cycloalkyl, cycloalkylalkyl, heterocyclyl, heterocycloalkyl, aryl, arylalkyl, heteroaryl, heteroarylalkyl and like; which are further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR$^6$, —C(O)NR$^6$R$^7$, —OR$^6$, —SR$^6$ or —NR$^6$R$^7$ p=0-2; n=0-4;

R$^6$ and R$^7$ are independently selected from a group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, which are further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR$^6$, —C(O)NR$^6$R$^7$, —OR$^6$, —SR$^6$ or —NR$^6$R$^7$;

R$^8$ and R$^9$ are independently selected from a group consisting of hydrogen, fluorine, OR$^6$, alkyl and perfluoroalkyl;

X is selected from a group consisting of O, NR$^6$ and S(O)$_p$; wherein

R$^6$ is as described in the text;
p=0-2;
with a proviso that, it is not connected to another heteroatom from ring-A;

R$^1$ and R$^2$ are independently selected from a group consisting of fluoro, alkyl, alkenyl, alkynyl, aryl, aralkyl, heteroaryl, heteroarylalkyl, heterocyclyl, heterocyclylalkyl, cycloalkyl and cycloalkylalkyl, or are combined together to form a 3-7 membered ring; R$^1$ and R$^2$ are substituted with 0-4 numbers of substituents such as halogens, nitrile, nitro, oxo, —NR$^6$R$^7$, —OR$^6$, —SR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$; —(CR$^8$R$^9$)$_n$(CO)OR$^6$, —(CR$^8$R$^9$)$_n$(CO)NR$^6$R$^7$, —(CR$^8$R$^9$)$_n$S(O)$_p$NR$^6$R$^7$, —(CR$^8$R$^9$)$_n$NC(O)R$^6$, —(CR$^8$R$^9$)$_n$OR$^6$, —(CR$^8$R$^9$)$_n$NR$^6$R$^7$, —(CR$^8$R$^9$)$_n$C(O)R$^6$, S(O)$_p$(N)R$^6$, tetrazole, tetrazolylalkyl and the like, which are further substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR$^6$, —C(O)NR$^6$R$^7$, —OR$^6$, —SR$^6$ or —NR$^6$R$^7$; with the proviso that R$^1$ and R$^2$ are not hydrogen; wherein, p could be 0-2; n=0-4;

R$^6$, R$^7$, R$^8$ and R$^9$ are as described in the text;

R$^3$ is selected from a group consisting of hydrogen, alkyl and perfluoroalkyl;

Ring-B is optionally substituted 4-10 membered mono or bicyclic moieties containing at least one nitrogen in the ring; with the proviso that the amide nitrogen of formula (I) is not connected through any heteroatom of ring-B;

R$^4$ and R$^5$ are independently selected from a group consisting of hydrogen, halogen, alkyl, alkenyl, alkynyl, cycloalkyl, cycloalkylalkyl, heterocyclyl, heterocycloalkyl, aryl, arylalyl, heteroaryl, heteroarylalkyl, tetrazole, tetrazolylalkyl, mono, di or tri substituted haloalkyl, nitrile, nitro, oxo, —NR$^6$, —NR$^6$R$^7$, —OR$^6$, —SR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —(CR$^8$R$^9$)$_n$(CO)OR$^6$, —(CR$^8$R$^9$)$_n$(CO)NR$^6$R$^7$, —(CR$^8$R$^9$)$_n$S(O)$_p$NR$^6$R$^7$, —(CR$^8$R$^9$)$_n$N(R$^6$)C(O) R$^6$, —(CR$^8$R$^9$)$_n$OR$^6$, C(R$^8$R$^9$)$_n$NR$^6$R$^7$ and C(R$^8$R$^9$)$_n$CO (R$^6$); which are further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR$^6$, —C(O)NR$^6$R$^7$, —OR$^6$, —SR$^6$ or —NR$^6$R$^7$;

wherein n=0-4;

R$^6$, R$^7$, R$^8$ and R$^9$ are as described in the text.

In addition to R$^4$ and R$^5$, ring-B can be further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR$^6$, —C(O)NR$^6$R$^7$, —OR$^6$, —SR$^6$ or —NR$^6$R$^7$;

The disclosure also relates to the process of preparation of 2,2,2-tri-substituted acetamide derivatives of formula (I).

These GKAs are beneficial for the prophylaxis, management, treatment, control of progression, or adjunct treatment of diseases and/or medical conditions where the activation of glucokinase would be beneficial, such as diabetes, obesity, dyslipidemia, metabolic syndrome and/or diabetes-related complications including retinopathy, nephropathy, neuropathy, ischemic heart disease, arteriosclerosis, β-cell dysfunction, and as therapeutic and/or prophylactic agents for obesity.

The present disclosure also provides a method of identifying compounds capable of providing partial glucokinase (GK) activity for treating hyperglycemia with minimum hypoglycemic potential. Desirable compounds have glucokinase activation in a dose dependent manner while not affecting much glucokinase activation below a threshold glucose level.

The present disclosure also provides a method of minimizing hypoglycemic potential through optimal activation of GK by allosteric GKAs that, at saturating GKA concentrations, will result in a shift in the $S_{0.5}$ of GK for glucose between 20% and 90%, The maximal efficacy of such optimal GKAs at their saturating concentrations will result in a drop in the $S_{0.5}$ of GK for glucose to levels that will not lead to hypoglycemia. In other words, such optimal GKAs, at saturating concentrations, will ensure GK activation when dosed at hyperglycemic levels, but exhibit minimal or no GK activation at normoglycemic levels.

These and other features, aspects, and advantages of the present subject matter will become better understood with reference to the following description and appended claims. This Summary is provided to introduce a selection of concepts in a simplified form. This Summary is not intended to identify key features or essential features of the claimed subject matter, nor is it intended to be used to limit the scope of the claimed subject matter.

DEFINITIONS

In the structural formulas given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "mono or bicyclic moieties" refers to a carbocycle, an aryl, a heterocycle or a heteroaryl which can be aromatic or non-aromatic, saturated or unsaturated, 3 to 18 membered ring system including 0 to 5 heteroatoms independently selected from S, N, O; the said rings can be optionally substituted with common substituents.

The term "aryl", alone or in combination with any other term, refers to a monocyclic or a polycyclic aromatic ring system containing carbon-ring atoms, such as phenyl, biphenyl, naphthyl or anthryl which optionally carries one or more substituents, preferably one to three, each independently selected from halogen, trifluoromethyl, trifluoromethoxy, amino, alkyl, alkenyl, alkynyl, alkoxy, alkylcarbonyl, alkoxycarbamoyl, aminocarbonyl, cycloalkyl, cycloalkenyl, acyl, cyano, carbamoyl, alkoxycarbamoyl, methylendioxy, carboxy, alkoxycarbonyl, aminocarbonyl, aryloxy, alkylaminocarbonyl, dialkylaminocarbonyl, hydroxy, heteroaryl, heterocyclyl, keto, nitro, SO$_2$alkyl and the like. Preferred aryls are phenyl and naphthyl.

"Heteroaryl", alone or in combination with any other term, refers to a monocyclic aromatic ring structure containing 5 or 6 ring atoms, or a bicyclic aromatic group having 8 to 10 atoms, containing one or more, preferably 1 to 4, more preferably 1 to 3, even more preferably 1 to 2, heteroatoms independently selected from O, S, and N, and optionally substituted with 1 to 3 groups or substituents such as halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. "Heteroaryl" is also intended to include oxidized S or N, such as sulfinyl, sulfonyl and N-oxide of tertiary ring nitrogen. A carbon or hetero-atom is the point of attachment of the heteroaryl ring structure such that a stable aromatic ring is retained. Examples of heteroaryl groups are azepinyl, benzimidazolyl, benisoxazolyl, benzofurazanyl, benzopyranyl, benzothiazolyl, benzothienyl, benzoxazolyl, cinnolinyl, pyridinyl, pyridazinyl, pyrazinyl, quinazolinyl, purinyl, indolyl, quinolinyl, pyrimidinyl, pyrrolyl, oxazolyl, oxadiazolyl, thiazolyl, thienyl, isoxazolyl, oxathiadiazolyl, isothiazolyl, tetrazolyl, imidazolyl, triazinyl, furanyl, benzofuryl, and the like. A substituted heteroaryl contains a substituent attached at an available carbon or heteroatom to produce a stable compound. "Heteroaryl" is also intended to encompass compounds where a heteroaryl is attached to another non-aromatic aryl, cyclyl or heterocyclyl rings. Non-limiting examples include chromanyl, dihydrobenzofuranyl, indolinyl, dihydrobenzothienyl, benzodioxolyl dihydrobenzothienyl, dihydrobenzothiopyranyl, isochromanyl, dihydrobenzothiopyranyl sulfone, 1,3-dioxolanyl, benzofuryl, and the like.

As used herein, "heterocycle" or "heterocyclyl" refers to a stable 4 to 7-membered monocyclic or stable 8 to 11 membered bicyclic heterocyclic non-aromatic ring which is either saturated or unsaturated, and which consists of carbon atoms and from one to five heteroatoms selected from the group consisting of N, O, and S. The heterocyclic ring may be attached at any heteroatom or carbon atom which results in the creation of a stable structure. Non-limiting examples include imidazolidinyl, imidazolinyl, indolinyl, isoindolinyl, isoquinolinyl, isothiazolidinyl, isothiazolidinyl, morpholinyl, 2-oxopiperazinyl, 2-oxopiperidinyl, 2-oxopyrrolidinyl, piperidyl, piperazinyl, pyrazolidinyl, pyrrolidinyl, quinoxalinyl, tetrahydrofuryl, tetrahydroisoquinolinyl, tetrahydroquinolinyl, thiamorpholinyl sulfoxide, thiazolinyl, thiazolidine, isoxazoline, oxazolidin and dihydropyridyl.

"Alkyl" refers to straight or branched chain having 1 to 10 carbon atoms which is/are further substituted with one or more common substituents. Examples of alkyl groups include, but are not limited to methyl, ethyl, propyl, isopropyl, butyl, t-butyl and the like.

"Cycloalkyl" refers to a cyclic or polycyclic alkyl group containing 3 to 15 carbon atoms which are further substituted with one or more common substituents. Examples of cycloalkyl groups include, but are not limited to cyclopropyl, cyclobutyl, cyclopentyl, bicyclo[4.4.0]decane, adamantanyl, and the like. "Cycloalkyl" is also intended to encompass cyclic alkyl group attached to an aryl group such as 1,2,3,4-tetrahydronaphthalenyl, indanyl and the like.

"Alkenyl", alone or in combination refers to a straight, branched, mono cyclic or polycyclic unsaturated hydrocarbon preferably containing 2 to 10 carbon atoms, and having 1 to 5 double bonds and preferably 1 double bond. Examples of alkenyl groups include, but are not limited to are ethenyl, propenyl, isopropenyl, butenyl, bicycle[2.2.1]heptene and the like.

"Alkynyl", alone or in combination with any other term means a straight or branched hydrocarbon containing 2 to 10 carbon atoms containing 1 to 3 carbon to carbon triple bonds and at least one carbon to carbon triple bond. Examples of alkynyl groups include but are not limited to ethynyl, propynyl, butynyl and the like.

"Halo" or "Halogen", alone or in combination with any other term means halogens such as chloro (Cl), fluoro (F), bromo (Br) and iodo (I).

Common substitutions or substituents specifies the group such as halo, alkyl, alkenyl, alkynyl, cycloalkyl, aryl, heteroaryl, heterocycle, oxo, nitro, cyano, —COOR$^6$, —C(O)NR$^6$R$^7$, —OR$^6$, —S(O)$_p$R$^6$ and —NR$^6$R$^7$.

DESCRIPTION OF THE FIGURES

The above and other features, aspects, and advantages of the subject matter will become better understood with regard to the following description, appended claims, and accompanying drawings where:

DETAILED DESCRIPTION OF THE DISCLOSURE

Figure 1:
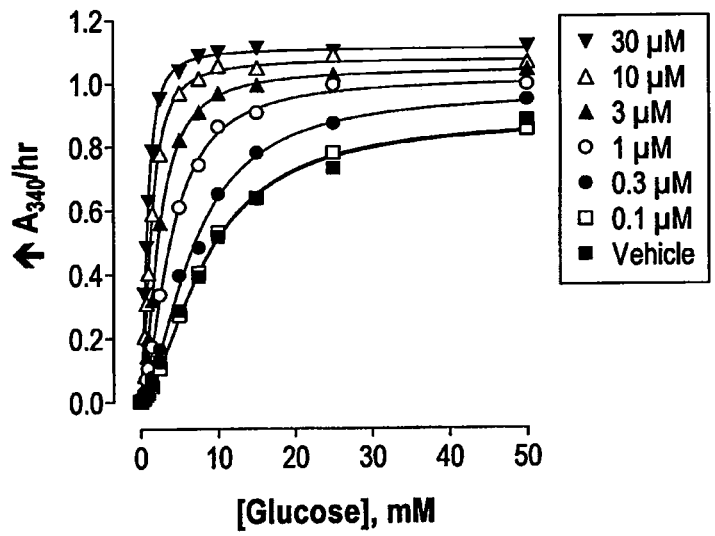
FIG. 1: Dose dependent glucokinase activation by Ro-28-1675 at various glucose concentrations. The activity of glucokinase (presented as the increase in NADH absorbance over time) is shown at different glucose concentrations in the presence of different concentrations of Ro-28-1675. The assay was done as described under "Measurement of glucokinase activity in enzyme-based assay" in the description of the current embodiment.

The present disclosure relates to 2,2,2-tri-substituted acetamide derivatives of formula (I), its polymorphs, stereoisomers, prodrugs, solvates or pharmaceutically acceptable salts thereof, useful as glucokinase activators. Formula (I) is described as

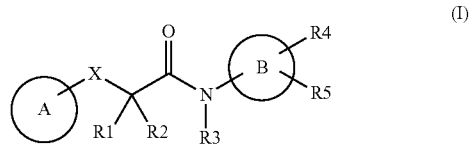

wherein;
Ring-A is selected from a group consisting of aryl, heteroaryl, heterocyclyl, cycloalkyl, wherein said group is optionally either partially or fully saturated;
wherein said ring A is further substituted with 0 to 4 numbers of substitutions independently selected from a group consisting of alkyl, alkenyl, alkynyl, halo, mono, di or per haloalkyl, nitrile, nitro, oxo, —$NR^6R^7$, —$OR^6$, —$SR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_n(CO)OR^6$, —$(CR^8R^9)_nC(O)R^6$, —$S(O)_p(NR^6)R^7$, cycloalkyl, cycloalkylalkyl, heterocyclyl, heterocycloalkyl, aryl, arylalkyl, heteroaryl, heteroarylalkyl groups and like; which further substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$; p=0-2; n=0-4;
$R^6$ and $R^7$ are independently selected from a group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, further substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$;
$R^8$ and $R^9$ are independently selected from a group consisting of hydrogen, fluorine, $OR^6$, alkyl, perfluoroalkyl;
X is selected from a group consisting of O, $NR^6$ and $S(O)_p$, wherein $R^6$ is as described above; p=0-2;
with a proviso that, X is not connected to another heteroatom from ring-A;
$R^1$ and $R^2$ are independently selected from a group consisting of fluoro, alkyl, alkenyl, alkynyl, aryl, aralkyl, heteroaryl, heteroarylalkyl, heterocyclyl, heterocyclylalkyl, cycloalkyl and cycloalkylalkyl, or are combined together to form a 3-7 membered ring;
wherein $R^1$ and $R^2$ are substituted with 0-4 numbers of substituents selected from halogen, nitrile, nitro, oxo, —$NR^6R^7$, —$OR^6$, —$SR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$; —$(CR^8R^9)_n(CO)OR^6$, —$(CR^8R^9)_n(CO)NR^6R^7$, —$(CR^8R^9)_nS(O)_pNR^6R^7$, —$(CR^8R^9)_nNC(O)R^6$, —$(CR^8R^9)_nOR^6$, —$(CR^8R^9)_nNR^6R^7$, —$(CR^8R^9)_nC(O)R^6$, $S(O)_p(N)R^6$, tetrazole and tetrazolylalkyl; which are further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$; with the proviso that $R^1$ and $R^2$ are not hydrogen;
$R^3$ is selected from hydrogen, alkyl and perfluoroalkyl;
Ring-B is selected from optionally substituted 4-10 membered mono or bicyclic moieties containing at least one nitrogen in the ring; with a proviso that the amide nitrogen of formula-(I) is not connected through any heteroatom of ring-B;
$R^4$ and $R^5$ are independently selected from a group consisting of hydrogen, halogen, alkyl, alkenyl, alkynyl, mono, di or tri substituted haloalkyl, nitrile, nitro, oxo, —$NR^6$, —$NR^6R^7$, —$OR^6$, —$SR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_n(CO)OR^6$, —$(CR^8R^9)_n(CO)NR^6R^7$, —$(CR^8R^9)_nS(O)_pNR^6R^7$, —$(CR^8R^9)_nN(R^6)C(O)R^6$, —$(CR^8R^9)_nOR^6$, $C(R^8R^9)_nNR^6R^7$, $C(R^8R^9)_nCO(R^6)$, cycloalkyl, cycloalkylalkyl, heterocyclyl, heterocycloalkyl, aryl, arylalyl, heteroaryl, heteroarylalkyl, tetrazole and tetrazolylalkyl which are further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$;
wherein
p=0-2; n=0-4;
R6, R7, R8 and R9 are as described above.

The present disclosure also relates to a compound of formula (I), or its polymorphs, stereoisomers, prodrug, solvate or a pharmaceutically acceptable salt thereof,
wherein ring-A is selected from

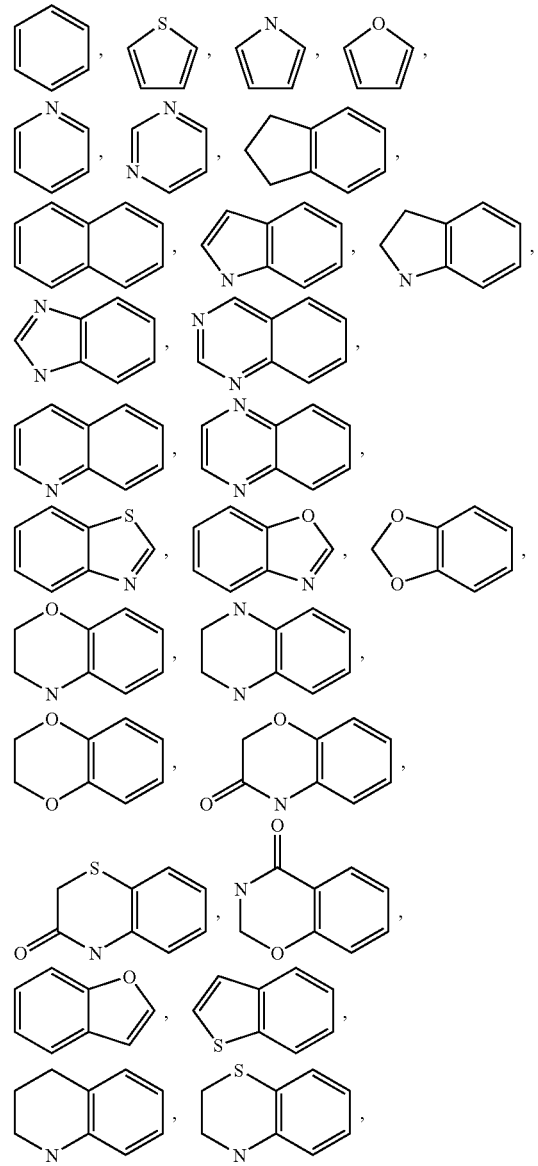

-continued

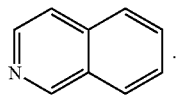

Another embodiment of the present disclosure is a compound of formula (I), or its polymorphs, stereoisomers, prodrug, solvate or a pharmaceutically acceptable salts thereof, wherein ring-B is selected from

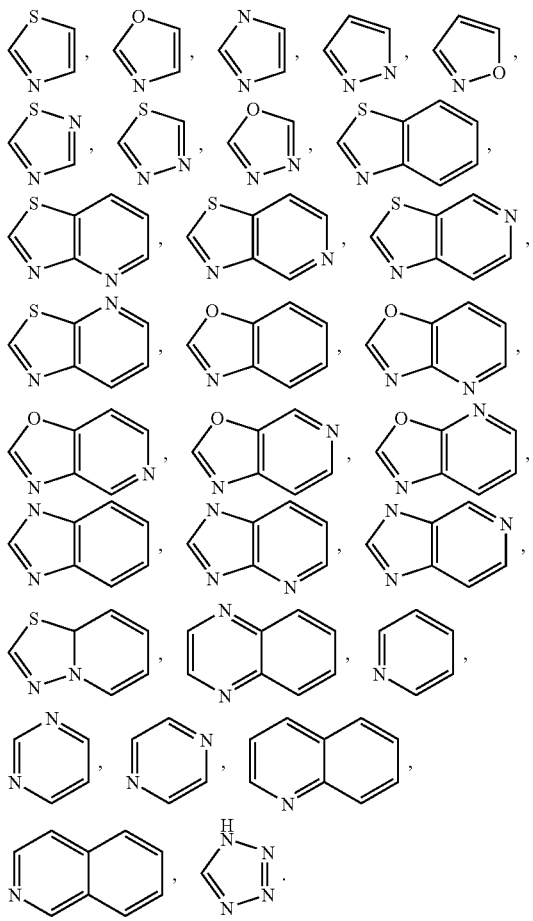

Yet another embodiment of the present disclosure is a compound of formula (I), or its polymorphs, stereoisomers, prodrug, solvate or a pharmaceutically acceptable salts thereof, wherein preferred ring-A is selected from

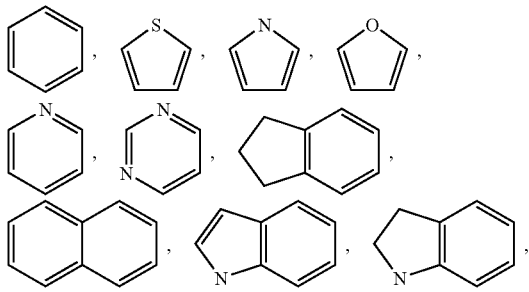

-continued

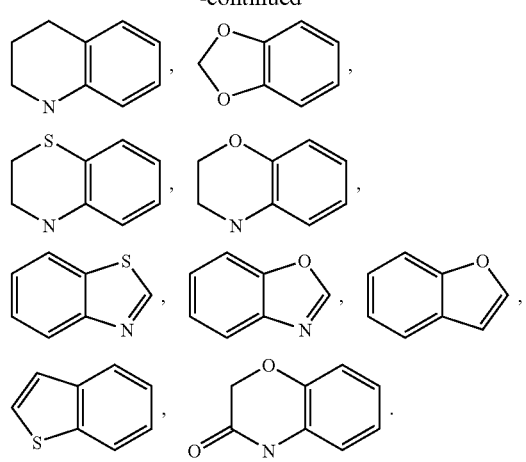

The present disclosure also relates to the process of preparation of compounds described in formula (I), polymorph, stereoisomer, prodrug, solvate or pharmaceutically acceptable salts thereof.

The compounds of formula (I), may be prepared as outlined in the Scheme 1-2 below:

Scheme 1:

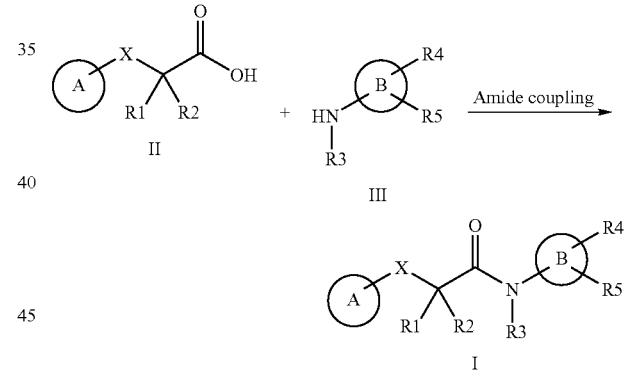

Scheme 2:

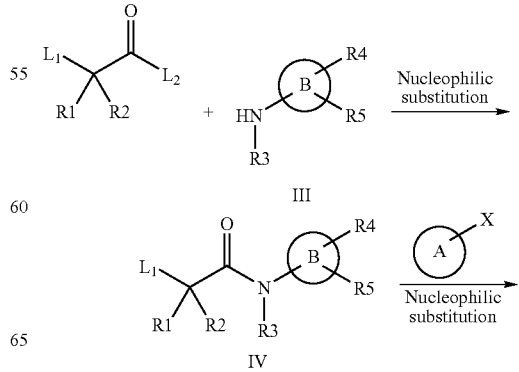

-continued

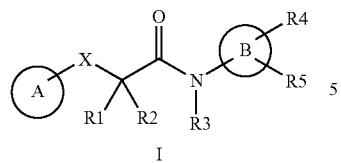

I

When ring-A, in Formula-I, is substituted with —[CH$_2$]$_n$—CO$_2$H group, the general synthesis can be as in scheme 3.

Scheme 3:

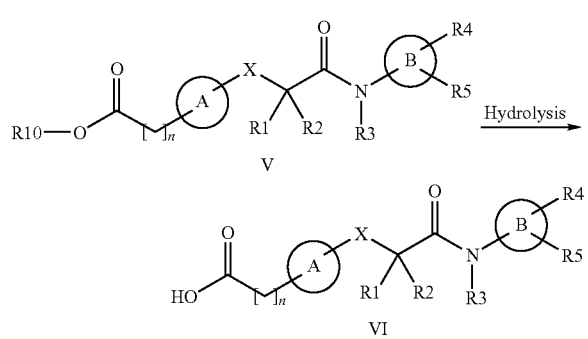

When R$^4$ or R$^5$ in ring-B of formula I is —(CR$^8$R$^9$)$_n$(CO)NR$^6$R$^7$, the synthesis can be as in scheme 4.

Scheme 4:

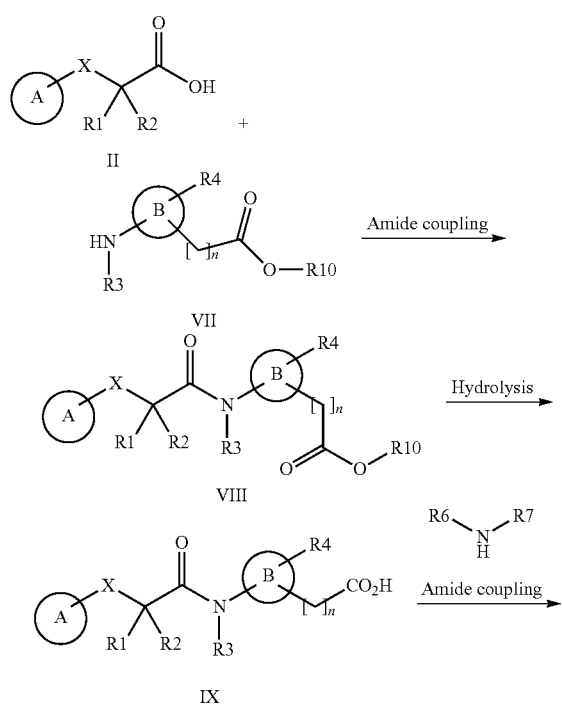

-continued

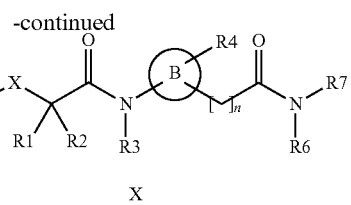

X

The intermediates covered by formula II can be prepared as outlined below in schemes 5-7.

Scheme 5: General route for synthesis of compounds of formula II

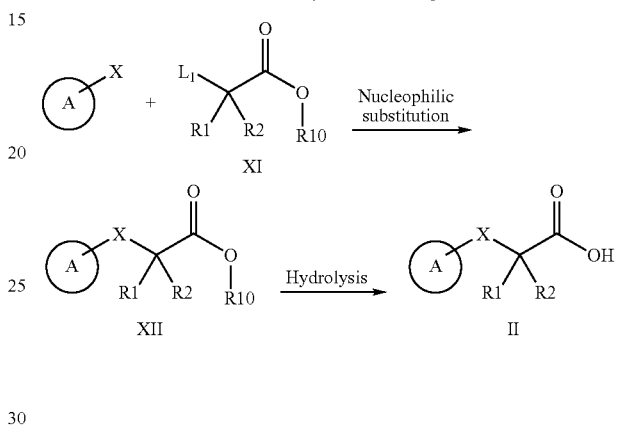

Scheme 6:

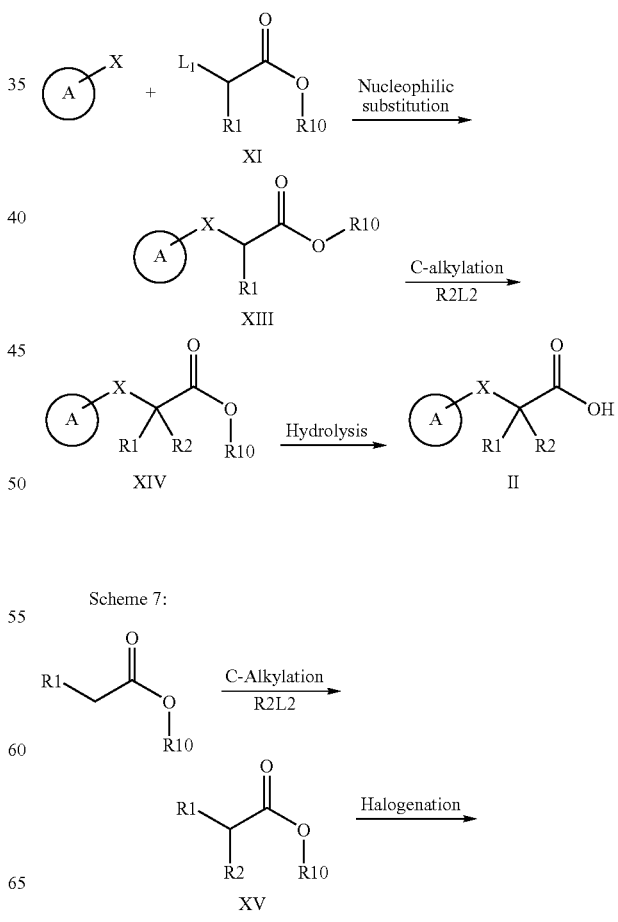

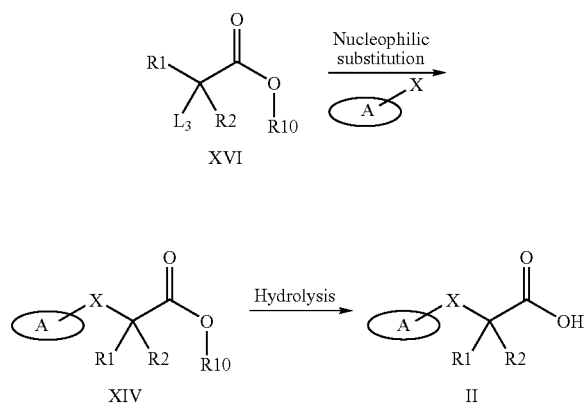

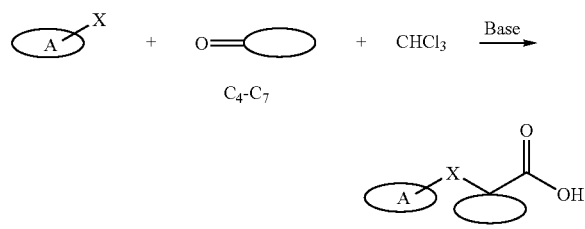

Scheme 8: General route for synthesis of compounds of formula II when $R^1$ and $R^2$ together form a C4-C7 cycloalkyl ring

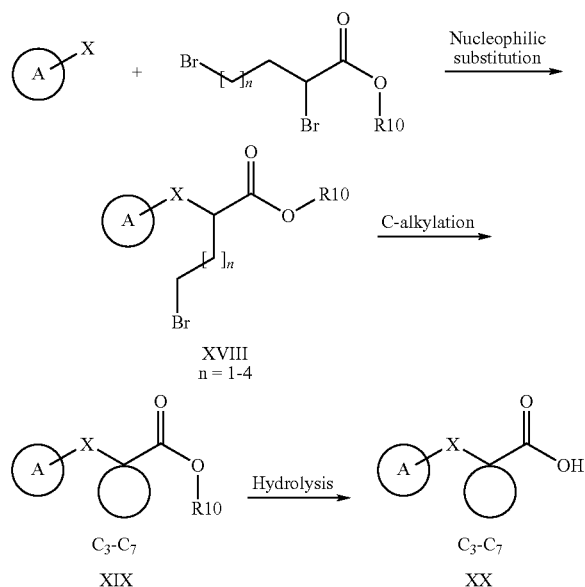

Scheme 9: General route for synthesis of compounds of formula II, when $R^1$ and $R^2$ together form a C3-C7 cycloalkyl ring.

Scheme 10: General route for synthesis of compounds of formula III when $R^4$ or $R^5$ is —[$CH_2$]n—$CH_2$—O—$R^{10}$

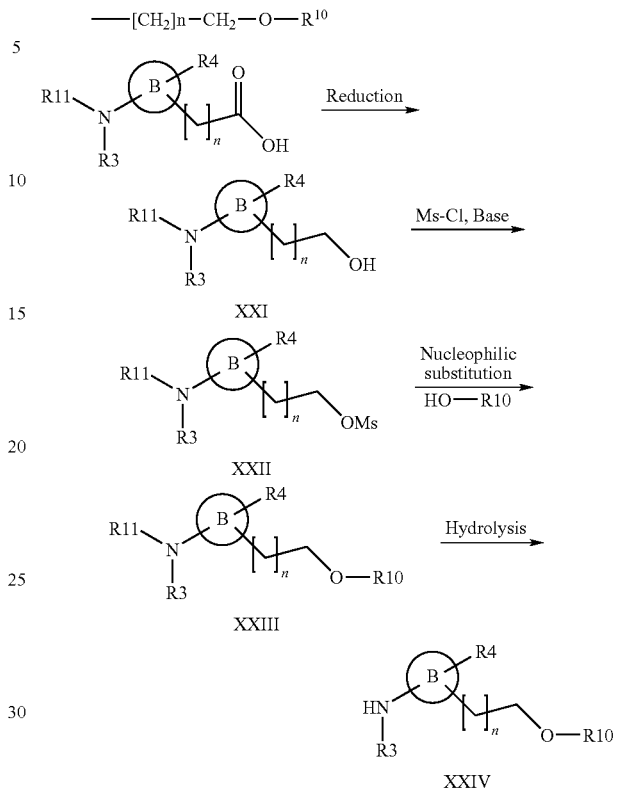

where $R^{10}$ is straight or branched chain lower alkyl, aryl and A, X, $R^1$, $R^2$, $R^3$, $R^4$, $R^5$, $R^6$, $R^7$, $R^8$ and $R^9$, unless defined, are as defined in the text;

$L_1$-$L_3$ are suitable leaving groups selected from chloro, bromo, iodo, methane sulfonyl and trifluoromethane sulfonyl.

Amide coupling has been carried out using any suitable amide coupling reagents like, oxallyl chloride, thionyl chloride, BOP-Cl, DCC, HOBt, EDCI, alkylchloroformate etc. may be used. Solvents like dichloromethane, dichloroethane, DMF, dimethylacetamide, THF, acetonitrile or mixture thereof. Organic non-nucleophilic bases such as triethyl amine, ethyldiisopropyl amine, pyridine, N-methylpyrrolidine, N,N-dimethylaminopyridine, DBU, DABCO, other hindered amines and pyridines may be used. The reaction is carried out at a temperature ranging from 5 to 150° C.

C-Alkylation has been carried out using strong bases selected from a group consisting of NaH, KH, LDA, NaHMDS, LiHMDS, KHMDS and like. Solvents are selected from a group consisting of THF, DMF, dimethylacetamide, diethyl ether, benzene, toluene and like. The reaction is carried out at a temperature ranging from 100 to 110° C.

Halogenation has been carried out using reagents selected from a group consisting of N-halosuccinimide and dihalogens, in presence of radical generating reagents like peroxides such as benzoylperoxide. Solvents used for this reaction include, but are not limited to, carbontetrachloride and ethers or mixtures thereof. The reaction is carried out at a temperature ranging from 5° C. to 60° C.

Nucleophilic substitution has been carried out using any suitable organic or inorganic bases. Organic bases are selected from a group consisting of mono, di or trialkyl amines particularly methylamine, ethylamine, dimethylamine, diethylamine and triethylamine. Inorganic bases are selected from a group consisting of alkali and alkaline earth metal hydrides, hydroxides, carbonates and bicarbonates or mixtures thereof. Solvents used for this reaction are selected from a group consisting of lower alcohols, acetone, acetonitrile, DMSO, DMF, dimethylacetamide, THF and toluene, or mixtures thereof. The reaction is carried out at a temperature ranging from 0° C. to 150° C.

The hydrolysis has been carried out using general saponification conditions employing inorganic bases selected from a group consisting of alkali and alkaline earth metal hydroxides, carbonates and bicarbonates, as for example lithium hydroxide, sodium hydride, sodium carbonate, potassium carbonate and cesium carbonate; solvents used for this reaction are selected from a group consisting of water, methanol, ethanol, THF and diethyl ether or mixtures thereof.

Reactions described in scheme 6 may be carried out at 20° C. to 60° C. using solvents like THF, ether, benzene and like. Bases may be alkali and alkaline earth metal hydroxides, carbonates and bicarbonates, such as potassium hydroxide, sodium hydroxide, sodium carbonate, potassium carbonate, cesium carbonate etc; or stronger bases like NaH, KH, LDA, NaHMDS, LiHMDS and KHMDS.

The present disclosure also relates to a method of identifying compounds that are partial GK activators useful for the treatment of hyperglycemia, diabetes, obesity, dyslipidemia, metabolic syndrome and like, at the same time will have minimum risk of hypoglycemic potential. The disclosure also provides partial GK activators and the method of treating hyperglycemia in mammals, especially in humans using the compounds identified by the above method.

The molecular mechanism behind GK activation and blood glucose lowering effect is two fold: (i) more insulin secretion from pancreas, and (ii) effective glycogen deposition in liver. However, excessive glucokinase activation is associated with hypoglycemic potential. Hence, partial GK activators, identified using the present method of the disclosure, will be useful for the treatment of hyperglycemia, diabetes, obesity, dyslipidemia, metabolic syndrome and like, at the same time will have minimum risk of hypoglycemic potential.

The enzymatic properties of glucokinase can be described in terms of its velocity (i.e. its rate of converting glucose to G6P) and its $S_{0.5}$ for glucose (i.e. the apparent glucose concentration at which GK converts glucose to G6P at half of its maximal velocity). The $S_{0.5}$ of glucose, in an in vitro assay using recombinant human GK, is approximately 8 mM. GK activators induce increased conversion of glucose to G6P by GK by decreasing the $S_{0.5}$ of GK for glucose.

Figure 2A:
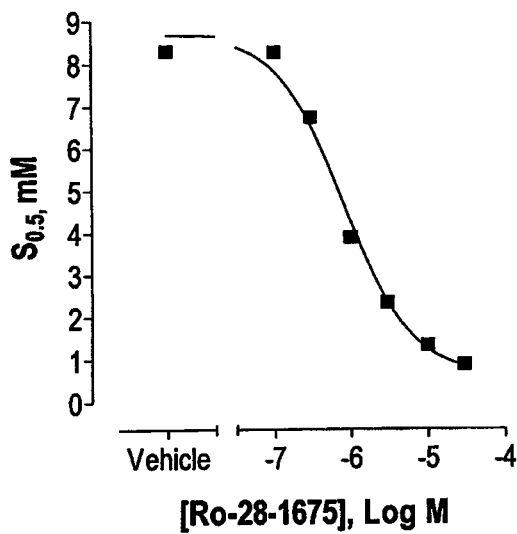
FIG. 2A: Dose dependent effect of Ro-28-1675 on $S_{0.5}$. The $S_{0.5}$ of glucokinase for glucose at each concentration of Ro-28-1675 is calculated from a modified version of the Michaelis-Menten equation, $V=V_{max} [S]^n/(S_{0.5}^n+[S]^n)$, where [S] is the glucose concentration and n is the Hill coefficient (taken as 1.7 to account for the sigmoidal kinetics of glucokinase with respect to glucose). The $S_{0.5}$ is plotted against the log of the Ro-28-1675 concentration.
Figure 2B:
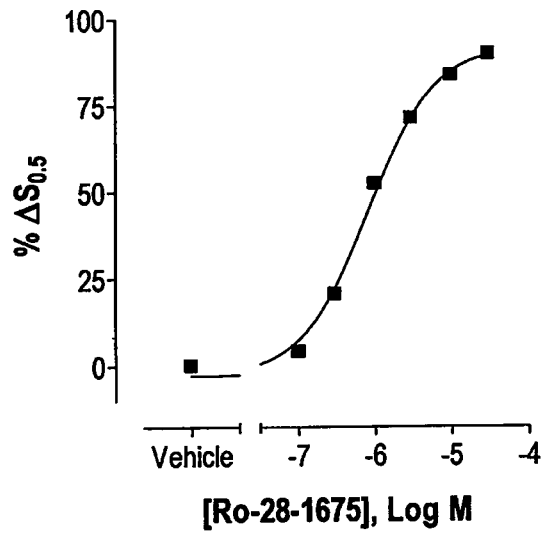
FIG. 2B: Dose dependent effect of Ro-28-1675 on % $\Delta S_{0.5}$. The change in the $S_{0.5}$ of glucokinase ($\Delta S_{0.5}$) for glucose is calculated by subtracting the $S_{0.5}$ at each concentration of Ro-28-1675 from the $S_{0.5}$ in the vehicle control. The $\Delta S_{0.5}$ is then normalized to a percent scale, where the $S_{0.5}$ in the vehicle control is set to 0% and 0 mM glucose is set to 100%. The % $\Delta S_{0.5}$ is then plotted against the log of the Ro-28-1675 concentration. The $EC_{50}$ of % change in $S_{0.5}$ is obtained from the sigmoidal fit of the data.
Figure 3:
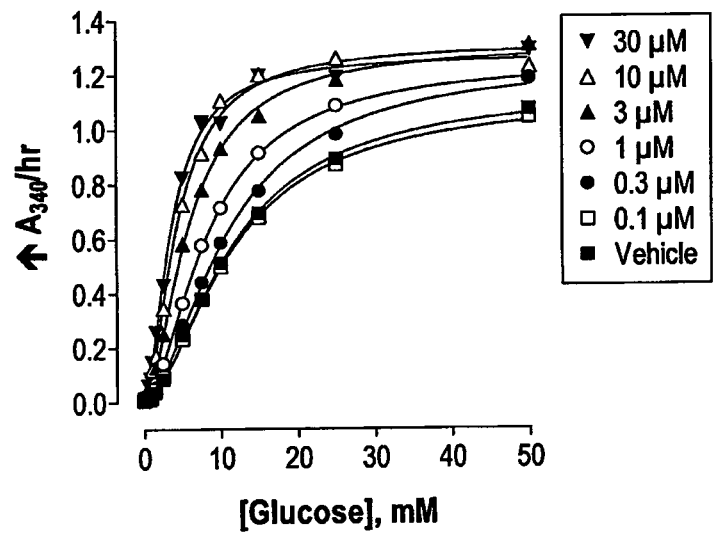
FIG. 3: Dose dependent glucokinase activation by Example-A11 at various glucose concentrations. The activity of glucokinase (presented as the increase in NADH absorbance over time) is shown at different glucose concentrations in the presence of different concentrations of Example-A11.
Figure 4:
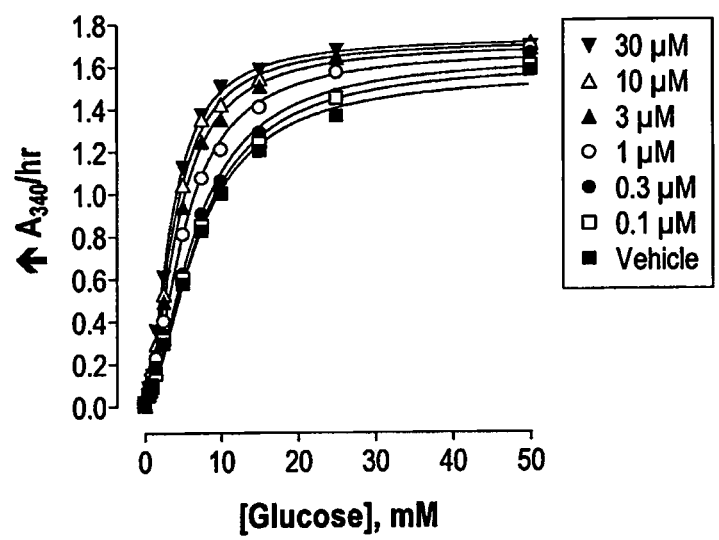
FIG. 4: Dose dependent glucokinase activation by Example-O15 at various glucose concentrations. The activity of glucokinase (presented as the increase in NADH absorbance over time) is shown at different glucose concentrations in the presence of different concentrations of Example-O15.
Figure 5:
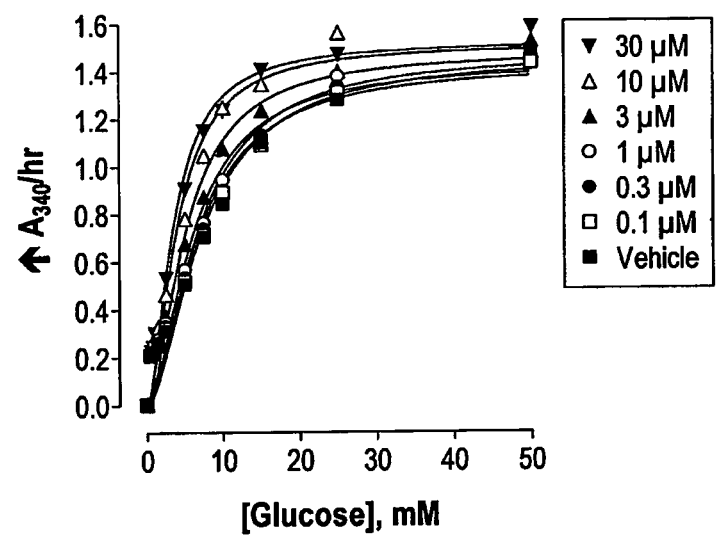
FIG. 5: Dose dependent glucokinase activation by Example-J1 at various glucose concentrations. The activity of glucokinase (presented as the increase in NADH absorbance over time) is shown at different glucose concentrations in the presence of different concentrations of Example-J1.

An important concept for understanding the disclosure is that full and partial activators of glucokinase behave differently in enzyme based glucokinase activation assay, as given under:

Glucokinase activators such as Ro-28-1675, when analyzed for their dose dependent effect on reduction of $S_{0.5}$ of glucokinase for glucose in an enzyme-based in vitro assay, showed a drop in $S_{0.5}$ from approximate 8 mM glucose all the way down to approximately 1.0 mM or less. FIG. 1 illustrates the kinetics of GK activation using various concentration of Ro-28-1675 at different glucose concentrations. The $E_{max}$ and $EC_{50}$ values are derived from a secondary plot where % $\Delta S_{0.5}$ is measured against different concentrations of Ro-28-1675. FIG. 2B illustrates such a derived plot, taking $S_{0.5}$ data from FIG. 2A. Thus $E_{max}$ and $EC_{50}$ of Ro-28-1675 are 90% and 770 nM respectively.

Applicants conceptualized that the hypoglycemic potential of a GK activator can be predicted by monitoring the effect of a GK activator on the reduction of $S_{0.5}$ of Glucokinase for glucose ($\Delta S_{0.5}$) in an in vitro assay:
        GK activator that shifts the $S_{0.5}$ of glucokinase by 90% or more is full activator; and
        GK activator that shifts the $S_{0.5}$ of glucokinase ranging between 20% and 90% is classified as partial activator of glucokinase.

Another aspect of this disclosure is to provide a method of identifying partial glucokinase activators, said method comprising
    i. determining the dose dependent effect of a glucokinase activator on % $\Delta S_{0.5}$ and obtain $EC_{50}$ and $E_{max}$ values;
    ii. comparing the $E_{max}$ obtained, with a well-characterized full activator of glucokinase known to produce hypoglycemia;
    iii. selecting compounds having $E_{max}$ in the range of 90% to 20% compared to full activators.

$E_{max}$, thus defined, of a partial GK activator should be significantly less than that of the well-characterized full activators. Compounds that shift $S_{0.5}$ of glucokinase more than 90% have been classified here as full activators. Compounds that shift $S_{0.5}$ of glucokinase between 90-20% have been classified as partial activators of glucokinase.

In another embodiment of the disclosure, it includes identification of partial glucokinase activators using the above method from compounds of formula (I).

In another embodiment, this invention includes a method for treating hyperglycemia using any partial activator of glucokinase identified by any method of the present disclosure.

In another embodiment, it includes demonstration of efficacy of partial activators of glucokinase in cell based assays where effects are mediated by glucokinase.

In a further embodiment of the disclosure, it includes the method of identifying partial glucokinase activator, as above, wherein, the said partial activators will have $E_{max}$ in the range of 60-90%.

In a further embodiment of the disclosure, it includes the method of identifying partial glucokinase activator, as above, wherein the said partial activators will have $E_{max}$ in the range of 40-60%.

In a further embodiment of the disclosure, it includes the method of identifying partial glucokinase activator, as above, wherein the said partial activators will have $E_{max}$ in the range of 20-40%.

In a further embodiment of the disclosure, it includes partial activators of glucokinase which are identified by the method described in this disclosure for use in treatment for diseases where glucokinase activation is required.

In a further embodiment of the disclosure, it includes a method of treatment of glucokinase activator mediated disease by administering a therapeutically effective amount of partial glucokinase activator to a mammal in need of such treatment, wherein said partial glucokinase activator is identified by any method of the present disclosure.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art.

By "pharmaceutically acceptable salts" as used herein, it covers salts of compounds of formula (I) prepared from pharmaceutically acceptable non-toxic bases or acids including inorganic or organic bases and inorganic or organic acids.

Inorganic bases salts include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Salts in the solid form may exist in more than one crystal structure, and may also be in the form of hydrates. When the compound of the present invention is basic, salts may be prepared from pharmaceutically acceptable non-toxic acids, including inorganic and organic acids, such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are hydrochloric, maleic, phosphoric, citric, hydrobromic, sulfuric, fumaric, and tartaric acids.

By "therapeutically effective amount" in this disclosure, it means an amount of compound of formula (I), its polymorphs, stereoisomers, pharmaceutically acceptable salt, solvate or pro-drug thereof, that is sufficient for effective treatment of obesity and/or type II diabetes. The therapeutically effective amount or dosage of a compound according to this invention can vary within wide limits. The dosage will depend on individual requirements in each particular case including the specific compound(s) being administered, the manner of administration, the severity of condition being treated, as well as the patient being treated, which is readily determinable by a person skilled in the art.

In using a compound of formula (I), its polymorphs, stereoisomers, pharmaceutically acceptable salt, solvate or pro-drug thereof, for therapeutic or prophylactic purposes it will generally be administered so that a daily dose in the range, for example, about 0.01 mg to 100 mg per kg body weight is received, given if required in divided doses. In general lower doses will be administered when a parenteral route is employed. Thus, for example, for intravenous administration, a dose in the range, for example, about 0.01 mg to 30 mg per kg body weight will generally be used. Similarly, for administration by inhalation, a dose in the range, for example, about 0.01 mg to 30 mg per kg body weight will be used.

The disclosure also relates to compound of formula (I), or its polymorph, stereoisomer, prodrug, solvate or a pharmaceutically acceptable salt thereof, for treating a disease through Glucokinase activation.

The disclosure also relates to compound of formula (I), or its polymorph, stereoisomer, prodrug, solvate or a pharmaceutically acceptable salt thereof, for prophylactic or therapeutic treatment of hyperglycemia or diabetes, particularly type II diabetes.

The disclosure also relates to compound of formula (I), or its polymorph, stereoisomer, prodrug, solvate or a pharmaceutically acceptable salt thereof, for preventing diabetes, particularly type II diabetes, in a human demonstrating pre-diabetic hyperglycemia or impaired glucose tolerance.

The disclosure also relates to compound of formula (I), or its polymorph, stereoisomer, prodrug, solvate or a pharmaceutically acceptable salt thereof, for combined treatment or preventing diabetes and obesity.

The disclosure also relates to compound of formula (I), or its polymorph, stereoisomer, prodrug, solvate or a pharmaceutically acceptable salt thereof, for treating or preventing obesity.

The disclosure also relates to the use of a compound of formula (I), polymorphs, stereoisomers, pharmaceutically acceptable salt, solvate or pro-drug thereof, in the prophylactic or therapeutic treatment of dyslipidemia.

The disclosure also relates to identifying the compounds of formula (I), its polymorphs, stereoisomers, pharmaceutically acceptable salt, solvate or pro-drug thereof, which are beneficial for the prophylaxis, management, treatment, control of progression, or adjunct treatment of diseases and/or medical conditions where the activation of glucokinase would be beneficial, such as diabetes (both Type-I and Type-II), obesity, dyslipidemia, metabolic syndrome X, and/or diabetes-related complications and as therapeutic and/or prophylactic agents for obesity, metabolic syndrome X includes Type-II diabetes, obesity, dyslipidemia, hypertension, and atherosclerosis and like.

The disclosure further relates to compounds of formula (I), its polymorphs, stereoisomers, pharmaceutically acceptable salt, solvate or pro-drug thereof, for use in the manufacture of medicament for the treatment of diabetes, obesity, metabolic syndrome X, insulin resistance, impaired glucose tolerance and dyslipidemia.

The disclosure also relates to the use of a compound of formula (I), its polymorphs, stereoisomers, pharmaceutically acceptable salt, solvate or pro-drug thereof, in the manufacture of a medicament for the activation of Glucokinase.

The disclosure also relates to the use of a compound of formula (I), its polymorphs, stereoisomers, pharmaceutically acceptable salt, solvate or pro-drug thereof, in the manufacture of a medicament for the prevention of diabetes, particularly type II diabetes, in a human demonstrating pre-diabetic hyperglycemia or impaired glucose tolerance.

The disclosure also relates to a method of prophylactic or therapeutic treatment of hyperglycemia or diabetes, particularly type II diabetes, comprising a step of administering an effective amount of a compound of formula (I), its polymorphs, stereoisomers, pharmaceutically acceptable salt, solvate or pro-drug thereof.

The disclosure also relates to a method for the prevention of diabetes, particularly type II diabetes, in a human demonstrating pre-diabetic hyperglycemia or impaired glucose tolerance comprising a step of administering an effective prophylactic amount of a compound of formula (I), its polymorphs, stereoisomers, pharmaceutically acceptable salt, solvate or pro-drug thereof.

The disclosure also relates to a method of combined treatment of diabetes and obesity by administering an effective amount of a compound of formula (I), its polymorph, stereoisomer, prodrug, solvate or a pharmaceutically acceptable salt thereof, to a mammal in need of such treatment.

The disclosure also relates to the use of a compound of formula (I), polymorphs, stereoisomers, pharmaceutically acceptable salt, solvate or pro-drug thereof, for the prevention of diabetes, particularly type II diabetes, in a human demonstrating pre-diabetic hyperglycemia or impaired glucose tolerance.

The disclosure also relates to the use of a compound of formula (I), polymorphs, stereoisomers, pharmaceutically acceptable salt, solvate or pro-drug thereof, for use as medicament, for the prophylactic or therapeutic treatment of hyperglycemia or diabetes, particularly type II diabetes.

The disclosure also relates to the use of a compound of formula (I), polymorphs, stereoisomers, pharmaceutically acceptable salt, solvate or pro-drug thereof, in the manufacture of a medicament for the prophylactic or therapeutic treatment of hyperglycemia or diabetes, particularly type II diabetes.

The disclosure also relates to the use of a compound of formula (I), polymorphs, stereoisomers, pharmaceutically acceptable salt, solvate or pro-drug thereof, in the manufacture of a medicament for use in combined treatment or prevention of diabetes and obesity. The compounds and compositions of the present invention may be optionally employed in combination with one or more, from current or future therapy, other antidiabetic agents or anti-hyperglycemic agents, which include, for example, (a) insulin secretagogues such as sulfonylureas (e.g. Amaryl, glyburide, glimepiride, glipyride, glipizide, etc.); (b) Insulinotropic sulfonyl urea receptor ligands such as meglitinides (e.g. nateglinide, rapaglinide); (c) biguanides (e.g. metformin, phenformin, buformin, etc.); (d) glucagon antagonists (e.g. a peptide or non-peptide glucagon antagonist); (e) glucosidase inhibitors (e.g. acarbose, miglitol, etc.); (f) glucose sensitive insulinotropic agents (e.g. GLP-1, GLP-1 mimetics e.g Exendin-4); (g) insulin sensitizers (e.g. troglitazone, rosiglitazone, pioglitazone, etc.); (h) Dipeptidyl peptidase-IV inhibitors (e.g. sitagliptin, vildagliptin); and the like.

The compounds and compositions of the present invention may also be optionally employed in combination with one or more, from current or future therapy, anti-obesity agents (e.g. sibutramine, orlistat, rimonabant etc.) and the like.

The compounds and compositions of the present invention may also be optionally employed in combination with one or more, from current or future therapy, dyslipidemic agents which include, for example: (a) fibrates (e.g. gemfibrozil, fenofibrate); (b) Niacin; (c) Statins (e.g. rosuvatatin, atorvastatin, simvastatin); (d) cholesterol absorption inhibitors (e.g. Ezetimibe); (e) bile acid sequestrants (e.g. cholestyramine) and the likes.

The compounds and compositions of the present invention may also be optionally employed in combination with one or more, from current or future therapy, antihypertensive agents such as: (a) diuretics; (b) angiotensin converting enzyme (ACE) inhibitors; (c) Angiotensin-II receptor type-I blockers (ARB); (d) rennin inhibitors; (e) β-adrenergic receptor blockers; (f) calcium channel blockers; (g) aldosterone receptor antagonist; (h) aldosterone synthase inhibitors.

The compounds and compositions of the present invention and the other therapeutic agents such as described above may be administered simultaneously, sequentially or separately.

The pharmaceutical compositions of the present invention comprise a compound of formula (I), polymorphs, stereoisomers, pharmaceutically acceptable salt, solvate or pro-drug thereof, as an active ingredient, a pharmaceutically acceptable carrier and optionally other therapeutic active agent in any suitable ratios. Such therapeutic active agents may be selected from antidiabetic agents, antihyperlipidemic agents, antiobesity agents, antihypertensive agents and agents for the treatment of complications resulting from or associated with diabetes.

The pharmaceutical compositions of the present invention comprising compounds of formula (I), polymorphs, stereoisomers, pharmaceutically acceptable salt, solvate or pro-drug thereof, may be manufactured in a manner that is known in the art, e.g. by means of conventional mixing, encapsulating, dissolving, granulating, emulsifying, entrapping, dragée-making, or lyophilizing processes. These pharmaceutical preparations can be formulated with therapeutically inert, inorganic or organic carriers such as lactose, corn starch or derivatives thereof, talc, steric acid or its salts as carriers for tablets, coated tablets, dragées and hard gelatin capsules. For soft gelatin capsules suitable carriers include vegetable oils, waxes and fats. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula (I), its polymorphs, stereoisomers, pharmaceutically acceptable salt, solvate or pro-drug thereof.

The pharmaceutical compositions containing the active ingredient of compound of formula (I), its polymorphs, stereoisomers, pharmaceutically acceptable salt, solvate or pro-drug thereof, may be in a form suitable for oral use, for example, as tablets, troches, lozenges, aqueous or oily suspensions, dispersible powders or granules, emulsions, hard or soft capsules, or syrups or elixirs. These compositions can be manufactured by any method known in the art with the active ingredient combined with non-toxic pharmaceutically acceptable excipients such as inert diluents, eg. calcium carbonate, sodium carbonate, lactose, calcium phosphate or sodium phosphate; granulating and disintegrating agents, eg. corn starch, or alginic acid; binding agents, eg. starch, gelatin or acacia, and lubricating agents, eg. magnesium stearate, stearic acid or talc. The composition also contains optionally agents for pharmaceutically elegant and palatable preparations, selected from the group consisting of sweetening agents, flavoring agents, coloring agents and preserving agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Oral formulation as hard gelatin capsules can be prepared by mixing the active ingredient is with an inert solid diluent, such as, calcium carbonate, calcium phosphate or kaolin, or as soft gelatin capsules wherein the active ingredient is mixed with water or an oil medium, such as peanut oil, liquid paraffin or olive oil.

Aqueous suspensions of the active ingredient of compound of formula (I), its polymorphs, stereoisomers, pharmaceutically acceptable salt, solvate or pro-drug thereof, can be prepared in admixture with excipients suitable for the manufacture of aqueous suspensions. Such excipients are suspending agents, such as sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, such as lecithin, or condensation products of an alkylene oxide with fatty acids, for example polyoxyethylene stearate, or condensation products of ethylene oxide with long chain aliphatic alcohols, such as heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, such as ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, such as arachis oil, olive oil, sesame oil or coconut oil, or in a mineral oil such as liquid paraffin. The oily suspensions may contain a thickening agent, such as beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agent.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The compounds of the present invention may also be for topical use, creams, ointments, jellies, solutions or suspensions, etc. For purposes of this application, topical application shall include mouth washes and gargles.

Several methods for preparing the compounds of formula (I) are illustrated in the following schemes and examples.

Synthesis Type-A

Example A1

2-(4-Chloro-phenoxy)-2-methyl-N-thiazol-2-yl-propionamide

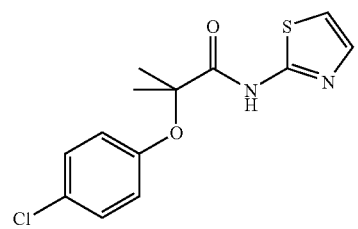 [SMILES: CC(C)(Oc1ccc(Cl)cc1)C(=O)Nc1nccs1]

To a solution of 2-(4-Chloro-phenoxy)-2-methyl-propionic acid (0.3 g, 1.4 mmol) in DCM (10 ml) was added triethylamine (0.23 ml, 1.68 mmol) and HOBt (0.23 g, 1.68 mmol) at 0° C. After stirring at this temperature for 5 min. added 2-aminothiazole (0.168 g, 1.68 mmol) and followed by EDCI (0.332 g, 1.68 mmol). The resulting solution was stirred for 12 h. then quenched with saturated aqueous $NH_4Cl$ solution (15 mL). The aqueous phase was extracted with $CH_2Cl_2$ (3×50 mL). The organic phase was successively washed with 2% HCl (50 mL), brine (50 mL) and dried over $Na_2SO_4$. After evaporation, the residue was purified by flash chromatography (1:10 ethyl acetate:hexanes) to give 2-(4-Chloro-phenoxy)-2-methyl-N-thiazol-2-yl-propionamide (0.325 g, 78%). $^1$H NMR (400 MHz, $CDCl_3$): δ 1.58 (s, 6H), 6.76 (d, J=8.8 Hz, 2H), 7.01 (d, J=3.6 Hz, 1H), 7.18 (d, J=8.8 Hz, 2H), 7.50 (d, J=3.6 Hz, 1H), MS (EI) m/z 296.9 (M+1).

Preparation of 2-(4-Chloro-phenoxy)-2-methyl-propionic acid used in Typical Example A1 is described below:

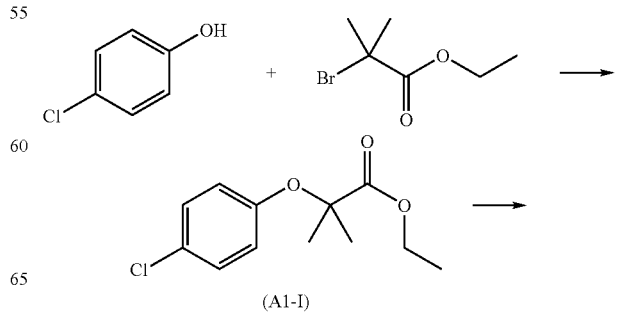

(A1-I)

2-(4-Chloro-phenoxy)-2-methyl-propionic acid ethyl ester (A1-I)

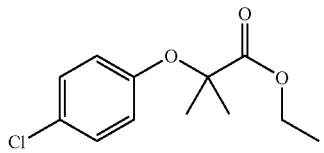 [SMILES: CCOC(=O)C(C)(C)Oc1ccc(Cl)cc1]

To a solution of 4-chloro-phenol (4 g, 31.11 mmol) in DMF (10 ml) anhydrous potassium carbonate (10.73 g, 77.77 mmol) and ethyl-2-bromo-isobutyrate (12.13 g, 62.22 mmol) were added. The resulting mixture was heated at 70° C. for 12 hours. Upon completion (~25 h), the solution was diluted with EtOAc (100 ml) and washed with brine (2×20 ml). The aqueous layer was then extracted for two additional times with EtOAc (20 ml) and the combined organic fractions were washed with brine (20 ml). The solution was then dried over $Na_2SO_4$ and concentrated to give brown oil. Purification on silica gel (hexanes/acetone) yielded 6.0 g (79%) of ester as pale yellow oil which was used as such for the next step without further purification.

2-(4-Chloro-phenoxy)-2-methyl-propionic acid (A1-II)

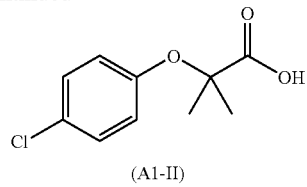

To a solution of 2-(4-Chloro-phenoxy)-2-methyl-propionic acid ethyl ester (6 g, 24.79 mmol) in THF (20 ml) was added a solution of LiOH (3 g, 74.38 mmol) in $H_2O$ (4 ml). The resulting solution was stirred at room temperature for 12 hours. After evaporation of the solvent, the residue was diluted with ethyl acetate (100 ml); cool to 0° C., acidified with 1N HCl (PH~3-4). The organic phase were washed with, brine (20 ml) and dried over $Na_2SO_4$. After evaporation, the residue was purified by flash chromatography (1:1 hexanes/EtOAc) to give 2-(4-Chloro-phenoxy)-2-methyl-propionic acid (1.1 g, 20%). $^1$H NMR (400 MHz, $CDCl_3$): δ 1.60 (s, 6H), 6.85 (d, J=8.7 Hz, 2H), 7.22 (d, J=8.7 Hz, 2H). MS (EI) m/z: 215.5 (M+1).

Following examples were prepared in an analogous manner of Example A1 from the appropriate intermediates.

| Example | Structure | IUPAC name and analytical data |
|---|---|---|
| A2 | 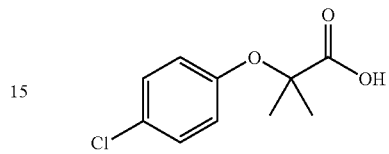 | 2-Methyl-2-(4-methylsulfanyl-phenoxy)-N-thiazol-2-yl-propionamide.<br>$^1$H NMR (400 MHz, $CDCl_3$): δ 1.58 (s, 6H), 2.46 (s, 3H), 6.88-6.90 (m, 2H), 7.02 (d, J = 3.6 Hz, 1H), 7.1-7.21 (m, 2H), 7.48 (d, J = 4 Hz, 1H), 10.1 (bs, 1H). |
| A3 | 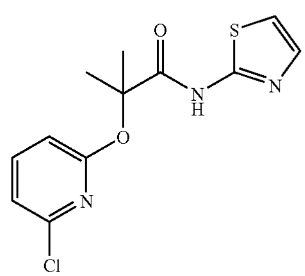 | MS (EI) m/z: 309 (M + 1).<br>2-(6-Chloro-pyridin-2-yloxy)-2-methyl-N-thiazol-2-yl-propionamide.<br>$^1$H NMR (400 MHz, $CDCl_3$): δ 1.80 (s, 6H), 6.64 (d, J = 7.6 Hz, 1H), 6.91 (d, J = 7.6 Hz, 1H), 6.99 (d, J = 3.6 Hz, 1H), 7.46 (d, J = 3.6 Hz, 1H), 7.53 (t, 1H). |
| A4 | 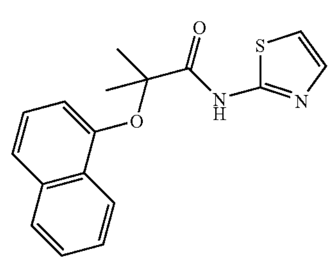 | MS (EI) m/z 298 (M + 1).<br>2-Methyl-2-(naphthalen-1-yloxy)-N-thiazol-2-yl-propionamide.<br>$^1$H NMR (400 MHz, CDC13): δ1.7 (s, 6H), 6.85 (d, J = 7.6 Hz, 1H), 7.03 (d, J = 3.6 Hz, 1H), 7.29 (m, 1H), 7.45 (d, J = 3.6 Hz, 1H), 7.48-7.54 (m, 2H), 7.56 (d, J = 8 Hz, 1H), 7.82-7.84 (m, 1H), 8.18-8.21 (m, 1H), 10.3 (s, 1H). |

| Example | Structure | IUPAC name and analytical data |
|---|---|---|
| A5 | 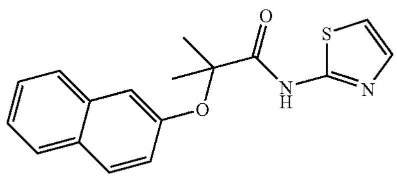 [SMILES: CC(C)(Oc1ccc2ccccc2c1)C(=O)Nc1nccs1] | MS (EI) m/z: 313.1 (M + 1).<br>mp: 117-118° C.<br>2-Methyl-2-(naphthalen-2-yloxy)-N-thiazol-2-yl-propionamide.<br>$^1$H NMR (400 MHz, CDCl$_3$): δ1.7 (s, 6H), 7.04 (d, J = 3.2 Hz, 1H), 7.17 (dd, J = 2.4 Hz, 9.2 Hz, 1H), 7.32 (d, J = 2.4 Hz, 1H), 7.42 (m, 1H), 7.45 (dd, J = 1.6 Hz, 4.4 Hz, 1H), 7.47-7.48 (m, 1H), 7.49 (d, J = 1.6 Hz, 1H), 7.74 (d, J = 7.6 Hz, 1H), 7.81 (m, 1H), 10.2 (s, 1H). |
| A6 | 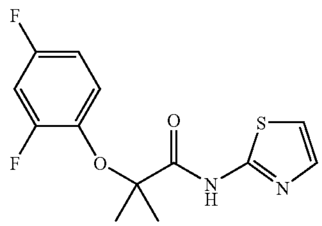 | MS (EI) m/z: 313.1 (M + 1).<br>2-(2,4-Difluoro-phenoxy)-2-methyl-N-thiazol-2-yl-propionamide.<br>$^1$H NMR (400 MHz, CDCl$_3$): δ 1.50 (s, 6H), 6.80-6.86 (m, 1H), 6.88-6.96 (m, 1H), 7.02 (d, J = 3.6 Hz, 1H), 7.02-7.10 (m, 1H), 7.50 (d, J = 3.6 Hz, 1H). |
| A7 | 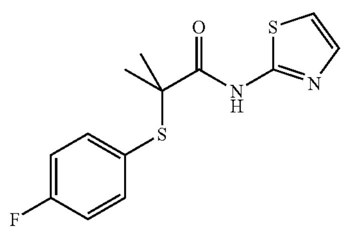 [SMILES: CC(C)(Sc1ccc(F)cc1)C(=O)Nc1nccs1] | MS (EI) m/z 299 (M + 1).<br>2-(4-Fluoro-phenylsulfanyl)-2-methyl-N-thiazol-2-yl-propionamide.<br>$^1$H NMR (400 MHz, CDCl3): δ 1.6 (s, 6H), 6.96-7.03 (m, 3H), 7.26-7.41 (m, 2H), 7.50 (d, J = 3.6 Hz, 1H), 10 (bs, 1H). |
| A8 | 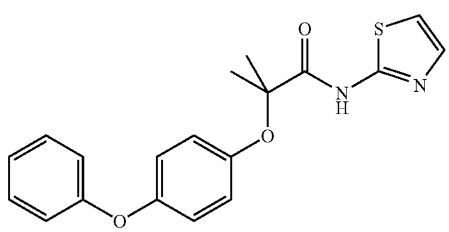 | MS (EI) m/z: 297.1 (M + 1).<br>2-Methyl-2-(4-phenoxy-phenoxy)-N-thiazol-2-yl-propionamide.<br>$^1$H NMR (400 MHz, CDCl$_3$): δ 1.58 (s, 6H), 6.94 (bs, 4H), 6.99 (d, J = 8.8 Hz, 2H), 7.03 (d, J = 3.6 Hz, 1H), 7.10 (t, 1H), 7.34 (t, 2H), 7.50 (d, J = 3.6 Hz, 1H). |
| A9 | 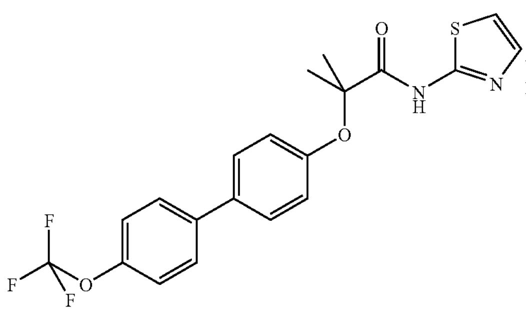 | MS (EI) m/z 355.1 (M + 1).<br>2-Methyl-N-thiazol-2-yl-2-(4'-trifluoromethoxy-biphenyl-4-yloxy)-propionamide.<br>$^1$H NMR (400 MHz, CDCl$_3$): δ 1.58 (s, 6H), 7.03 (d, J = 3.6 Hz, 1H), 7.04 (d, J = 8.8 Hz, 2H), 7.28 (d, J = 8.8 Hz, 2H), 7.48 (d, J = 8.8 Hz, 2H), 7.50 (d, J = 3.6 Hz, 1H), 7.55 (d, J = 8.8 Hz, 2H). |
| A10 | 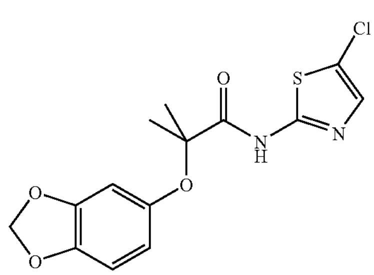 | MS (EI) m/z 423.1 (M + 1).<br>2-(Benzo[1,3]dioxol-5-yloxy)-N-(5-chloro-thiazol-2-yl)-2-methyl-propionamide.<br>(CDCl3): 1.55 (s, 6H), 5.96 (s, 2H), 6.41 (dd, J = 2.4 Hz ,1H), 6.49 (d, J = 2.4 Hz, 1H), 6.69 (d, J = 8.4 Hz, 1H), 7.31 (s, 1H). |

-continued

| Example | Structure | IUPAC name and analytical data |
|---|---|---|
| A11 | 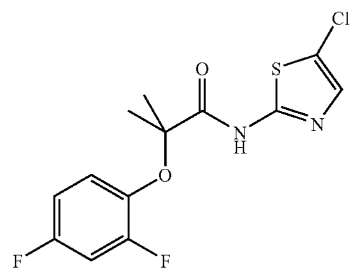 | MS (EI) m/z 341.0 (M + 1).<br>N-(5-Chloro-thiazol-2-yl)-2-(2,4-difluoro-phenoxy)-2-methyl-propionamide.<br>$^1$H NMR (400 MHz, CDCl$_3$): δ 1.6 (s, 6H), 6.82-8.86 (m, 1H), 6.89-6.94 (m, 1H), 7.02-7.08 (m, 1H), 7.35 (s, 1H). |
| A12 | 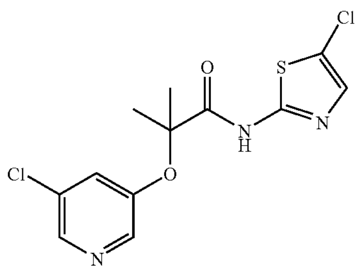 [SMILES: CC(C)(Oc1cncc(Cl)c1)C(=O)Nc1ncc(Cl)s1] | MS (EI) m/z 333 (M + 1).<br>2-(5-Chloro-pyridin-3-yloxy)-N-(5-Chloro-thiazol-2-yl)-2-methyl-propionamide.<br>$^1$H NMR (400 MHz, CDCl$_3$): 1.6 (s, 6H), 7.29-7.30 (m, 1H), 7.32 (s, 1H), 8.22 (d, J = 2.4 Hz, 1H), 8.38 (d, J = 2.4 Hz, 1H). |
| A13 | 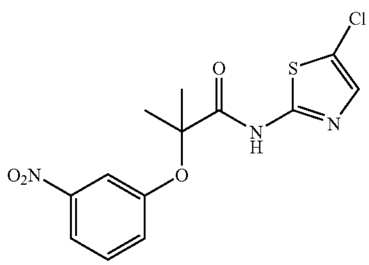 | MS (EI) m/z: 332 (M + 1).<br>N-(5-Chloro-thiazol-2-yl)-2-methyl-2-(3-nitro-phenoxy)-propionamide.<br>$^1$H NMR (400 MHz, CDCl$_3$): δ 1.62 (s, 6H), 7.33 (d, J = 8 Hz, 1H), 7.57 (m, 2H), 7.70 (bs, 1H), 7.88 (d, J = 8 Hz, 1H), 7.85 (t, J = 2 Hz, 1H), 12.70 (bs, 1H). |
| A14 | 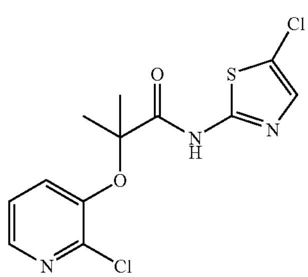 | MS (EI) m/z: 342.2 (M + 1).<br>2-(2-Chloro-pyridin-3-yloxy)-N-(5-Chloro-thiazol-2-yl)-2-methyl-propionamide.<br>$^1$H NMR (400 MHz, CDCl$_3$): δ 1.59 (s, 6H), 7.23-7.26 (m, 1H), 7.33 (s, 1H), 7.38-7.40 (m, 1H), 8.20 (d, J = 4.4 Hz, 1H), 10.2 (bs, 1H). |
| A15 | 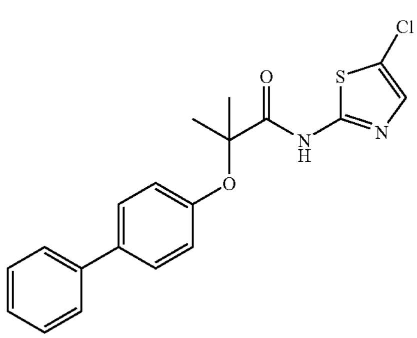 | MS (EI) m/z: 331.9 (M + 1).<br>mp: 184-185° C.<br>2-(Biphenyl-4-yloxy)-N-(5-Chloro-thiazol-2-yl)-2-methyl-propionamide.<br>$^1$H NMR (400 MHz, CDCl$_3$): δ 1.59 ( s, 6H), 7.0 (d, J = 8.8 Hz, 2H), 7.31-7.35 (m, 2H), 7.43 (t, J = 7.6 Hz, 2H), 7.50-7.55 (m, 4H), 10.25 (bs, 1H). |

| Example | Structure | IUPAC name and analytical data |
|---|---|---|
| A16 | 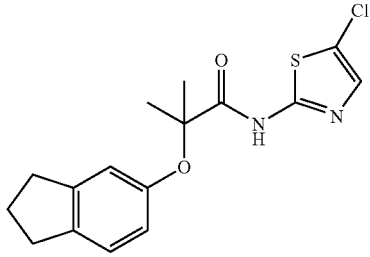 | MS (EI) m/z: 373.1 (M + 1).<br>N-(5-Chloro-thiazol-2-yl)-2-(indan-5-yloxy)-2-methyl-propionamide.<br>$^1$H NMR (400 MHz, CDCl$_3$): δ 1.58 (s, 6H), 2.09 (q, J = 7.6 Hz, 2H), 2.87-2.9 1 (q, J = 7.2 Hz, 4H), 6.74 (d, 1H), 6.83 (s, 1H), 7.14 (d, J = 7.6 Hz, 1H), 7.33 (s, 1H), 10.1 (bs, 1H). |
| A17 | 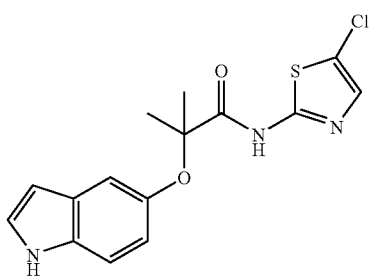 [SMILES: CC(C)(Oc1ccc2[nH]ccc2c1)C(=O)Nc1ncc(Cl)s1] | MS (EI) m/z: 337 (M + 1).<br>N-(5-Chloro-thiazol-2-yl)-2-(1H-indol-5-yloxy)-2-methyl-propionamide.<br>$^1$H NMR (400 MHz, CDCl$_3$): δ 1.58 (s, 6H), 6.51 (s, 1H), 6.85 (d, J = 8.8 Hz, 1H), 7.22-7.32 (m, 4H). |
| A18 | 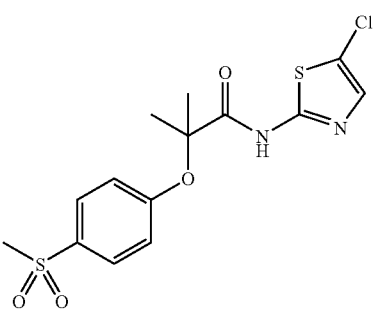 | MS (EI) m/z: 336 (M + 1).<br>N-(5-Chloro-thiazol-2-yl)-2-(4-methanesulfonyl-phenoxy)-2-methyl-propionamide.<br>$^1$H NMR (400 MHz, CDCl$_3$): δ 1.7 (s, 6H), 3.04 (s, 3H), 7.0 (d, J = 8.8 Hz, 2H), 7.32 (s, 1H), 7.87 (d, J = 8.4 Hz, 2H), 10.0 (bs, 1H). |
| A19 | 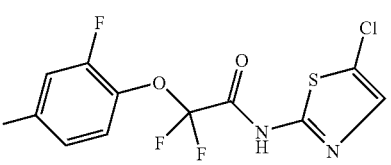 | MS (EI) m/z 374.9 (M + 1).<br>N-(5-Chloro-thiazol-2-yl)-2-(2,4-difluoro-phenoxy)-2,2-difluoro-acetamide.<br>$^1$H NMR (400 MHz, CDCl$_3$): δ 6.91-7.01 (m, 2H), 7.3 1-7.37 (m, 2H), 10.38 (bs, 1H) |
| A20 | 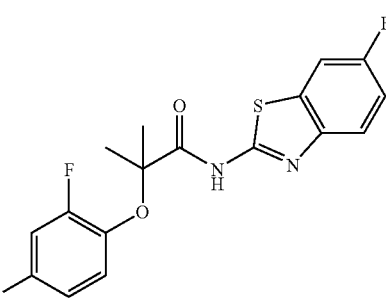 | MS (EI) m/z: 340.9 (M + 1).<br>2-(2,4-Difluoro-phenoxy)-N-(6-fluoro-benzothiazol-2-yl)-2-methyl-propionamide.<br>$^1$H NMR (400 MHz, CDCl$_3$): 1.6 (s, 6H), 6.83-6.87 (m, 1H), 6.90-6.96 (m, 1H), 7.04-7.10 (m, 1H), 7.16-7.21 (m, 1H), 7.53 (dd, J = 8.4 Hz, 1H), 7.73-7.76 (m, 2H). |
| A21 | 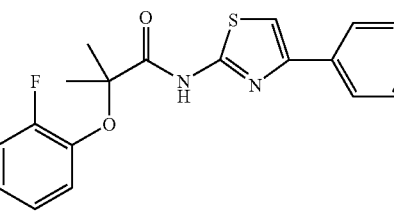 | MS (EI) m/z 367 (M + 1).<br>2-(2,4-Difluoro-phenoxy)-2-methyl-N-(4-phenyl-thiazol-2-yl)-propionamide.<br>$^1$H NMR (400 MHz, CDCl$_3$): δ 1.6 (s, 6H), 6.82-6.86 (m, 1H), 6.90-6.96 (m, 1H), 7.04-7.10 (m, 1H), 7.19 (s, 1H), 7.31 (t, J = 7.2 Hz, 1H), 7.42 (t, J = 8 Hz, 2H), 7.84 (d, J = 7.6 Hz, 2H). |

| Example | Structure | IUPAC name and analytical data |
|---|---|---|
| A22 | 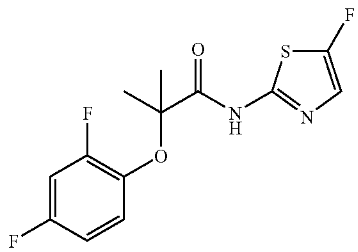 | MS (EI) m/z: 375 (M + 1).<br>2-(2,4-Difluoro-phenoxy)-N-(5-fluoro-thiazol-2-yl)-2-methyl-propionamide.<br>$^1$H NMR (400 MHz, CDCl$_3$): δ 1.52 (s, 6H), 6.80-6.84 (m, 1H), 6.87-6.92 (m, 1H), 7.0-7.05 (m, 2H), 9.99 (bs, 1H). |
| A23 | 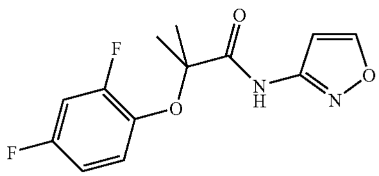 [SMILES: CC(C)(Oc1ccc(F)cc1F)C(=O)Nc1ccon1] | MS (EI) m/z 317 (M + 1).<br>2-(2,4-Difluoro-phenoxy)-N-isoxazol-3-yl-2-methyl-propionamide.<br>$^1$H NMR (400 MHz, CDCl$_3$): δ 1.52 (s, 6H), 6.83 (m, 1H), 6.81-6.86 (m, 1H), 7.05 (s, 1H), 7.12 (d, J = 1.2 Hz, 1H), 8.34 (s, 1H), 9.42 (bs, 1H). |
| A24 | 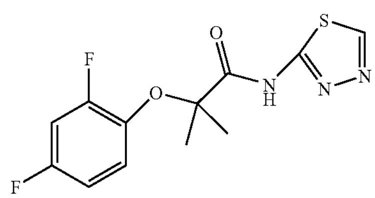 | MS (EI) m/z: 282.9 (M + 1).<br>2-(2,4-Difluoro-phenoxy)-2-methyl-N-[1,3,4]thiadiazol-2-yl-propionamide.<br>$^1$H NMR: (400 MHz, CDCl3: δ 1.59 (s, 6H), 6.84-6.88 (m, 1H), 6.91-6.96 (m, 1H), 7.05-7.26 (m, 1H), 8.89 (s, 1H), 10.2 (brs, 1H). |
| A25 | 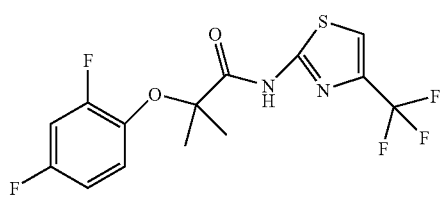 [SMILES: CC(C)(Oc1ccc(F)cc1F)C(=O)Nc1nc(C(F)(F)F)cs1] | MS (EI) m/z: 300 (M + 1).<br>2-(2,4-Difluoro-phenoxy)-2-methyl-N-(4-trifluoromethyl-thiazol-2-yl)-propionamide.<br>$^1$H NMR: (400 MHz, CDCl3): δ 1.59 (s, 6H), 6.83-6.88 (m, 1H), 6.90-6.96 (m, 1H), 7.03-7.09 (m, 1H), 7.46 (s, 1H), 10.12 (brs, 1H). |
| A26 | 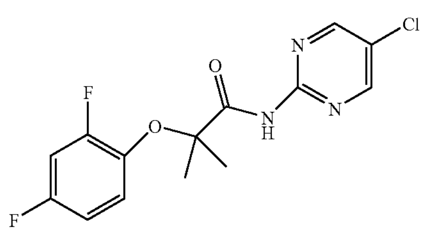 | MS (EI) m/z: 367 (M + 1).<br>N-(5-Chloro-pyrimidin-2-yl)-2-(2,4-difluoro-phenoxy)-2-methyl-propionamide.<br>$^1$H NMR: (400 MHz, CDCl$_3$): δ 1.59 (s, 6H), 6.81-6.86 (m, 1H), 6.90-6.95 (m, 1H), 7.06-7.12 (m, 1H), 8.65 (s, 2H), 9.6 (brs, 1H). |
| A27 | 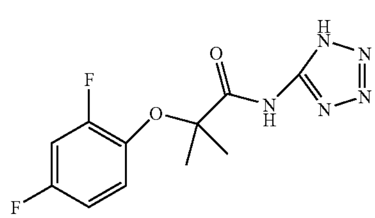 | MS (EI) m/z: 328.1 (M + 1).<br>2-(2,4-Difluoro-phenoxy)-2-methyl-N-(1H tetrazol-5-yl)-propionamide.<br>$^1$H NMR: (400 MHz, CDCl3): δ 1.59 (s, 6H), 6.85-6.90 (m, 1H), 6.92-6.97 (m, 1H), 7.06-7.12 (m, 1H), 10.1 (brs, 1H), 13.3 (brs, 1H). |
| A28 | 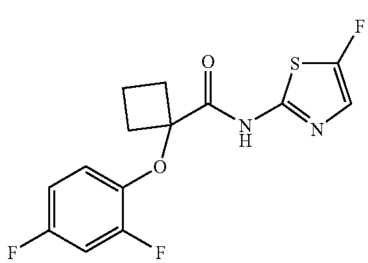 [SMILES: O=C(Nc1ncc(F)s1)C1(Oc2ccc(F)cc2F)CCC1] | MS (EI) m/z: 284.1 (M + 1).<br>1-(2,4difluorophenoxy)-N-(5-fluorothiazol-2-yl)cyclobutanecarboxamide<br>$^1$H NMR (400 MHz, CDCl$_3$): δ 1.91-1.96 (m, 1H), 2.05-2.08 (m, 1H), 2.41-2.45 (m, 2H), 2.70-2.75 (m, 2H), 6.66-6.78 (m, 2H), 6.90-6;9 (m, 1H), 7.05 (d, J = 3.2 Hz, 1H), 9.51 (bs, 1H). |

| Example | Structure | IUPAC name and analytical data |
|---|---|---|
| A29 | 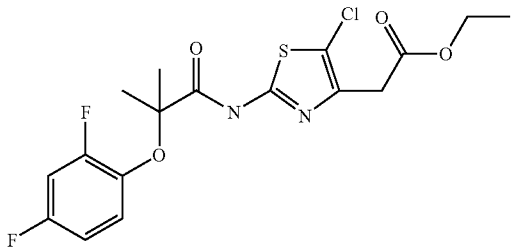 [SMILES: CCOC(=O)Cc1nc(NC(=O)C(C)(C)Oc2ccc(F)cc2F)sc1Cl] | MS (EI) m/z: 329.00 (M + 1).<br>{5-Chloro-2-[2-(2,4-difluoro-phenoxy)-2-methyl-propionylamino]-thiazol-4-yl}-acetic acid ethyl ester<br>$^1$H NMR (400 MHz, CDCl$_3$): δ 1.28 (t, J = 7.2 Hz, 3H), 1.54 (s, 6H), 3.71 (s, 2H), 4.20 (q, J = 7.2 Hz, 2H), 6.816-6.83 (m, 1H), 6.85-6.91 (m, 1H), 7.01-7.07 (m, 1H).<br>MS (EI) m/z: 419.0 (M + 1). |

Synthesis Type-B

Example B1

{2-[2-Methyl-2-(naphthalen-1-yloxy)-propionylamino]-thiazol-4-yl}-acetic acid

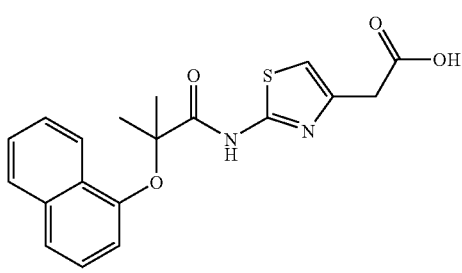 [SMILES: CC(C)(Oc1cccc2ccccc12)C(=O)Nc1nc(CC(=O)O)cs1]

To a solution of {2-[2-Methyl-2-(naphthalen-1-yloxy)-propionylamino]-thiazol-4-yl}-acetic acid ethyl ester (0.196 g, 5 mmol) in THF (2 ml) and MeOH (1 ml) added a solution of LiOH (0.021 g, 25 mmol) in H$_2$O (1 ml) and stirred at r.t. for 18 h. Solvents were evaporated under reduced pressure and residue was dissolved in water (5 ml) and extracted with ether (2×2 ml). The aqueous phase was acidified with citric acid solution, extracted in EtOAc (2×30 ml), dried over Na$_2$SO$_4$ and the solvent was evaporated under reduced pressure to obtain {2-[2-Methyl-2-(naphthalen-1-yloxy)-propionylamino]-thiazol-4-yl}-acetic acid (0.16 g, 89%). $^1$H NMR (400 MHz, CDCl$_3$): δ1.72 (s, 6H), 3.42 (s, 2H), 6.34 (s, 1H), 6.74 (d, J=7.2 Hz, 1H), 7.29 (d, J=8 Hz, 1H), 7.49-7.55 (m, 3H), 7.83-7.85 (m, 1H), 8.23-8.25 (m, 1H), MS (EI) m/z: 371.00 (M+1).

Following compounds were prepared in an analogous manner of Example B1 from the appropriate intermediates

| Example | Structure | IUPAC name and analytical data |
|---|---|---|
| B2 | 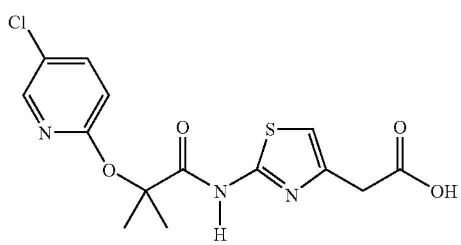 [SMILES: CC(C)(Oc1ccc(Cl)cn1)C(=O)Nc1nc(CC(=O)O)cs1] | {2-[2-(5-Chloro-pyridin-2-yloxy)-2-methyl-propionylamino]-thiazol-4-yl}-acetic acid.<br>$^1$H NMR (400 MHz, CDCl$_3$): δ 1.75 (s, 6H), 3.57 (s, 2H), 6.69 (d, J = 8.4 Hz, 1H), 6.75 (s, 1H), 7.44 (dd, J = 2.8 Hz, 1H), 7.9 (d, J = 2.4 Hz, 1H).<br>MS (EI) m/z 354.1 (M + 1). |
| B3 | 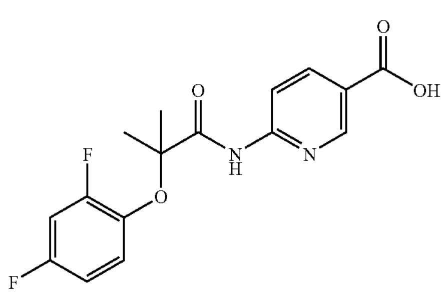 [SMILES: CC(C)(Oc1ccc(F)cc1F)C(=O)Nc1ccc(C(=O)O)cn1] | 6-[2-(2,4-Difluoro-phenoxy)-2-methyl-propionylamino]-nicotinic acid.<br>$^1$H NMR (400 MHz, CDCl$_3$): δ 1.6 (s, 6H), 6.81-6.86 (m, 1H), 6.89-6.94 (m, 1H), 7.05-7.11 (m, 1H), 8.40 (t, 2H), 9.0 (s, 1H), 9.68 (s, 1H).<br>MS (EI) m/z: 337 (M + 1). |

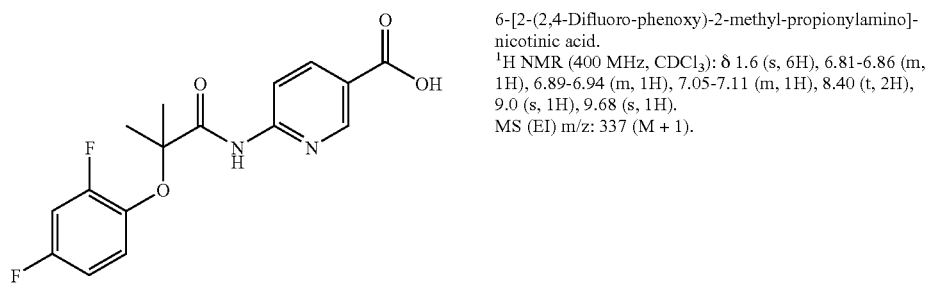

-continued

| Example | Structure | IUPAC name and analytical data |
|---|---|---|
| B4 | 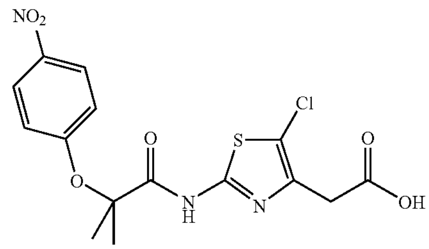 [SMILES: CC(C)(Oc1ccc([N+](=O)[O-])cc1)C(=O)Nc1nc(CC(=O)O)c(Cl)s1] | {5-Chloro-2-[2-methyl-2-(4-nitro-phenoxy)-propionylamino]-thiazol-4-yl}-acetic acid.<br>$^1$H NMR (400 MHz, CDCl$_3$): δ 1.70 (s, 6H), 3.64 (s, 2H), 6.97 (d, J = 9.2 Hz, 2H), 8.14 (d, J = 9.2 Hz, 2H).<br>MS (EI) m/z: 400.0 (M + 1). |
| B5 | 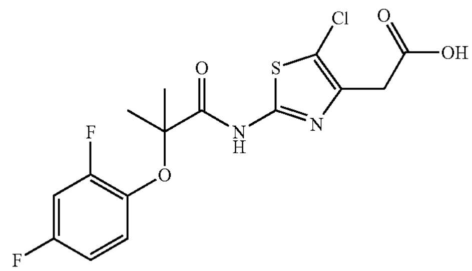 [SMILES: CC(C)(Oc1ccc(F)cc1F)C(=O)Nc1nc(CC(=O)O)c(Cl)s1] | {5-Chloro-2-[2-(2,4-difluoro-phenoxy)-2-methyl-propionylamino]-thiazol-4-yl}-acetic acid.<br>$^1$H NMR (400 MHz, CDCl$_3$): δ 1.6 (s, 6H), 3.70 (s, 2H), 6.79-6.84 (m, 1H), 6.87-6.92 (m, 1H), 7.01-7.08 (m, 1H).<br>MS (EI) m/z: 391 (M + 1). |
| B6 | 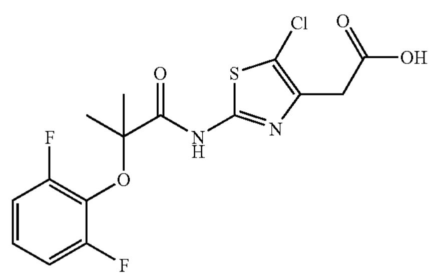 [SMILES: CC(C)(Oc1c(F)cccc1F)C(=O)Nc1nc(CC(=O)O)c(Cl)s1] | {5-Chloro-2-[2-(2,6-difluoro-phenoxy)-2-methyl-propionylamino]-thiazol-4-yl}-acetic acid.<br>$^1$H NMR (400 MHz, CDCl$_3$): δ 1.59 (s, 6H), 3.73 (s, 2H), 6.94 (t, J = 7.6 Hz, 2H), 7.08-7.11 (m, 1H), 10.1 (bs, 1H).<br>MS (EI) m/z 391 (M + 1). |
| B7 | 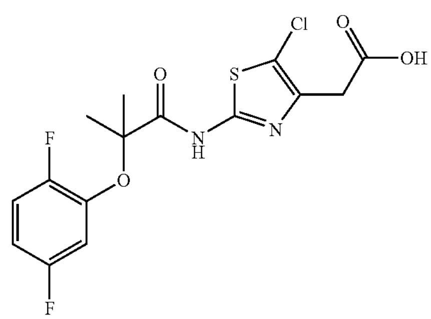 [SMILES: CC(C)(Oc1cc(F)ccc1F)C(=O)Nc1nc(CC(=O)O)c(Cl)s1] | {5-Chloro-2-[2-(2,5-difluoro-phenoxy)-2-methyl-propionylamino]-thiazol-4-yl}-acetic acid.<br>$^1$H NMR (400 MHz, CDCl$_3$): δ 1.59 (s, 6H), 3.71 (s, 2H), 6.78-6.86 (m, 2H), 7.05-7.11 (m, 1H), 9.9 (bs, 1H).<br>MS (EI) m/z 391 (M + 1). |
| B8 | 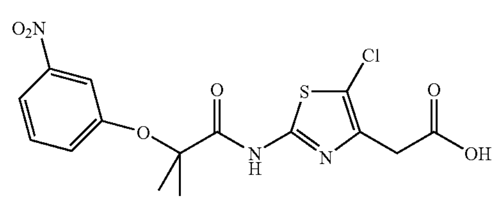 [SMILES: CC(C)(Oc1cccc([N+](=O)[O-])c1)C(=O)Nc1nc(CC(=O)O)c(Cl)s1] | {5-Chloro-2-[2-methyl-2-(3-nitro-phenoxy)-propionylamino]-thiazol-4-yl}-acetic acid.<br>$^1$H NMR (400 MHz, CDCl$_3$): δ 1.67 (s, 6H), 3.68 (s, 2H), 7.29 (s, 1H), 7.47 (t, J = 8.0 Hz, 1H), 7.85 (bs, 1H), 7.99 (d, J = 8 Hz, 1 H).<br>MS (EI) m/z: 400.0 (M + 1). |
| B9 | 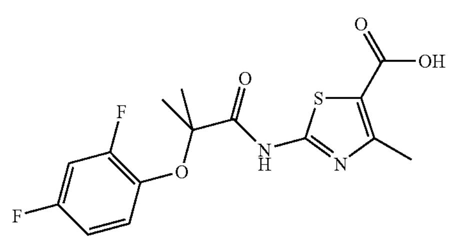 [SMILES: Cc1nc(NC(=O)C(C)(C)Oc2ccc(F)cc2F)sc1C(=O)O] | 2-[2-(2,4-Difluoro-phenoxy)-2-methyl-propionylamino]-4-methyl-thiazole-5-carboxylic acid.<br>$^1$H NMR (400 MHz, CDCl$_3$): δ 1.52 (s, 6H), 2.6 (s, 3H), 6.98-7.08 (m, 2H), 7.33 (s, 1H), 12.6 (bs, 1H), 13.0 (bs, 1H).<br>MS (EI) m/z 356.9 (M + 1). |

| Example | Structure | IUPAC name and analytical data |
|---|---|---|
| B10 | 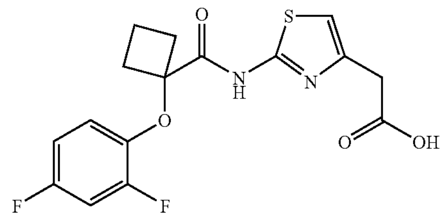 [SMILES: O=C(O)Cc1csc(NC(=O)C2(Oc3ccc(F)cc3F)CCC2)n1] | (2-{[1-(2,4-Difluoro-phenoxy)-cyclobutanecarbonyl]-amino}-thiazol-4-yl)-acetic acid.<br>$^1$H NMR (400 MHz, CDCl$_3$): δ 1.91-1.97 (m, 1H), 2.03-2.10 (m, 1H), 2.40-2.48 (m, 2H), 2.71-2.78 (m, 2H), 3.61 (s, 2H), 6.56-6.73 (m, 2H), 6.84 (s, 1H), 6.81-6.85 (m, 1H).<br>MS (EI) m/z: 369.00 (M + 1). |

Synthesis Type-C

Example C1

1-(4-Methanesulfonyl-phenoxy)-cyclohexanecarboxylic acid, thiazol-2-yl amide

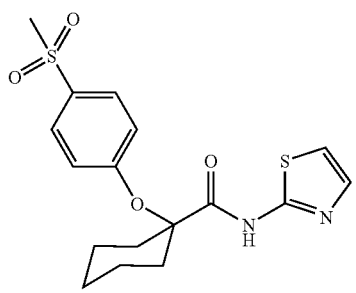 [SMILES: CS(=O)(=O)c1ccc(OC2(C(=O)Nc3nccs3)CCCCC2)cc1]

1-(4-Methanesulfonyl-phenoxy)-cyclohexanecarboxylic acid, thiazol-2-yl amide was prepared using the method described for Typical Example A. $^1$H NMR (400 MHz, CDCl$_3$): δ 1.58-2.20 (m, 10H), 3.05 (s, 3H), 6.90 (d, J=8.8 Hz, 2H), 7.11 (d, J=3.6 Hz, 1H), 7.50 (d, J=3.6 Hz, 1H), 7.85 (d, J=8.8 Hz, 2H), MS (EI) m/z 381.1 (M+1).

Precursor 1-(4-Chloro-phenoxy)-cyclohexanecarboxylic acid used for amide coupling was synthesised as follows:

1-(4-Chloro-phenoxy)-cyclohexanecarboxylic acid

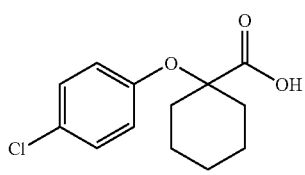 [SMILES: O=C(O)C1(Oc2ccc(Cl)cc2)CCCCC1]

To a suspension of NaOH (2.8 g, 70.02 mmol) in THF (10 ml) added 4-chloro phenol (1 g, 7.78 mmol) and stirred for 15 min at r.t. Reaction mixture was cooled to 0° C. Cyclohex-anone (7.62 g, 77.8 mmol) was added, followed by drop wise addition of anhydrous CHCl$_3$ (2.5 ml, 31.12 mmol) over a period of 15-20 min. The reaction mixture was stirred for 14-18 hr allowing the temperature to rise to room temperature. Reaction mixture was neutralized with (HCl, pH~7) and was extracted with EtOAc (3×50 mL). The organic phase were successively washed with 2% HCl (50 mL), brine (50 mL) and dried over Na$_2$SO$_4$. After evaporation of solvent, the residue was used as such for the next step.

Synthesis Type-D

Example D1

(2-{[1-(4-Methanesulfonyl-phenoxy)-cyclohexanecarbonyl]-amino}-thiazol-4-yl)-acetic acid

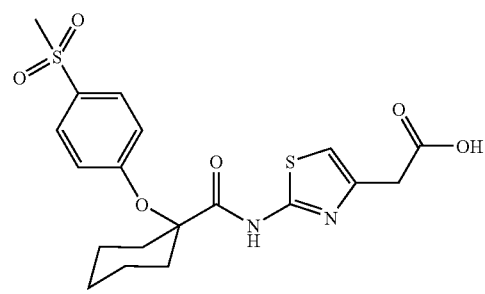 [SMILES: CS(=O)(=O)c1ccc(OC2(C(=O)Nc3nc(CC(=O)O)cs3)CCCCC2)cc1]

Ester hydrolysis of (2-{[1-(4-Methanesulfonyl-phenoxy)-cyclohexanecarbonyl]-amino}-thiazol-4-yl)-acetic acid ethyl ester gave (2-{[1-(4-Methanesulfonyl-phenoxy)-cyclohexanecarbonyl]-amino}-thiazol-4-yl)-acetic acid using Typical Example B.

$^1$H NMR (400 MHz, DMSOd$_6$): δ 1.23-1.62 (m, 6H), 1.90-1.97 (m, 2H), 2.18-2.21 (m, 2H) 3.25 (s, 3H), 3.60 (s, 2H), 7.00 (d, J=8.8 Hz, 2H) 7.05 (s, 1H), 7.85 (d, J=8.8 Hz, 2H), MS (EI) m/z 439 (M+1).

Synthesis Type-E

Example E1

2-Methyl-N-thiazol-2-yl-2-(3-trifluoromethyl-phenylamino)-propionamide

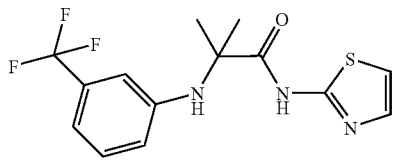 [SMILES: CC(C)(Nc1cccc(C(F)(F)F)c1)C(=O)Nc1nccs1]

3-Trifluoromethyl aniline (3 ml) and 2-Bromo-2-methyl-N-thiazol-2-yl-propionamide (0.1 g) were heated at 100° C. for 48 hrs. The residue was purified by flash chromatography (DCM:Methanol) to give amide (40 mg), $^1$H NMR (400 MHz, CDCl$_3$): δ 1.6 (s, 6H), 6.64 (d, J=8.0 Hz, 1H), 6.82 (s, 1H), 7.02 (d, J=3.2 Hz, 1H), 7.07 (d, J=8.0 Hz, 1H), 7.25-7.29 (m, 1H), 7.41 (d, J=3.2 Hz, 1H). MS (EI) m/z 330.1 (M+1).

Preparation of 2-Bromo-2-methyl-N-thiazol-2-yl-propionamide used in Example E1 is described below.

2-Bromo-2-methyl-N-thiazol-2-yl-propionamide

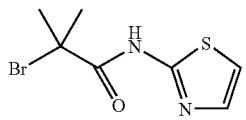

To a solution of 2-aminothiazole (0.5, 5 mmol) and triethyl amine (2.0 ml, 15 mmol) in DCM (10 ml) 2-Bromo-2-methyl-propionyl bromide (0.74 ml, 6 mmol) was added drop wise over a period of 10-15 min at −5° C. and stirred for 1 h. The reaction mixture was diluted with DCM (25 ml), washed with brine (2×5 ml), dried over Na$_2$SO$_4$. Solvent was evaporated under reduced pressure to yield 2-Bromo-2-methyl-N-thiazol-2-yl-propionamide (1.18 g, 95%) of product which was used as such for the next step.

Following compounds were prepared in an analogous manner of Example E1 from the appropriate intermediates

Synthesis Type-F

Example F1

2-Methyl-N-thiazol-2-yl-2-(4-thiophen-3-yl-phenoxy)-propionamide

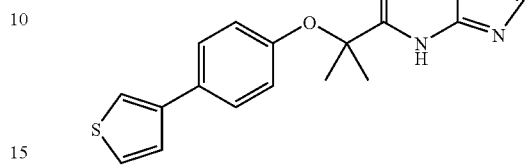

2-(4-Iodo-phenoxy)-2-methyl-N-thiazol-2-yl-propionamide (0.2 g, 0.51 mmol), thiophene-3-boronic acid (0.078 g, 0.61 mmol) were dissolved in anhydrous DMF (2 ml) and potassium carbonate (0.21 g, 1.53 mmol) added. Reaction mixture was flushed and [PPh$_3$]$_4$Pd (0) (0.058 g, 0.051 mmol) added, and reaction mixture was heated for 18 hours. Reaction mixture was poured in ice cold water (5 ml) extracted with ethyl acetate (3×10 ml), organic layer dried over Na$_2$SO$_4$. After evaporation, the residue was purified by preparative chromatography (1:5 EtOAc:Hexane) to give amide (0.035 g, 20%).

$^1$H NMR (400 MHz, CDCl$_3$): δ 1.6 (s, 6H), 6.98 (d, J=8.8 Hz, 2H), 7.03 (d, J=3.6 Hz, 1H0, 7.34-7.35 (m, 1H0, 7.38-7.40 (m, 2H), 7.49 (d, J=3.2 Hz, 1H), 7.52 (d, J=8.8, 2H); MS (EI) m/z: 345.1 (M+1).

Synthesis Type-G

Example G1

{2-[2-(2,4-Difluoro-phenoxy)-2-methyl-butyrylamino]-thiazol-4-yl}-acetic acid ethyl ester

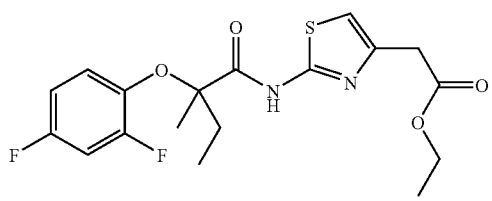 [SMILES: CCOC(=O)Cc1csc(NC(=O)C(C)(CC)Oc2ccc(F)cc2F)n1]

To a solution of 2-(2,4-Difluoro-phenoxy)-2-methyl-butyric acid (0.2 g, 0.87 mmol) in DCM (5 ml) added N-Methyl morpholine (0.6 ml, 5.2 mmol) and HOBt (0.2 g, 1.3 mmol) at

| Example | Structure | IUPAC name and analytical data |
|---------|-----------|-------------------------------|
| E2 | 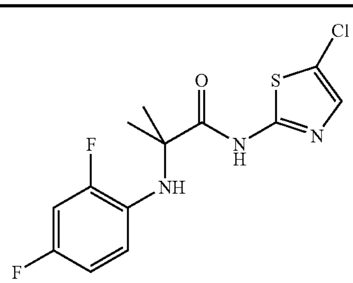 | N-(5-Chlorothiazol-2-yl)-2-(2,4-difluorophenylamino)-2-methyl-propionamide. $^1$H NMR (400 MHz, CDCl$_3$): δ 1.60 (s, 6H), 4.10 (s, 1H), 6.38-6.44 (m, 1H), 6.67-6.72 (m, 1H), 6.81-6.87 (m, 1H), 7.24 (s, 1H). MS (EI) m/z: 332 (M + 1). |

0° C. After stirring at this temperature for 5 min. added (2-Amino-thiazol-4-yl)-acetic acid ethyl ester (0.17 g, 0.92 mmol) and followed by EDCI (0.217 g, 1.3 mmol). The resulting solution was stirred for 12 h. then quenched with sat NH₄Cl solution (15 ml). The aqueous phase was extracted with CH₂Cl₂ (3×50 ml). The organic phase were successively washed with 2% HCl (50 ml), brine (50 ml) and dried over Na₂SO₄. After evaporation, the residue was purified by flash chromatography to give {2-[2-(2,4-Difluoro-phenoxy)-2-methyl-butyrylamino]-thiazol-4-yl}-acetic acid ethyl ester (0.2 g, 59%). $^1$H NMR (400 MHz, CDCl₃): 1.03 (t, J=7.2 Hz, 3H), 1.28 (t, J=7.6 Hz, 3H), 1.43 (s, 3H), 1.83-1.89 (m, 1H), 2.04-2.1 (m, 1H), 3.73 (s, 2H), 4.2 (q, J=6.8 Hz, 2H), 6.8-6.93 (m, 3H), 7.0-7.04 (m, 1H); MS (EI) m/z: 399 (M+1).

Preparation of 2-(2,4-Difluoro-phenoxy)-2-methyl-butyric acid ethyl este used in Example G1 is described below.

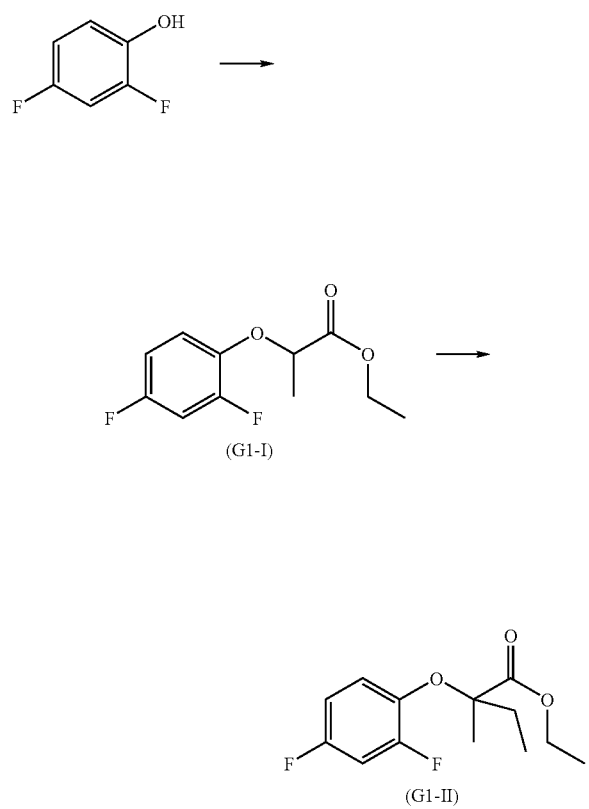

2-(2,4-Difluoro-phenoxy)-propionic acid ethyl ester (G1-I)

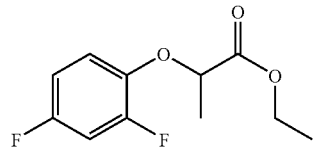

2-(2,4-Difluoro-phenoxy)-propionic acid ethyl ester was prepared by a similar procedure as the procedure of preparation of 2-(4-Chloro-phenoxy)-2-methyl-propionic acid ethyl ester (A1-I)

2-(2,4-Difluoro-phenoxy)-2-methyl-butyric acid ethyl ester (G1-II)

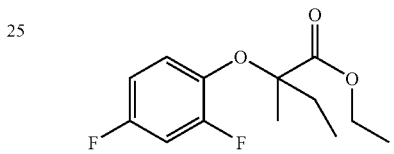

To a solution of 2-(2,4-Difluoro-phenoxy)-propionic acid ethyl ester (4 g, 17.4 mmol) in THF at −78° C. was added a solution of LiHMDS (1M, solution in Hexane, 20 ml, 19.1 mmol) drop wise over a period of 30 min. Ethyl iodide (1.82 ml, 2.2 mmol) was added drop wise at −78° followed by addition of Tetra butyl ammonium iodide (50 mg, catalytic amount). The reaction mixture was stirred at −78° C. for 1 hr and then at 20-25° C. for 3 hrs. The reaction mixture was quenched with saturated Ammonium Chloride (2×5 ml) and extracted with ethylacetate (2×100 ml). The organic layer was washed with brine (15 ml), dried over Na₂SO₄. The solvent was evaporated and the residue was purified by flash chromatography (1:40: EtOAC:hexanes) to give 2-(2,4-Difluoro-phenoxy)-2-methyl-butyric acid ethyl ester (2.69 g, 60%).

Following compounds were prepared in an analogous manner of Example G1 from the appropriate intermediates.

| Example | Structure | IUPAC name and analytical data |
|---|---|---|
| G2 | 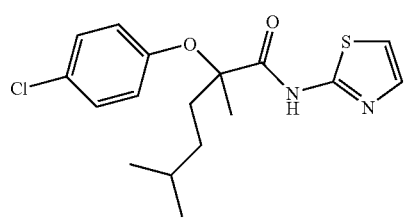 [SMILES: CC(C)CCC(C)(Oc1ccc(Cl)cc1)C(=O)Nc1nccs1] | 2-(4-Chloro-phenoxy)-2,5-dimethyl-hexanoic acid thiazol-2-ylamide. $^1$H NMR (400 MHz, CDCl₃): δ 0.878 (d, J = 6.4 Hz, 6H), 1.412-1.577 (m, 1H), 1.51 (s, 3H), 1.52-1.57 (m, 2H), 1.81-1.88 (m, 1H), 1.98-2.06 (m, 1H), 6.91 (d, J = 8.8 Hz, 2H), 7.04 (d, J = 3.6 Hz, 1H), 7.24 (d, J = 8.8 Hz, 2H), 7.49 (d, J = 3.6 Hz, 1H), 10-11 (bs, 1H). MS (EI) m/z: 353.1 (M + 1) |

| Example | Structure | IUPAC name and analytical data |
|---|---|---|
| G3 | 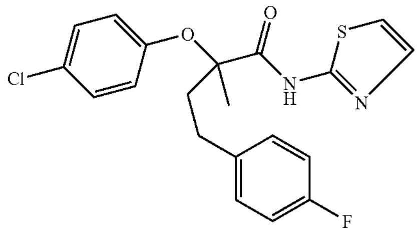 [SMILES: CC(CCc1ccc(F)cc1)(Oc1ccc(Cl)cc1)C(=O)Nc1nccs1] | 2-(4-Chloro-phenoxy)-4-(4-fluoro-phenyl)-2-methyl-N-thiazol-2-yl-butyramide.<br>$^1$H NMR (400 MHz, CDCl$_3$): δ 1.6 (s, 3H), 2.09-2.17 (m, 1H), 2.32-2.4 (m, 1H), 2.59-2.67 (m, 1H), 2.81-2.88 (m, 1H), 6.91-6.96 (m, 4H), 7.05 (d, J = 3.6 Hz, 1H), 7.07-7.11 (m, 2H), 7.26-7.29 (m, 2H), 7.48 (d, J = 3.6 Hz, 1H), 10.6 (s, 1H).<br>MS (EI) m/z: 405.1 (M + 1). |
| G4 | 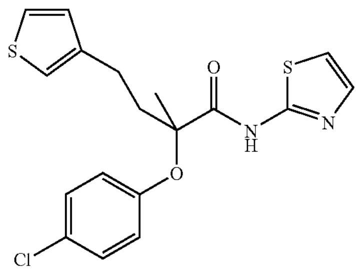 [SMILES: CC(CCc1ccsc1)(Oc1ccc(Cl)cc1)C(=O)Nc1nccs1] | 2-(4-Chloro-phenoxy)-2-methyl-N-thiazol-2-yl-4-thiophen-3-yl-butyramide.<br>$^1$H NMR (400 MHz, CDCl$_3$): δ 1.39 (s, 3H), 2.18-2.26 (m, 1H); 2.43-2.50 (m, 1H), 2.85-2.93 (m, 1H), 3.10-3.18 (m, 1H), 6.79 (d, J = 3.2 Hz, 1H), 6.90 (dd, J = 3.6 Hz, 5.2 Hz, 1H), 6.95 (d, J = 8.8 Hz, 2H), 7.05 (d, J = 3.6 Hz, 1H), 7.12-7.13 (m, 1H), 7.29 (d, J = 8.8 Hz, 2H), 7.5 (d, J = 3.6 Hz, 1H), 10.1 (s, 1H).<br>MS (EI) m/z: 393.1 (M + 1). |
| G5 | 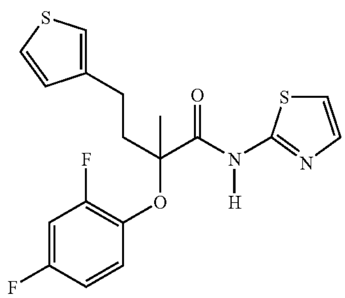 [SMILES: CC(CCc1ccsc1)(Oc1ccc(F)cc1F)C(=O)Nc1nccs1] | 2-(2,4-Difluoro-phenoxy)-2-methyl-N-thiazol-2-yl-4-thiophen-3 -yl-butyramide.<br>$^1$H NMR (400 MHz, CDCl$_3$): δ 1.60 (s, 3H), 2.12-2.18 (m, 1H); 2.40-2.48 (m, 1H), 2.69-2.74 (m, 1H), 2.97-3.0 (m, 1H), 6.84-6.86 (m, 1H), 6.91-6.93 (m, 2H), 6.94-6.96 (m, 1H), 7.01-7.07 (m, 2H), 7.24-7.26 (m, 1H), 7.51 (d, J = 3.6 Hz, 1H), 10.24 (s, 1H).<br>MS (EI) m/z: 395 (M + 1). |
| G6 | 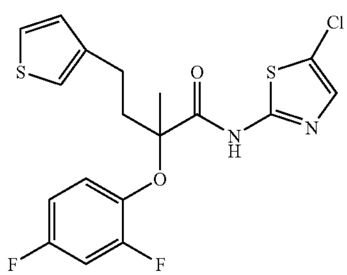 [SMILES: CC(CCc1ccsc1)(Oc1ccc(F)cc1F)C(=O)Nc1ncc(Cl)s1] | N-(5-Chloro-thiazol-2-yl)2-(2,4-difluoro-phenoxy)2-methyl-4-thiaphen-3-yl-butyl amide<br>$^1$H NMR (400 MHz, CDCl$_3$): δ 1.47 (s, 3H), 2.17 (dt, J = 3.6, 11.2 Hz, 1H), 2.47 (dt, J = 5.2, 13.2 Hz, 1H), 2.87 (dt, J = 5.2, 14.8 Hz, 1H), 3.18 (dt, J = 4.0, 15.6 Hz, 1H), 6.81-7.05 (m, 4H), 7.12 (d, J = 5.2 Hz, 1H), 7.32 (s, 1H), 10.13 (s, br, 1H)<br>MS (EI) m/z: 429 (M + 1). |
| G7 | 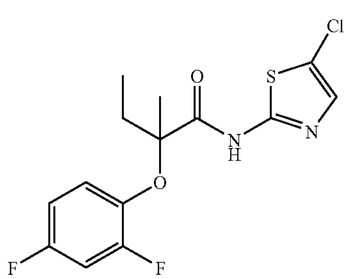 [SMILES: CCC(C)(Oc1ccc(F)cc1F)C(=O)Nc1ncc(Cl)s1] | N-(5-Chloro-thiazol-2-yl)-2-(2,4-difluoro-phenoxy)-2-methyl-butyramide.<br>$^1$H NMR (400 MHz, CDCl$_3$): δ 1.03 (t, J = 7.6 Hz, 3H), 1.43 (s, 3H), 1.84-1.89 (m, 1H), 2.03-2.13 (m, 1H), 6.83 (m, 1H), 6.92 (m, 1H), 7.02-7.04 (m, 1H), 7.32 (s, 1H), 10.1 (s, 1H).<br>MS (EI) m/z: 348.00 (M + 1). |
| G8 | 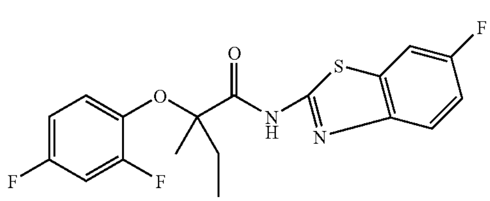 [SMILES: CCC(C)(Oc1ccc(F)cc1F)C(=O)Nc1nc2ccc(F)cc2s1] | 2-(2,4-Difluoro-phenoxy)-N-(6-fluoro-benzothiazol-2-yl)-2-methyl-butyramide.<br>$^1$H NMR (400 MHz, CDCl$_3$): 1.08 (t, J = 7.6 Hz, 3H), 1.48 (s, 3H), 1.89-1.95 (m, 1H), 2..09-2.14 (m, 1H), 6.84-6.89 (m, 1H), 6.92-6.97 (m, 1H), 7.04-7.09 (m, 1H), 7.18-7.23 (m, 1H), 7.56 (dd, J = 8 Hz, 2.4 Hz, 1H), 7.75-7.78 (m, 1H), 10.21 (s, 1H)<br>MS (EI) m/z: 381.00 (M + 1). |

| Example | Structure | IUPAC name and analytical data |
|---|---|---|
| G9 | 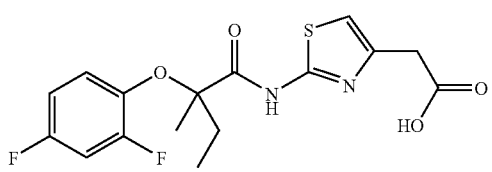 | 2-(2,4-Difluoro-phenoxy)-N-(5-fluoro-thiazol-2-yl)-2-methyl-butyramide. <br> $^1$H NMR (400 MHz, CDCl$_3$): 1.04 (t, J = 7.6 Hz, 3H), 1.42 (s, 3H), 1.84-1.89 (m, 1H), 2.04-2.08 (m, 1H), 6.81-6.86 (m, 1H), 6.89-6.95 (m, 1H), 7.00-7.08 (m, 1H), 9.83 (s, 1H). <br> MS (EI) m/z: 331.00 (M + 1). |
| G10 | 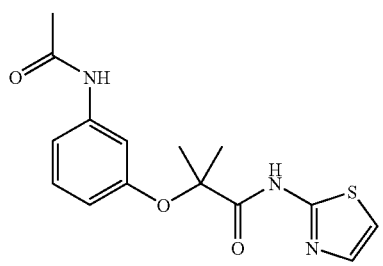 | 2-(2,4-Difluoro-phenoxy)-2-methyl-N-(4-phenyl-thiazol-2-yl)-butyramide. <br> 1H NMR (DMSO): 1.07 (t, J = 7.2 Hz, 3H), 1.46 (s, 3H), 1.87-1.92 (m, 1H), 2.08-2.13 (m, 1H), 6.83 6.84 (m, 1H), 6.92-6.93 (m, 1H), 7.04-7.07 (m, 1H), 7.19 (s, 1H), 7.31-7.35 (m, 1H), 7.42 (dd, J = 7.6 Hz, 2H), 7.85 (d, J = 7.6 Hz, 2H), 10.17 (s, 1H). <br> MS (EI) m/z: 389.00 (M + 1). |

Synthesis Type-H

Example H1

{2-[2-(2,4-Difluoro-phenoxy)-2-methyl-butyrylamino]-thiazol-4-yl}-acetic acid

To a solution of {2-[2-(2,4-Difluoro-phenoxy)-2-methyl-butyrylamino]-thiazol-4-yl}-acetic acid ethyl ester (0.202 g, 0.51 mmol) in MeOH (3 ml) and water (1.5 ml). NaOH (0.041 g, 1.1 mmol) was added and stirred at room temperature for 16 hrs. The organic solvent was evaporated and residue was diluted with water (2 ml) and acidified (pH~2) with 5% HCl. The aqueous layer was extracted with ethyl acetate (2×10 ml) and organic layer was washed with saturated brine (10 ml). The organic layer was dried over Na$_2$SO$_4$ and evaporated under reduced pressure to obtain crude product which was solidified by triturating with hexane to afford {2-[2-(2,4-Difluoro-phenoxy)-2-methyl-butyrylamino]-thiazol-4-yl}-acetic acid (0.158 g, 84%). $^1$H NMR (400 MHz, CDCl$_3$): δ1.03 (t, J=7.6 Hz, 3H), 1.44 (s, 3H), 1.86-1.9 (m, 1H), 2.05-2.09 (m, 1H), 3.78 (s, 2H), 6.78 (s, 1H), 6.80-6.84 (m, 1H), 6.88-6.93 (m, 1H), 7.0-7.06 (m, 1H), 10.6 (s, 1H), MS (EI) m/z: 371.00 (M+1) and mp: 148-149° C.

Synthesis Type-I

Example I1

2-(3-Acetylamino-phenoxy)-2-methyl-N-thiazol-2-yl-propionamide

To a solution of 2-(3-Acetylamino-phenoxy)-2-methyl-propionic acid (0.11 g, mmol) in DCM (6 ml) was added TEA (0.07 ml, 0.55 mmol) and HOBt (0.085 g, 0.55 mmol) at 0° C. After stirring at this temperature for 5 min. added 2-aminothiazole and followed by EDCI (0.1 g, 0.55 mmol). The resulting solution was stirred for 12 h. then quenched with sat NH$_4$Cl solution (15 ml). The aqueous phase was extracted with CH$_2$Cl$_2$ (3×50 ml). The organic phase was successively washed with 2% HCl (50 ml), brine (50 ml) and dried over Na$_2$SO$_4$. After evaporation, the residue was purified by flash chromatography (DCM:MeOH) to give amide (0.089 g, mmol, 60%). $^1$H NMR (400 MHz, CDCl$_3$): 1.62 (s, 6H), 2.17 (s, 3H), 6.67 (d, J=7.6 Hz, 1H), 7.02 (d, J=3.6 Hz, 1H), 7.17-7.26 (m, 1H), 7.48 (d, J=3.6 Hz, 1H), 10.18 (brs, 1H). MS (EI) m/z: 320.1 (M+1).

Preparation of 2-(3-Acetylaminophenoxy)-2-methylpropionic acid used in Example I1 is described below.

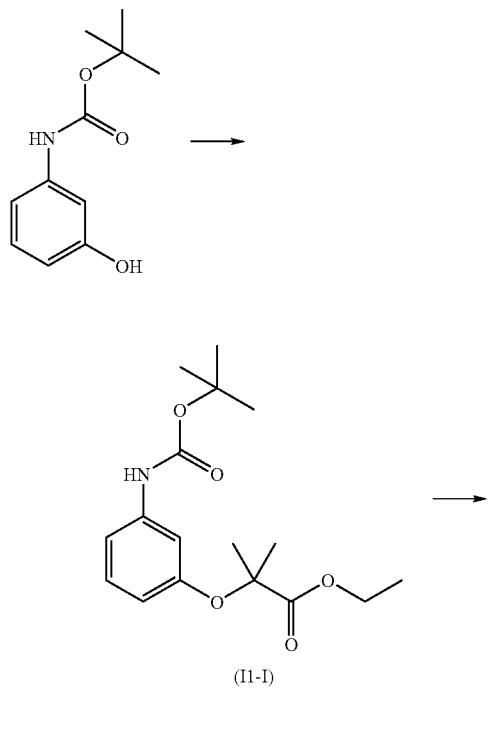

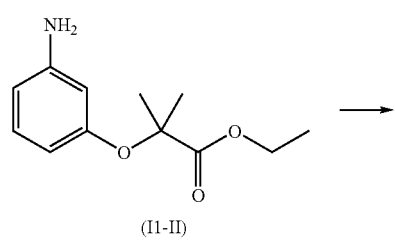

(I1-II)

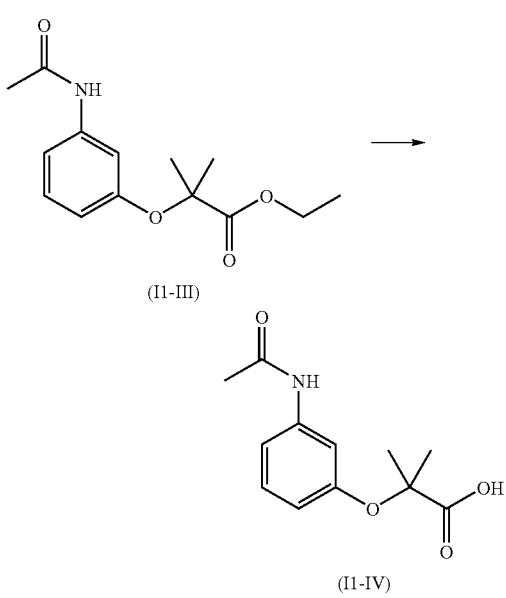

2-(3-tert-Butoxycarbonylamino-phenoxy)-2-methyl-propionic acid ethyl ester (I1-I)

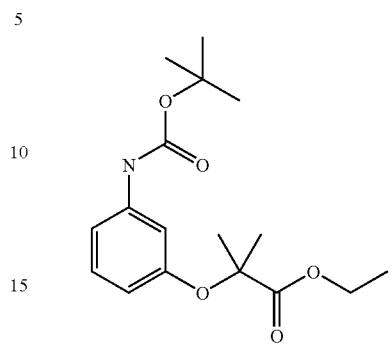

To a solution of (3-Hydroxy-phenyl)-carbamic acid tert-butyl ester (2.4 g, 11.4 mmol) in 5 ml of dry DMF, anhydrous potassium carbonate (7.9 g, 57.416 mmol) was added. The mixture stirred for 5-10 minutes, added ethyl-2-bromo-isobutyrate (4.5 g, 22.9 mmol). The resulting mixture was heated at 70° C. for 12 hours. Upon completion (~25 h), the solution was diluted with EtOAc (25 ml) and washed with saturated NH$_4$Cl (5 ml). The aqueous layer was then extracted for two additional times with EtOAc (10 ml) and the combined organic fractions were washed with brine (2×5 ml). The solution was then dried over Na$_2$SO$_4$ and concentrated to give brown oil. Purification on silica gel (hexanes/acetone) yielded 1.8 g (49%). $^1$H-NMR (400 MHz, CDCl$_3$): δ $^1$H NMR (400 MHz, CDCl$_3$): 1.26 (t, J=7.2 Hz, 3H), 1.50 (s, 9H), 1.59 (s, 6H), 6.43 (s, 1H), 6.47-6.50 (m, 1H), 6.96 (t, J=8.4 Hz, 2H), 7.11 (t, J=8.0, 1H).

2-(3-Amino-phenoxy)-2-methyl-propionic acid ethyl ester (I1-II)

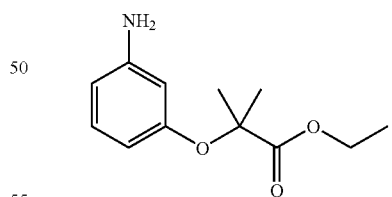

To a solution of 2-(3-tert-Butoxycarbonylamino-phenoxy)-2-methyl-propionic acid ethyl ester (0.8 g, 2.4 mmol) in DCM (10 ml) at 0° C. was added TFA (10 ml) and stirred at 0° C. for 100 min. The solvent was removed under reduced pressure; residue was dissolved in DCM and treated with 2.5M solution of NaOH. The organic layer was separated and dried over Na$_2$SO$_4$, concentrated to yield 2-(3-amino-phenoxy)-2-methyl-propionic acid ethyl ester (0.5 g, mmol, 98%). $^1$H NMR (400 MHz, CDCl$_3$): 1.25 (t, J=7.2 Hz, 3H), 1.56 (s, 6H), 3.62 (brs, 2H), 4.23 (q, J=7.2 Hz, 2H), 6.21-6.22 (m, 2H), 6.32 (d, J=7.2 Hz, 1H), 6.99 (t, J=8.4 Hz, 1H).

2-(3-Acetylamino-phenoxy)-2-methyl-propionic acid ethyl ester (I1-III)

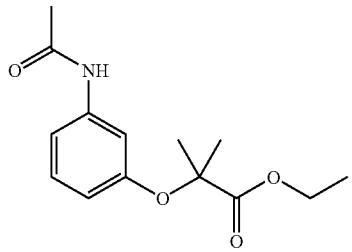 [SMILES: CCOC(=O)C(C)(C)Oc1cccc(NC(C)=O)c1]

To a solution of 2-(3-Amino-phenoxy)-2-methyl-propionic acid ethyl ester (0.54 g, 2.42 mmol) in DCM (5 ml) at 0° C. was added pyridine (0.23 ml, 2.9 mmol). The reaction mixture was cooled to 0° C. and a solution of acetyl chloride (0.21 ml, 2.9 mmol) in DCM (4 ml) was added drop wise over 5 min. The reaction mixture was stirred at r.t. for 18 hrs, quenched with water (10 ml) and extracted in DCM (2×20 ml). The organic layer was dried over Na₂SO₄ and concentrated to afford the crude oil (0.64 g) which was used for the next step without purification.

2-(3-Acetylamino-phenoxy)-2-methyl-propionic acid (I1-IV)

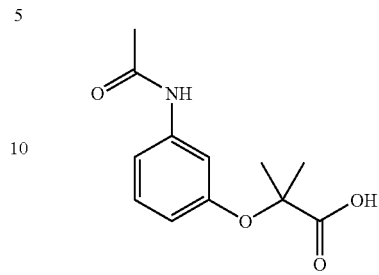

2-(3-Acetylamino-phenoxy)-2-methyl-propionic acid ethyl ester (0.6 g, 2.2 mmol) was dissolved in THF (20 ml) and a solution of lithium hydroxide (0.33 g, 7.9 mmol) in water (5.8 ml) was added. The reaction mixture was allowed to stir at RT for 24 h. The solvent was removed under reduced pressure and the aqueous layer was extracted with EtOAc (10 ml). Aqueous layer was basified (pH~5) with 1 N HCl at 0° C., extracted in EtOAc (2×50 ml) dried over Na₂SO₄ and concentrated under reduced pressure to afford the acid (0.45 g, 85%). ¹H NMR (400 MHz, CDCl₃): 1.61 (s, 6H), 2.11 (d, J=6.4 Hz, 3H), 4.65 (brs, 3H), 6.68 (d, J=8.0 Hz, 1H), 7.07 (d, J=8.0 Hz, 1H), 7.17 (t, J=8.0 Hz, 1H), 7.29 (s, 1H), 7.60 (s, 1H); MS (EI) m/z: 238.1 (M+1).

Following compounds were prepared in an analogous manner of Typical Example I1 from the appropriate intermediates

| Sr. No. | Structure | IUPAC name and analytical data |
|---|---|---|
| I2 | 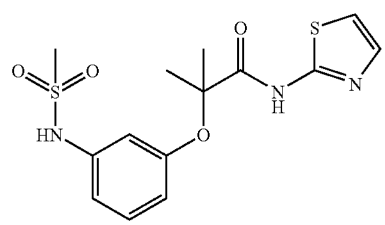 [SMILES: CC(C)(Oc1cccc(NS(C)(=O)=O)c1)C(=O)Nc1nccs1] | 2-(3-Methanesulfonylamino-phenoxy)-2-methyl-N-thiazol-2-yl-propionamide. ¹H NMR (400 MHz, CDCl₃): δ 1.64 (s, 6H), 2.95 (s, 3H), 6.67 (dd, J = 2 Hz, 8 Hz, 1H), 6.84 (t, J = 2 Hz, 1H), 6.89-6.92 (m, 1H), 7.01 (d, J = 3.6 Hz, 1H), 7.20 (t, J = 8 Hz, 1H), 7.52 (d, J = 3.6 Hz, 2H), 10.75 (bs, 1H) MS (EI) m/z: 356.1 (M + 1). |
| I3 | 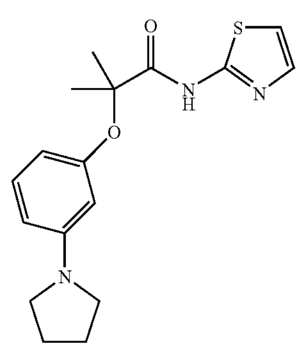 [SMILES: CC(C)(Oc1cccc(N2CCCC2)c1)C(=O)Nc1nccs1] | 2-Methyl-2-(3-pyrrolidin-1-yl-phenoxy)-N-thiazol-2-yl-propionamide ¹H NMR (400 MHz, CDCl₃): δ 1.62 (s, 6H), 1.99 (m, 4H), 3.24 (m, 4H), 6.14 (t, J = 2 Hz, 1H), 6.24 (dd, J = 2 Hz, 8 Hz, 1H), 6.32 (dd, J = 2 Hz, 8 Hz, 1H), 7.02 (d, J = 3.6 Hz, 1H), 6.14 (t, J = 8 Hz, 1H), 7.48 (d, J = 3.6 Hz, 1H), 10.20 (bs, 1H). MS (EI) m/z: 332.2 (M + 1). |

| Sr. No. | Structure | IUPAC name and analytical data |
|---|---|---|
| I4 | 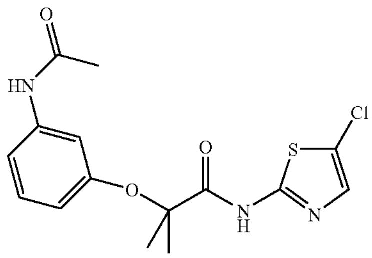 [SMILES: CC(=O)Nc1cccc(OC(C)(C)C(=O)Nc2ncc(Cl)s2)c1] | 2-(3-Acetylamino-phenoxy)-N-(5-chloro-thiazol-2-yl)-2-methyl-propionamide.<br>$^1$H NMR (400 MHz, CDCl$_3$): δ 1.60 (s, 6H), 2.10 (s, 3H), 6.66 (d, J = 8.0 Hz, 1H), 7.14-7.30 (m, 5H), 10.10 (bs, 1H).<br>MS (EI) m/z: 354.0 (M + 1). |
| I5 | 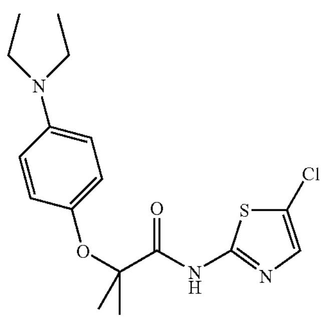 [SMILES: CCN(CC)c1ccc(OC(C)(C)C(=O)Nc2ncc(Cl)s2)cc1] | N-(5-Chloro-thiazol-2-yl)-2-(4-diethylamino-phenoxy)-2-methyl-propionamide.<br>$^1$H NMR (400 MHz, CDCl$_3$): δ 1.14 (t, J = 7.2 Hz, 6H), 1.51 (s, 6 H), 3.31 (q, J = 7.2 Hz, 4H), 6.58 (d, J = 9.2 Hz, 2H), 6.83 (d, J = 8.8 Hz, 2H), 7.30 (s, 1H), 10.10 (bs, 1H).<br>MS (EI) m/z: 368.0 (M + 1). |

2-(4-Isopropylamino-phenoxy)-2-methyl-N-thiazol-2-yl-propionamide

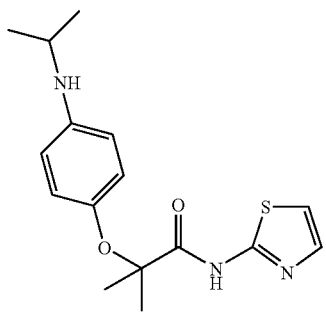 [SMILES: CC(C)Nc1ccc(OC(C)(C)C(=O)Nc2nccs2)cc1]

Amide formation was done by the procedure used in Example A1

$^1$H NMR (400 MHz, CDCl$_3$): δ 1.21 (d, J=6.4 Hz, 6H), 1.52 (s, 6H), 3.38 (bs, 1H), 3.57 (m, 1H), 6.50 (d, J=8.8 Hz, 2H), 6.81 (d, J=8.8 Hz, 2H), 7.02 (d, J=3.5 Hz, 1H), 7.49 (d, J=6.3 Hz, 1H), 10.2 (bs, 1H), MS (EI) m/z: 320.2 (M+1).

Preparation of 2-(3-Isopropylamino-phenoxy)-2-methyl-propionic acid ethyl ester use for the synthesis of 2-(4-Isopropylamino-phenoxy)-2-methyl-N-thiazol-2-yl-propionamide is described below.

2-(3-Isopropylamino-phenoxy)-2-methyl-propionic acid ethyl ester

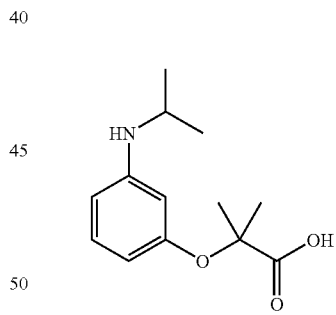

To a solution of 2-(3-Amino-phenoxy)-2-methyl-propionic acid ethyl ester (0.2 g, 0.89 mmol) in 1,2-dichloroethane (3 ml) acetone (6.6 ml, 89.6 mmol) and acetic acid (0.053 g, 0.89 mmol) were added. The reaction mixture was cooled to 0° C. Sodium triacetoxyborohydride (0.266 g, 1.25 mmol) was added and stirred at r.t. for 24 h. The reaction mixture was quenched with saturated NaHCO$_3$ and extracted in DCM (20 ml), washed with brine, dried over Na$_2$SO$_4$ and concentrated under reduced pressure to obtain crude product. Purification on silica gel (MeOH:CHCl$_3$) yielded 0.14 g (60%) of 2-(3-Isopropylamino-phenoxy)-2-methyl-propionic acid ethyl ester which was hydrolyzed using a typical procedure A1 and used as such for the next step.

2-[4-(2,5-Dimethyl-pyrrol-1-yl)-phenoxy]-2-methyl-N-thiazol-2-yl-propionamide

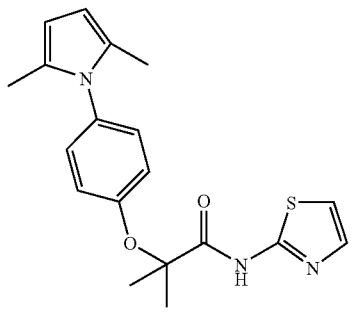 [SMILES: Cc1ccc(C)n1-c1ccc(OC(C)(C)C(=O)Nc2nccs2)cc1]

2-[4-(2,5-Dimethyl-pyrrol-1-yl)-phenoxy]-2-methyl-N-thiazol-2-yl-propionamide was prepared using the procedure of Example A1.

$^1$H NMR (400 MHz, CDCl$_3$): δ 1.66 (s, 6H), 2.02 (s, 6H), 5.89 (bs, 2H), 7.01-7.05 (m, 3H), 7.14 (d, J=8.8 Hz, 2H), 7.50 (d, J=3.6 Hz, 1H), 10.05 (bs, 11-1), MS (EI) m/z: 356.2 (M+1).

Preparation of 2-[3-(2,5-Dimethyl-pyrrol-1-yl)-phenoxy]-2-methyl-propionic acid ethyl ester used to synthesized 2-[4-(2,5-Dimethyl-pyrrol-1-yl)-phenoxy]-2-methyl-N-thiazol-2-yl-propionamide is described below.

2-[3-(2,5-Dimethyl-pyrrol-1-yl)-phenoxy]-2-methyl-propionic acid ethyl ester

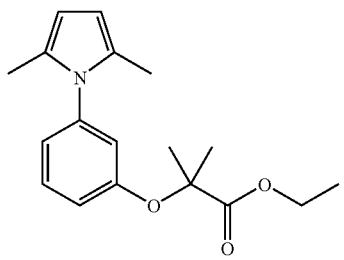 [SMILES: CCOC(=O)C(C)(C)Oc1cccc(-n2c(C)ccc2C)c1]

2-(3-Amino-phenoxy)-2-methyl-propionic acid ethyl ester (0.52 g, 2.36 mmol) was dissolved in Toluene (2 ml) and acetylacetone (0.53 m, 4.4 mmol) was added to the solution. The resulting mixture was refluxed for 6 h with a Dean-Stack apparatus. The reaction mixture was cooled to room temperature and concentrated under reduced pressure. The crude material thus obtained was purified by flash column affording 2-[3-(2,5-Dimethyl-pyrrol-1-yl)-phenoxy]-2-methyl-propionic acid ethyl ester (0.5 g, 71%). $^1$H NMR (400 MHz, CDCl$_3$): 1.): 1.24 (t, J=7.2 Hz, 3H), 1.57 (s, 6H), 2.02 (s, 6H), 4.23 (q, J=7.2 Hz, 2H), 5.88 (s, 2H), 6.71 (s, 1H), 6.83-6.91 (m, 2H), 7.26-7.33 (m, 1H); MS (EI) m/z: 302 (M+1).

Synthesis Type-J

Example J1

2-(2,4-Difluoro-phenoxy)-N-{4-[(4-fluoro-phenylcarbamoyl)-methyl]-thiazol-2-yl}-2-methyl-propionamide

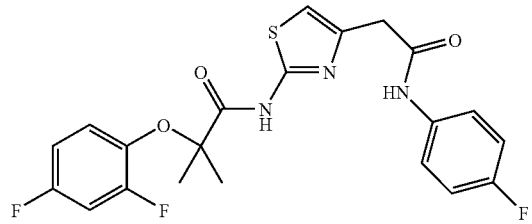 [SMILES: CC(C)(Oc1ccc(F)cc1F)C(=O)Nc1nc(CC(=O)Nc2ccc(F)cc2)cs1]

To a solution of {2-[2-(2,4-Difluoro-phenoxy)-2-methyl-propionylamino]-thiazol-4-yl}-acetic acid (0.15 g, 0.42 mmol) and HOBt (0.067 g, 0.5 mmol) in DCM, added 4-F-aniline (0.048 ml, 0.50 mml) and triethylamine (0.069 ml, 0.5 mmol). The resulting mixture stirred at 25° C. for 30 min. EDCI (0.099 g, 0.5 mmol) was added at 0° C. and the reaction mixture stirred at 25° C. for 18 hrs. The reaction mixture was quenched with water (2 ml), then extracted in DCM (20 ml), washed with brine (5 ml), dried over Na$_2$SO$_4$ and concentrated under reduced pressure to obtain the crude product. Purification on silica gel to yield 2-(2,4-Difluoro-phenoxy)-N-{4-[(4-fluoro-phenylcarbamoyl)-methyl]-thiazol-2-yl}-2-methyl-propionamide (0.14 g, 74%). $^1$H NMR (400 MHz, CDCl$_3$): δ 1.6 (s, 6H), 3.80 (s, 2H), 6.84-6.91 (m, 2H), 6.92-7.04 (m, 3H), 7.06-7.14 (m, 1H), 7.45-7.49 (m, 2H). MS (EI) m/z 450.1 (M+1).

Following compounds were prepared in an analogous manner of Example J1 from the appropriate intermediates

| Example | Structure | IUPAC name and analytical data |
|---------|-----------|--------------------------------|
| J2 | 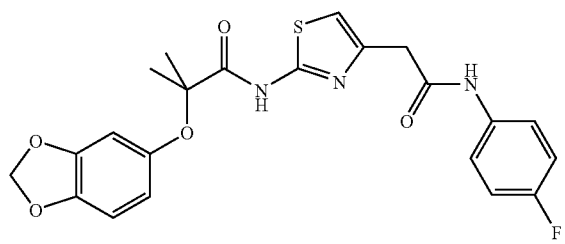 [SMILES: CC(C)(Oc1ccc2c(c1)OCO2)C(=O)Nc1nc(CC(=O)Nc2ccc(F)cc2)cs1] | 2-(Benzo[1,3]dioxol-5-yloxy)-N-{4-[(4-fluoro-phenylcarbamoyl)-methyl]-thiazol-2-yl}-2-methyl-propionamide. $^1$H NMR (400 MHz, CDCl$_3$): δ 1.6 (s, 6H), 3.80 (s, 2H), 6.00 (s, 2H), 6.46 (dd, J = 8.4 Hz, 1H), 6.55 (d, J = 2.4 Hz, 1H), 6.73 (d, J = 8.4 Hz, 1H), 6.87 (s, 1H), 6.99 (t, 2H), 7.45-7.49 (m, 2H). MS (EI) m/z 458.1 (M + 1). |

| Example | Structure | IUPAC name and analytical data |
|---|---|---|
| J3 | 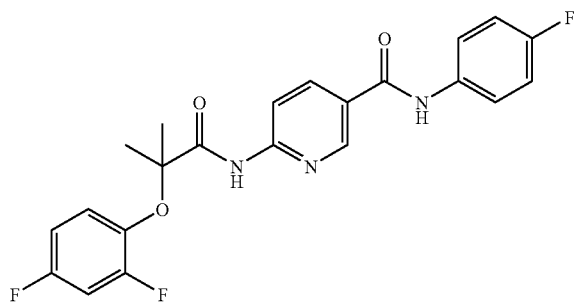 [SMILES: CC(C)(Oc1ccc(F)cc1F)C(=O)Nc1ccc(C(=O)Nc2ccc(F)cc2)cn1] | 6-[2-(2,4-Difluoro-phenoxy)-2-methyl-propionylamino]-N-(4-fluoro-phenyl)-nicotinamide<br>$^1$H NMR (400 MHz, CDCl$_3$): δ 1.6 (s, 6H), 6.82-6.86 (m, 1H), 6.90-6.95 (m, 1H), 7.05-7.11 (m, 3H), 7.58-7.62 (m, 2H), 7.74 (s, 1H), 8.22 (dd, J = 8.8 Hz, 1H), 8.42 (d, J = 8.8 Hz, 1H), 8.90 (bs, 1H), 9.6 (bs, 1H).<br>MS (EI) m/z: 430 (M + 1). |
| J4 | 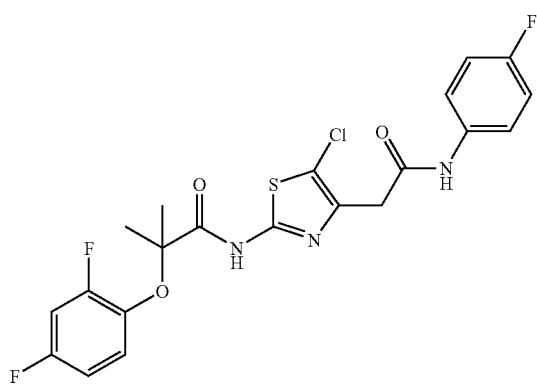 [SMILES: CC(C)(Oc1ccc(F)cc1F)C(=O)Nc1nc(CC(=O)Nc2ccc(F)cc2)c(Cl)s1] | N-{5-Chloro-4-[(4-fluoro-phenylcarbamoyl)-methyl]-thiazol-2-yl}-2-(2,4-difluoro-phenoxy)-2-methyl-propionamide.<br>$^1$H NMR (400 MHz, CDCl$_3$): δ 1.6 (s, 6H), 3.80 (s, 2H), 6.84-6.88 (m, 1H), 6.91-6.97 (m, 1H), 6.98-7.02 (m, 2H), 7.05-7.11 (m, 1H), 7.45-7.49 (m, 2H).<br>MS (EI) m/z: 484 (M + 1). |
| J5 | 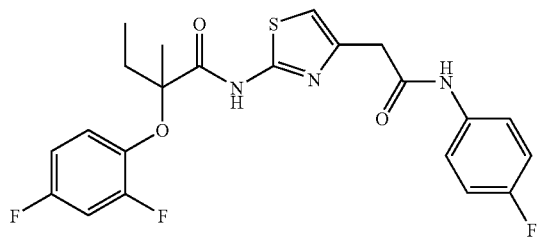 [SMILES: CCC(C)(Oc1ccc(F)cc1F)C(=O)Nc1nc(CC(=O)Nc2ccc(F)cc2)cs1] | 2-(2,4-Difluoro-phenoxy)-N-{4-[(4-fluoro-phenylcarbamoyl)-methyl]-thiazol-2-yl}-2-methyl-butyramide.<br>$^1$H NMR (400 MHz, CDCl$_3$): 1.06 (t, J = 7.6 Hz, 3H), 1.46 (s, 3H), 1.88-1.93 (m, 1H), 2.10-2.16 (m, 1H), 3.76 (s, 2H), 6.61-6.64 (m, 2H); 6.83-6.88 (m, 1H), 6.92-7.04 (m, 2H), 7.06-7.10 (m, 1H), 7.46-7.49 (m, 2H), 8.61 (s, 1H), 10.17 (s, 1H).<br>MS (EI) m/z: 464.10 (M + 1). |
| J6 | 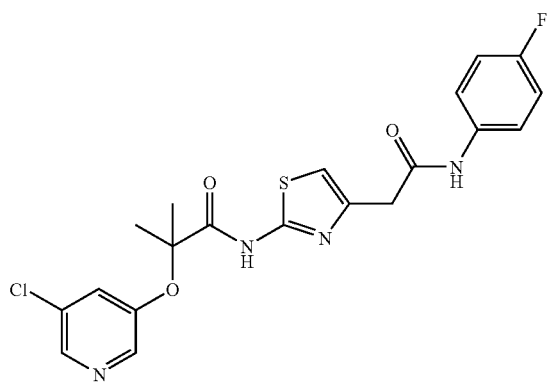 [SMILES: CC(C)(Oc1cncc(Cl)c1)C(=O)Nc1nc(CC(=O)Nc2ccc(F)cc2)cs1] | 2-(5-Chloro-pyridin-3-yloxy)-N-{4-[(4-fluoro-phenylcarbamoyl)-methyl]-thiazol-2-yl}-2-methyl-propionamide.<br>$^1$H NMR (400 MHz, CDCl$_3$): δ 1.62 (s, 6H), 3.76 (s, 2H), 6.89 (s, 1H), 6.99 (t, J = 8.4 Hz, 2H), 7.37 (s, 1H), 7.41-7.44 (m, 2H), 8.25-8.28 (m, 2H), 8.42 (bs, 1H), 9.9 (bs, 1H).<br>MS (EI) m/z 449 (M + 1). |

-continued

| Example | Structure | IUPAC name and analytical data |
|---|---|---|
| J7 | 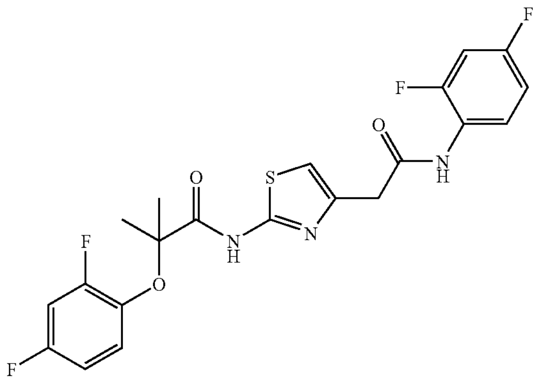 [SMILES: CC(C)(Oc1ccc(F)cc1F)C(=O)Nc1nc(CC(=O)Nc2ccc(F)cc2F)cs1] | 2-(2,4-Difluoro-phenoxy)-N-{4-[(2,4-difluoro-phenylcarbamoyl)-methyl]-thiazol-2-yl}-2-methyl-propionamide.<br>$^1$H NMR (400 MHz, CDCl$_3$): δ 1.6 (s, 6H), 3.81 (s, 2H), 6.80-6.86 (m, 4H), 6.92-6.97 (m, 1H), 7.07-7.12 (m, 1H), 8.25-8.31 (m, 1H).<br>MS (EI) m/z 468.1 (M + 1). |
| J8 | 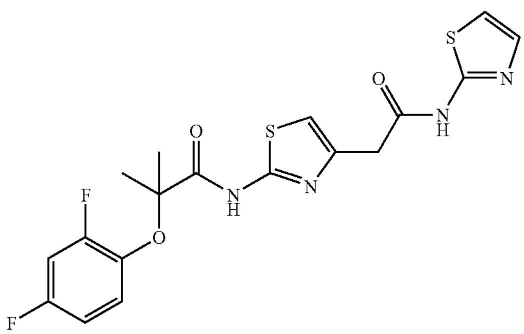 [SMILES: CC(C)(Oc1ccc(F)cc1F)C(=O)Nc1nc(CC(=O)Nc2nccs2)cs1] | 2-(2,4-Difluoro-phenoxy)-2-methyl-N-[4-(thiazol-2-ylcarbamoylmethyl)-thiazol-2-yl]-propionamide.<br>$^1$H NMR (400 MHz, CDCl$_3$): δ 1.6 (s, 6H), 3.94 (s, 2H), 6.83-6.86 (m, 2H), 6.90-7.01 (m, 1H), 7.02 (d, J = 3.6 Hz, 1H), 7.16-7.40 (m, 1H), 7.45 (d, J = 3.6 Hz, 1H).<br>MS (EI) m/z 439 (M + 1). |
| J9 | 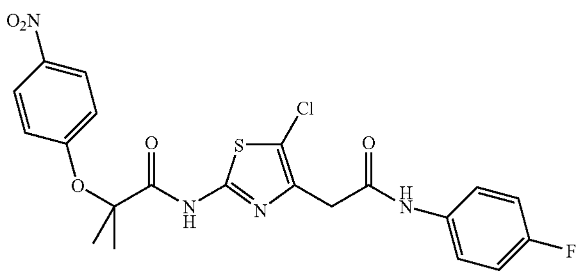 [SMILES: CC(C)(Oc1ccc([N+](=O)[O-])cc1)C(=O)Nc1nc(CC(=O)Nc2ccc(F)cc2)c(Cl)s1] | N-{5-Chloro-4-[(4-fluoro-phenylcarbamoyl)-methyl]-thiazol-2-yl}-2-methyl-2-(4-nitro-phenoxy)-propionamide.<br>$^1$H NMR (400 MHz, CDCl$_3$): δ 1.70 (s, 6H), 3.75 (s, 2H), 7.00 (m, 4H), 7.42 (m, 2H), 7.84 (bs, 1H), 8.23 (d, J = 8.8 Hz, 2H), 9.65 (bs, 1H).<br>MS (EI) m/z: 493.1 (M + 1). |
| J10 | 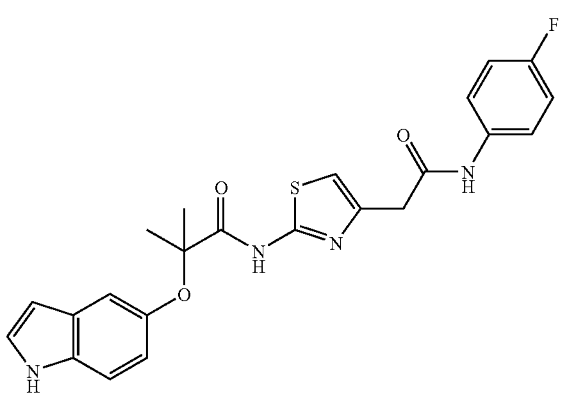 [SMILES: CC(C)(Oc1ccc2[nH]ccc2c1)C(=O)Nc1nc(CC(=O)Nc2ccc(F)cc2)cs1] | N-{4-[(4-Fluoro-phenylcarbamoyl)-methyl]-thiazol-2-yl}-2-(1H-indol-5-yloxy)-2-methyl-propionamide.<br>$^1$H NMR (400 MHz, CDCl$_3$): δ 1.58 (s, 6H), 3.79 (s, 2H), 6.51 (s, 1H), 6.86 (s, 1H), 6.90 (d, J = 8.4 Hz, 1H), 6.96 (t, 2H), 7.26 (d, 2H), 7.33 (d, J = 8.8 Hz, 1H), 7.44 (m, 2H).<br>MS (EI) m/z 453.1 (M + 1). |
| J11 | 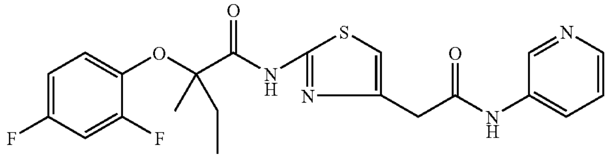 [SMILES: CCC(C)(Oc1ccc(F)cc1F)C(=O)Nc1nc(CC(=O)Nc2cccnc2)cs1] | 2-(2,4-Difluoro-phenoxy)-2-methyl-N-[4-(pyridin-3-ylcarbamoylmethyl)-thiazol-2-yl]-butyramide.<br>$^1$H NMR (DMSO): 0.87 (t, J = 7.6 Hz, 3H), 1.37 (s, 3H), 1.96-1.97 (m, 2H), 3.74 (s, 2H), 6.96-6.97 (m, 2H), 7.05 (s, 1H), 7.28-7.34 (m, 2H), 8.02 (d, J = 8 Hz, 1H), 8.23 (d, J = 3.6 Hz, 1H), 8.72 (s, 1H), 10.37 (s, 1H), 12.20 (s, 1H).<br>MS (EI) m/z: 447.00 (M + 1). |

Synthesis Type-K

Example K1

3-[1-Methyl-1-(thiazol-2-ylcarbamoyl)-ethoxy]-benzoic acid

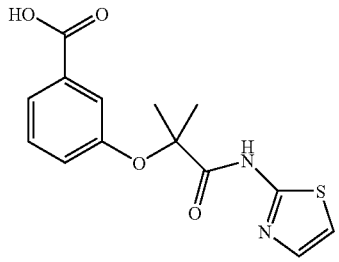 [SMILES: CC(C)(Oc1cccc(C(=O)O)c1)C(=O)Nc1nccs1]

To a solution of 3-[1-Methyl-1-(thiazol-2-ylcarbamoyl)-ethoxy]-benzoic acid tert-butyl ester (0.1 g, 0.275 mmol) in DCM (2 ml) a solution of TFA (3 ml) in DCM (3 ml) was added at 0° C. for 15 min. Reaction mixture was stirred at RT for 1 h, diluted with DCM (10 ml) washed with brine (2×4 ml) dried over $Na_2SO_4$ and concentrated under reduced pressure to obtain crude product. The crude product was triturated with hexane to obtain white solid, filtered and dried to obtain 3-[1-Methyl-1-(thiazol-2-ylcarbamoyl)-ethoxy]-benzoic acid (0.06 g, 85%). 3-[1-Methyl-1-(thiazol-2-ylcarbamoyl)-ethoxy]-benzoic acid.

$^1$H NMR (400 MHz, $CDCl_3$): δ 1.59 (s, 6H), 7.02 (m, 2H), 7.27 (m, 1H), 7.47 (d; J=3.6 Hz, 1H), 7.72 (d, J=7.6 Hz, 1H), 8.25 (s, 1H), 12.64 (bs, 1H). MS (EI) m/z: 307.0 (M+1). mp: 166-168° C.

Preparation of 3-[1-Methyl-1-(thiazol-2-ylcarbamoyl)-ethoxy]-benzoic acid tert-butyl ester use for the synthesis of 3-[1-Methyl-1-(thiazol-2-ylcarbamoyl)-ethoxy]-benzoic acid is same as example A1 using appropriate precursors

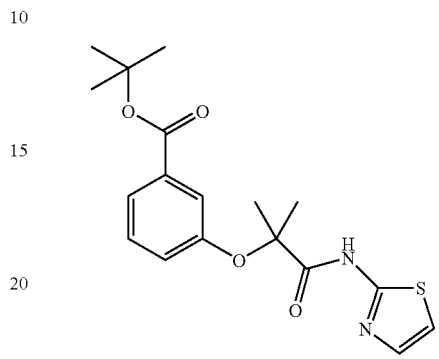

$^1$H NMR (400 MHz, $CDCl_3$): 1.57 (s, 9H), 1.62 (s, 6H), 7.03 (d, J=3.6 Hz, 1H), 7.13 (d, J=8.4 Hz, 1H), 7.36 (t, J=8.0 Hz, 1H), 7.49 (d, J=3.6, 1H), 7.60 (1H), 7.77 (d, J=8.0 Hz, 1H). MS (EI) m/z: 363.0 (M+1).

Following compounds were prepared in an analogous manner of Example K1 from the appropriate intermediates

| Example | Structure | IUPAC name and analytical data |
|---|---|---|
| K2 | 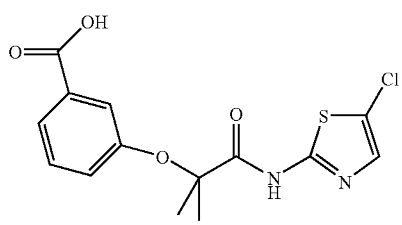 [SMILES: CC(C)(Oc1cccc(C(=O)O)c1)C(=O)Nc1ncc(Cl)s1] | 3-[1-(5-Chloro-thiazol-2-ylcarbamoyl)-1-methyl-ethoxy]-benzoic acid.<br>$^1$H NMR (400 MHz, $CDCl_3$): δ 1.59 (s, 6H), 7.10 (d, J = 7.6 Hz, 1H), 7.40 (m, 2H), 7.55 (s, 1H), 7.58 (d, J = 8.0 Hz, 1H).<br>MS (EI) m/z: 339.1 (M − 1). |
| K3 | 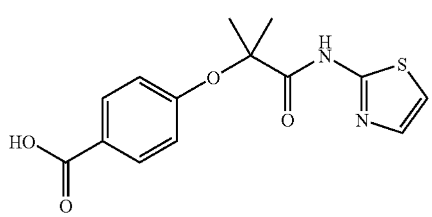 [SMILES: CC(C)(Oc1ccc(C(=O)O)cc1)C(=O)Nc1nccs1] | 4-[1-Methyl-1-(thiazol-2-ylcarbamoyl)-ethoxy]-benzoic acid.<br>$^1$H NMR (400 MHz, $CDCl_3$): δ 1.73 (s, 6H), 6.95 (d, J = 8.8 Hz, 2H), 7.06 (d, J = 3.6 Hz, 1H), 7.48 (d, J = 4.0 Hz, 1H), 7.80 (d, J = 8.4 Hz, 2H).<br>MS (EI) m/z: 304.8 (M − 1). |
| K4 | 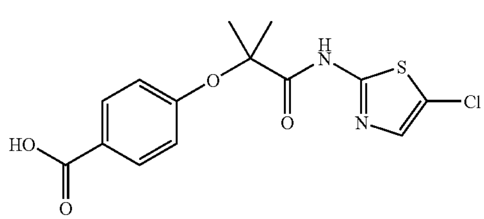 [SMILES: CC(C)(Oc1ccc(C(=O)O)cc1)C(=O)Nc1ncc(Cl)s1] | 4-[1-(5-Chloro-thiazol-2-ylcarbamoyl)-1-methyl-ethoxy]-benzoic acid.<br>$^1$H NMR (400 MHz, $CDCl_3$): δ 1.70 (s, 6H), 6.96 (d, J = 8.8 Hz, 2H), 7.30 (s, 1H), 7.84 (d, J = 8.8 Hz, 2H).<br>MS (EI) m/z: 338.7 (M − 1). |

N-(3-Amino-pyridin-2-yl)-2-(6-chloro-pyridin-2-yloxy)-2-methyl-propionamide

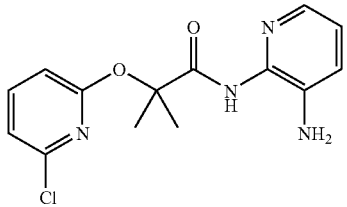 [SMILES: CC(C)(Oc1cccc(Cl)n1)C(=O)Nc1ncccc1N]

2-(6-Chloro-pyridin-2-yloxy)-2-methyl-propionic acid (0.53 g, 2.4 mmol) and 2,3-diaminopyridine (0.268 g, 2.4 mmol) were dissolved in DMF (5 ml) cooled to 0° C. and added EDCI (0.62 g, 3.2 mmol) and stirred for 4 h. The reaction mixture was extracted in EtOAc (30 ml) and washed with brine (2×10 ml) dried over Na$_2$SO$_4$ and concentrated under reduced pressure to obtain crude product. The product was purified on silica gel to yield N-(3-Amino-pyridin-2-yl)-2-(6-chloro-pyridin-2-yloxy)-2-methyl-propionamide (0.54 g, 72%). $^1$H NMR (400 MHz, CDCl$_3$): 4.84 (brs, 2H), 6.67 (dd, J=4.8 and 7.6 Hz, 1H), 6.78 (d, J=8.4 Hz, 1H), 7.02 (d, J=8. Hz, 1H), 7.40 (d, J=8. Hz, 1H), 7.61 (d, J=8 Hz, 1H), 7.996 (dd, J=4.8 Hz and 7.6 Hz, 1H). MS (EI) m/z: 307 (M+1).

N-(3-Acetylamino-pyridin-2-yl)-2-(6-chloro-pyridin-2-yloxy)-2-methyl propionamide

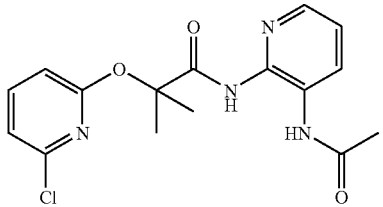 [SMILES: CC(=O)Nc1cccnc1NC(=O)C(C)(C)Oc1cccc(Cl)n1]

Acetylation of N-(3-Amino-pyridin-2-yl)-2-(6-chloro-pyridin-2-yloxy)-2-methyl-propionamide using acetyl chloride gives N-(3-Acetylamino-pyridin-2-yl)-2-(6-chloro-pyridin-2-yloxy)-2-methyl propionamide $^1$H NMR (400 MHz, CDCl3):): δ 1.79 (s, 6H), 2.12 (s, 3H), 6.83 (d, 1H, J=8 Hz), 6.90 (d, 1H, J=8 Hz), 7.25 (t, 1H, J=8 Hz), 7.54 (t, 1H, J=8 Hz), 7.85 (brs, 1H), 8.14 (d, 1H, J=8 Hz), 8.26 (d, 1H, J=8 Hz), 9.61 (brs, 1H), MS (EI) m/z: 349 (M+1), mp: 185° C.

2-(6-Chloro-pyridin-2-yloxy)-N-(3-methanesulfonylamino-pyridin-2-yl)-2-methyl-propionamide

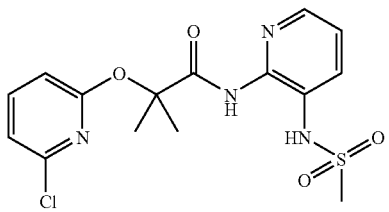 [SMILES: CC(C)(Oc1cccc(Cl)n1)C(=O)Nc1ncccc1NS(C)(=O)=O]

To a solution of N-(3-Amino-pyridin-2-yl)-2-(6-chloro-pyridin-2-yloxy)-2-methyl-propionamide (0.15 g, 4.9 mmol) and pyridine (0.042 g, 5.3 mmol) in DCM (5 ml) at 0° C. was added Methane sulfonyl chloride (0.06 g, 0.04 ml, 5.3 mmol) drop wise over a period of 5 min. The reaction mixture was stirred for 1 h. The reaction mixture was quenched with water (2 ml) extracted in DCM (20 ml), washed with brine (5 ml), dried over Na$_2$SO$_4$ and concentrated under reduced pressure to obtain crude product. The crude material thus obtained was purified by flash column affording 2-(6-Chloro-pyridin-2-yloxy)-N-(3-methanesulfonylamino-pyridin-2-yl)-2-methyl-propionamide (0.08 g, 5%). $^1$H NMR (400 MHz, CDCl$_3$): δ 1.790 (s, 6H), 2.87 (s, 3H), 6.67 (t, 1H, J=8 Hz), 6.78 (d, 11-1, J=8 Hz), 6.91 (d, 1H, J=8 Hz), 7.18 (d, 1H, J=8 Hz), 7.57 (t, 1H, J=8 Hz), 8.69 (d, 1H, J=8 Hz), 9.11 (brs, 1H). MS (EI) m/z: 385 (M+1).

Synthesis Type-L

Example L1

1-(2,4-Difluoro-phenoxy)-cyclopropanecarboxylic acid, thiazol-2-ylamide

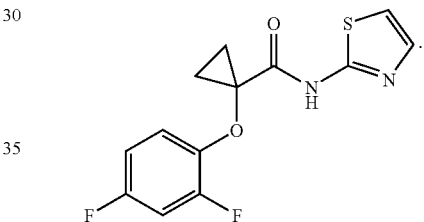

Preparation of 1-(2,4-Difluoro-phenoxy)-cyclopropanecarboxylic acid, thiazol-2-ylamide is same as example A1 using 1-(2,4-Difluoro-phenoxy)-cyclopropanecarboxylic acid as precursors. $^1$H NMR (400 MHz, CDCl$_3$): δ 1.36-1.39 (q, 2H), 1.74-1.77 (q, 2H), 6.75-6.80 (m, 1H), 6.87-6.92 (m, 2H), 6.94-6.97 (m, 1H), 7.00 (d, J=3.2 Hz, 1H), 7.44 (d, J=3.6 Hz, 1H), 9.9 (bs, 1H), MS (EI) m/z: 296.9 (M+1).

Preparation of 1-(2,4-Difluoro-phenoxy)-cyclopropanecarboxylic acid used in Example L1 is described below:

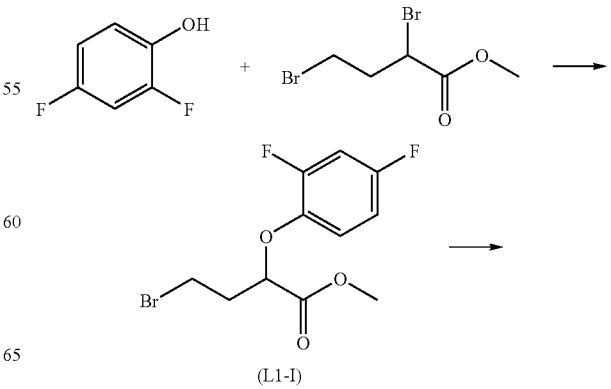

(L1-I)

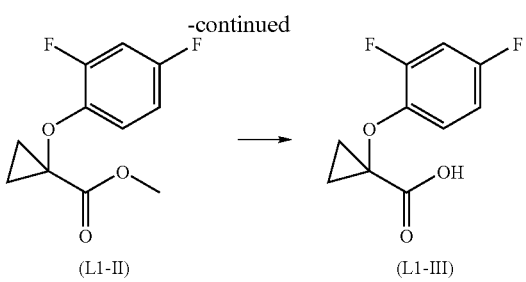

4-Bromo-2-(2,4-difluoro-phenoxy)-butyric acid methyl ester (L1-I)

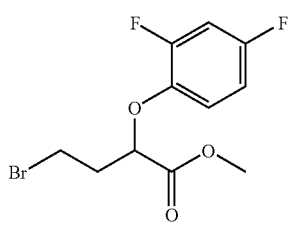 [SMILES: COC(=O)C(CCBr)Oc1ccc(F)cc1F]

To a solution of 2,4-difluoro phenol (0.35 g, 2.73 mmol) in DMF (5 ml), added potassium carbonate (0.38 g, 2.73 mmol) and 2,4-Dibromo-butyric acid methyl ester (0.71 g, 2.74 mmol) and heated at 60° C. for 3 h. Reaction mixture was cooled to r.t. It was then extracted in EtOAc (30 ml) and washed with brine (2×10 ml), dried over $Na_2SO_4$ and concentrated under reduced pressure to obtain crude product, purification on silica gel to yield 4-Bromo-2-(2,4-difluoro-phenoxy)-butyric acid methyl ester (0.52 g, 61%). $^1$H NMR (400 MHz, $CDCl_3$): δ 12.42-2.56 (m, 2H), 3.53-3.71 (m, 2H), 3.77 (s, 3H), 4.81 (dd, J=3.6 and 8.8 Hz, 1H), 6.72-6.80 (m, 1H), 6.85-6.90 (m, 1H), 6.95-7.02 (m, 1H).

1-(2,4-Difluoro-phenoxy)-cyclopropanecarboxylic acid methyl ester (L1-II)

A solution of 4-Bromo-2-(2,4-difluoro-phenoxy)-butyric acid methyl ester (3.167 g, 10.29 mmol) in THF (40 ml) was added to a suspension of potassium tert butoxide (1.148 g, 10.26 mmol) in THF (20 ml) and the reaction mixture was heated at 60° C. for 4 hr. Reaction mixture was cooled to room temp, quenched with brine (5 ml) extracted in ether (50 ml) and washed with brine (2×5 ml), dried over $Na_2SO_4$ and concentrated under reduced pressure to obtain crude product, 1-(2,4-Difluoro-phenoxy)-cyclopropanecarboxylic acid methyl ester (1.9 g, 81%) which was used as such in the next step.

1-(2,4-Difluoro-phenoxy)-cyclopropanecarboxylic acid (L1-III)

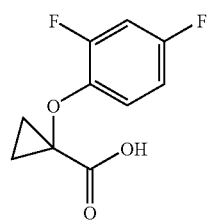 [SMILES: O=C(O)C1(Oc2ccc(F)cc2F)CC1]

To a solution of 1-(2,4-Difluoro-phenoxy)-cyclopropanecarboxylic acid methyl ester (1.89 g, 8.28 mmol) in THF (20 ml) added a solution of LiOH (0.86 g, 20.7 mmol) in water (5 ml) was added, and mixture is stirred at r.t. for 18 h. Solvent was evaporated at reduced pressure acidified with 1N HCl (pH~2) and extracted in ethyl acetate (70 ml) and washed with brine (2×10 ml), dried over $Na_2SO_4$ and concentrated under reduced pressure to obtain 1-(2,4-Difluoro-phenoxy)-cyclopropanecarboxylic acid (1.16 g, 66%). $^1$H NMR (400 MHz, $CDCl_3$): δ 1.46 (dd, J=5.6 and 9.2 Hz, 1H), 1.71 (dd, J=5.6 and 9.2 Hz, 1H), 2.27-2.31 (m, 1H), 3.97-4.0 (m, 1H), 4.85 (t, J=5.6 Hz, 1H), 6.77-83 (m, 1H), 6.85-6.92 (m, 1H), 7.0-7.06 (m, 1H).

Following compounds were prepared in an analogous manner of Example L1 from the appropriate intermediates

| Example | Structure | IUPAC name and analytical data |
|---|---|---|
| L2 | 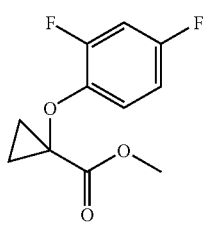 | 1-(2,4-Difluoro-phenoxy)-cyclopropane-carboxylic acid, (5-chloro-thiazol-2-yl)-amide. $^1$H NMR (400 MHz, $CDCl_3$): δ 1.38-1.40 (q, 2H), 1.72-1.74 (q, 2H), 3.5 (bs, 1H), 6.77-6.82 (m, 1H), 6.88-6.98 (m, 2H), 9.58 (bs, 1H). MS (EI) m/z: 330.9 (M + 1). |

| Example | Structure | IUPAC name and analytical data |
|---|---|---|
| L3 | 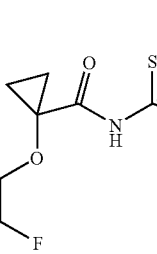 | (5-Chloro-2-{[1-(2,4-difluoro-phenoxy)-cyclopropanecarbonyl]-amino}-thiazol-4-yl)-acetic acid.<br>$^1$H NMR (400 MHz, CDCl$_3$): δ 1.38-1.40 (q, 2H), 1.72-1.74 (q, 2H), 3.6 (s, 2H), 6.73-6.77 (m, 1H), 6.82-6.92 (m, 2H).<br>MS (EI) m/z: 388.9 (M + 1). |

N-(5-Chloro-thiazol-2-yl)-2-methyl-2-{3-[2-(4-trifluoromethyl-phenyl)-ethylamino]-phenoxy}-propionamide

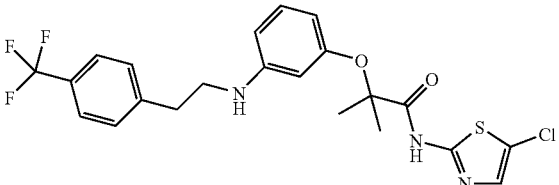

To a solution of 2-Methyl-2-{3-[2-(4-trifluoromethyl-phenyl)-ethylamino]-phenoxy}-propionic acid (0.075 g, 0.204 mmol) in DCM (5 ml) added triethyl amine (0.034 ml, 0.24 mmol) and HOBt (0.0.037 g, 0.24 mmol) at 0° C. After stirring at this temperature for 5 min. added 2-amino-5-chlorothiazole (0.041 g, 0.285 mmol) and followed by EDCI (0.047 g, 0.244 mmol). The resulting solution was stirred for 12 h. then quenched with sat NH$_4$Cl solution (15 ml). The aqueous phase was extracted with CH$_2$Cl$_2$ (3×50 ml). The organic phase were successively washed with 2% HCl (50 ml), brine (50 ml) and dried over Na$_2$SO$_4$. After evaporation, the residue was purified by flash chromatography (1:5 ethyl acetate:hexanes) to give N-(5-Chloro-thiazol-2-yl)-2-methyl-2-{3-[2-(4-trifluoromethyl-phenyl)-ethylamino]-phenoxy}-propionamide (0.03 g, 30%). $^1$H NMR (400 MHz, CDCl$_3$): δ 1.59 (s, 6H), 2.96 (t, J=6.8 Hz, 2H), 3.39 (bs, 2H), 3.7 (bs, 1H), 6.18 (s, 1H), 6.26-6.38 (m, 2H), 7.07 (m, 1H), 7.31 (m, 2H), 7.58 (d, J=8 Hz, 2H), 10.0 (s, 1H), MS (EI) m/z: 484.1 (M+1).

Preparation of 2-Methyl-2-{3-[2-(4-trifluoromethyl-phenyl)-ethylamino]-phenoxy}-propionic acid used in Typical Example is described below:

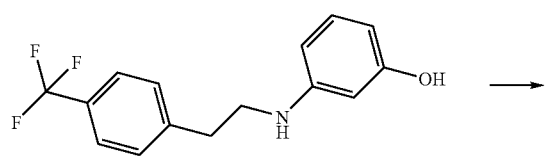

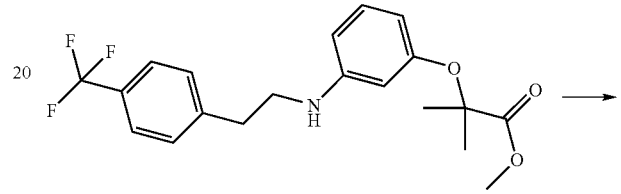

2-Methyl-2-{3-[2-(4-trifluoromethyl-phenyl)-ethylamino]-phenoxy}-propionic acid ethyl ester

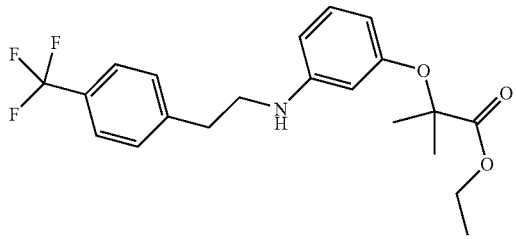 [SMILES: CCOC(=O)C(C)(C)Oc1cccc(NCCc2ccc(C(F)(F)F)cc2)c1]

To a solution of 2-(3-Amino-phenoxy)-2-methyl-propionic acid ethyl ester (0.25 g, 1.11 mmol) in acetonitrile (5 ml), Na2CO3 (0.131 g, 1.24 mmol) and 1-(2-Iodo-ethyl)-4-trifluoromethyl-Benzene (0.372 g, 1.24 mmol) were added. The reaction mixture was stirred at r. t for 3 days, solvent was removed under reduced pressure and extracted in Ethyl acetate (75 ml) and washed with brine (2×10 ml) dried over Na$_2$SO$_4$. After evaporation, the residue was purified by flash chromatography (1:5 ethyl acetate:hexanes) to give 2-Methyl-2-{3-[2-(4-trifluoromethyl-phenyl)-ethylamino]-phenoxy}-propionic acid ethyl ester (0.19 g, 43%).

2-Methyl-2-{3-[2-(4-trifluoromethyl-phenyl)-ethylamino]-phenoxy}-propionic acid

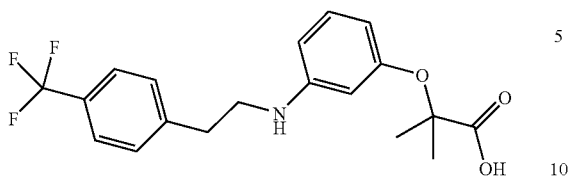

To a solution of 2-Methyl-2-{3-[2-(4-trifluoromethyl-phenyl)-ethylamino]-phenoxy}-propionic acid ethyl ester (0.24 g, 0.608 mmol) in THF (15 ml) was added a solution of LiOH (0.127 g, 3.03 mmol) in water (3.4 ml) and stirred at r.t. for 18 h. After evaporation of the solvent, the residue was diluted with ethyl acetate (100 ml); cool to 0° C., acidified with 1N HCl (pH~3-4). The organic phase were washed with, brine (20 ml) and dried over $Na_2SO_4$ and concentrated to get 2-Methyl-2-{3-[2-(4-trifluoromethyl-phenyl)-ethylamino]-phenoxy}-propionic acid (0.075 g, 33%). $^1$H NMR (400 MHz, $CDCl_3$): δ 1.588 (s, 6H), 2.97 (t, J=6.8 Hz, 2H), 3.41 (t, J=6.8 Hz, 2H), 6.22 (s, 1H), 6.30 (d, J=8.4 Hz, 1H), 6.37 (d, J=8 Hz, 1H), 7.08 (t, J=8.0 Hz, 1H), 7.32 (d, J=8 Hz, 2H), 7.57 (d, J=7.6 Hz, 2H).

Synthesis Type-M

2-(2,4-Difluoro-phenoxy)-N-{4-[2-(4-fluoro-phenoxy)-ethyl]-thiazol-2-yl}-2-methyl-propionamide

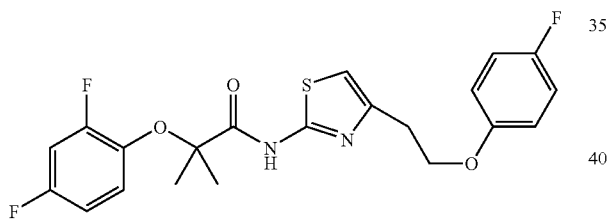

Preparation of 2-(2,4-Difluoro-phenoxy)-N-{4-[2-(4-fluoro-phenoxy)-ethyl]-thiazol-2-yl}-2-methyl-propionamide is same as example A1 using 4-[2-(4-Fluoro-phenoxy)-ethyl]-thiazol-2-ylamine as one of the precursors. $^1$H NMR (400 MHz, $CDCl_3$): δ 1.56 (s, 6H), 3.14 (t, 2H), 4.24 (t, 2H), 6.75 (s, 1H), 6.82-6.86 (m, 3H), 6.89-6.93 (m, 1H), 6.94-6.98 (m, 2H), 7.02-7.08 (m, 1H). 10.1 (brs, 1H), MS (EI) m/z: 436.8 (M+1).

Preparation of 4-[2-(4-Fluoro-phenoxy)-ethyl]-thiazol-2-ylamine used in Example M1 is described below:

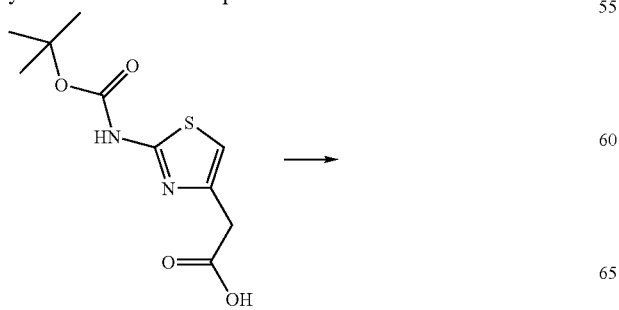

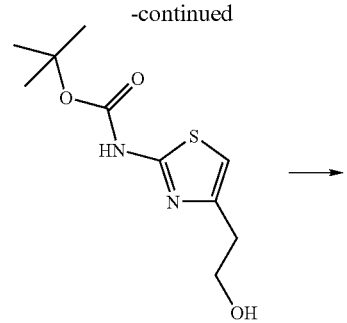

(M1-I)

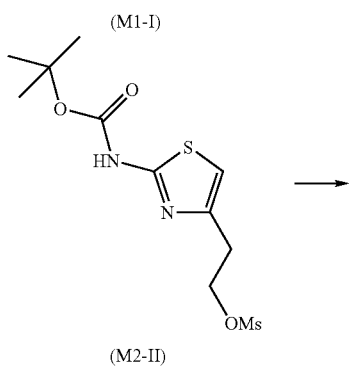

(M2-II)

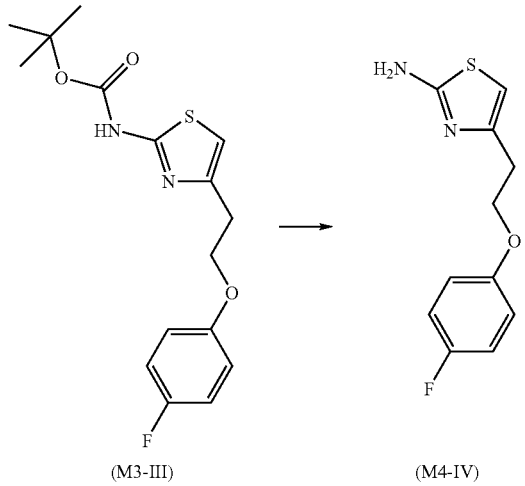

(M3-III)       (M4-IV)

[4-(2-Hydroxy-ethyl)-thiazol-2-yl]-carbamic acid tert-butyl ester (M1-I)

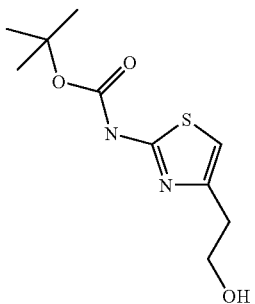 [SMILES: CC(C)(C)OC(=O)Nc1nc(CCO)cs1]

To a solution of (2-tert-Butoxycarbonylamino-thiazol-4-yl)-acetic acid ethyl ester (4 g, 13.9 mmol) in EtOH (50 ml), NaBH4 (1.59 g, 41.9 mmol) was added at 0° C. and stirred at r.t. for 18 h. Solvent was removed under reduced pressure and extracted in Ethyl acetate (150 ml) washed with brine (2×30 ml) dried over Na₂SO₄. After evaporation, the residue was purified by preparative chromatography (1:3 EtOAc:Hexanes) to give [4-(2-Hydroxy-ethyl)-thiazol-2-yl]-carbamic acid tert-butyl ester (2.2 g, 65%). ¹H NMR (400 MHz, CDCl₃): 1.): 1.53 (s, 9H), 2.87 (t, J=5.2 2H), 3.90 (t, J=5.2 Hz, 2H), 6.55 (s, 1H). MS (EI) m/z: 245 (M+1).

Methanesulfonic acid 2-(2-tert-butoxycarbonylamino-thiazol-4-yl)-ethyl ester (M1-II)

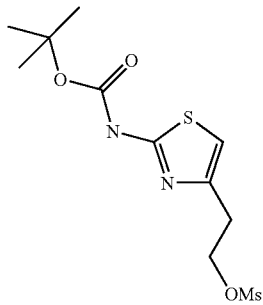 [SMILES: CC(C)(C)OC(=O)Nc1nc(CCOS(C)(=O)=O)cs1]

To a solution of [4-(2-Hydroxy-ethyl)-thiazol-2-yl]-carbamic acid tert-butyl ester (5 g, 20 mmol) and triethyl amine (5.8 ml, 40 mmol) in DCM (50 ml) was added methanesulfonyl chloride (1.9 ml, 24 mmol) slowly over a period of 10-15 min. The reaction mixture was stirred at r.t. for 4 hr, quenched with brine (10 ml) and extracted in DCM (100 ml), dried over Na₂SO₄ and passed through a short column of silica gel bed and concentrated to obtain methanesulfonic acid 2-(2-tert-butoxycarbonylamino-thiazol-4-yl)-ethyl ester (6.0 g, 90%) which was used as such for the next step without further purification.

{4-[2-(4-Fluoro-phenoxy)-ethyl]-thiazol-2-yl}-carbamic acid tert-butyl ester (M1 III)

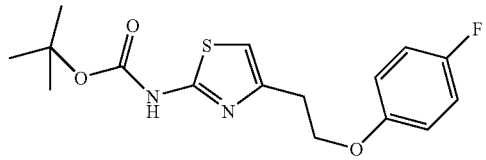 [SMILES: CC(C)(C)OC(=O)Nc1nc(CCOc2ccc(F)cc2)cs1]

To a mixture of Methanesulfonic acid 2-(2-tert-butoxycarbonylamino-thiazol-4-yl)-ethyl ester (6.0 g, 18 mmol) and 4-fluoro phenol (5.21 g, 46 mmol) in Toluene (60 ml) K₂Co₃ (7.7 g, 55 mmol) was added and heated at 80° C. for 18 h. The reaction mixture was filtered to remove solid residues, washed with ethyl acetate (50 ml) and combined organic layer washed with brine (20 ml) dried over Na₂SO₄. Solvent was removed under reduced pressure, crude product was purified by column chromatography using 1:10 EtOAC and Hexanes to obtain {4-[2-(4-Fluoro-phenoxy)-ethyl]-thiazol-2-yl}-carbamic acid tert-butyl ester (2.56 g, 40%). ¹H NMR (400 MHz, CDCl₃): 1.53 (s, 9H), 3.09 (t, J=6.4 Hz, 2H), 4.20 (t, J=6.4 Hz, 2H), 6.21 (s, 1H), 6.811-6.84 (m, 2H), 6.95 (t, J=8.8 Hz, 2H). 8.28 (brs, 1H). MS (EI) m/z: 338.89 (M+1).

4-[2-(4-Fluoro-phenoxy)-ethyl]-thiazol-2-ylamine (M1-IV)

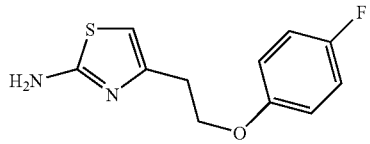 [SMILES: Nc1nc(CCOc2ccc(F)cc2)cs1]

TFA (12 ml) was added to a solution of {4-[2-(4-Fluoro-phenoxy)-ethyl]-thiazol-2-yl}-carbamic acid tert-butyl ester (2.55 g, 7.5 mmol) in DCM (100 ml) at 0° C. and stirred at r.t. for 4 h. The reaction was quenched with saturated aqueous NaHCO₃ solution (15 ml) and extracted in DCM, dried over Na₂SO₄, evaporated under reduced pressure to yield 4-[2-(4-Fluoro-phenoxy)-ethyl]-thiazol-2-ylamine (1.55 g, 86%). ¹H NMR (400 MHz, CDCl₃): δ 3.0 (t, J=6.8 Hz, 2H), 4.20 (t, J=6.8 Hz, 2H), 4.88 (brs, 2H), 6.26 (s, 1H), 6.83-6.86 (m, 2H), 6.94-6.98 (m, 2H).

Following compounds were prepared in an analogous manner of Example M1 from the appropriate intermediates

| Sr. No. | Structure | IUPAC name and analytical data |
|---|---|---|
| M2 | 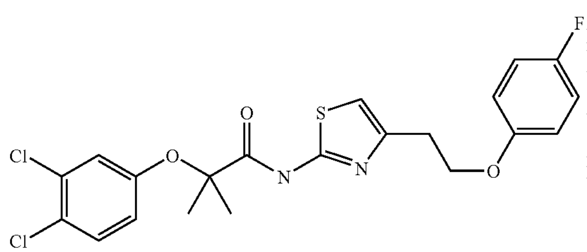 [SMILES: CC(C)(Oc1ccc(Cl)c(Cl)c1)C(=O)Nc1nc(CCOc2ccc(F)cc2)cs1] | F2-(3,4-Dichloro-phenoxy)-N-{4-[2-(4-fluoro-phenoxy)-ethyl]-thiazol-2-yl}-2-methyl-propionamide<br>¹H NMR (400 MHz, CDCl₃): δ 1.61 (s, 6H), 3.15 (t, 2H), 4.24 (t, 2H), 6.78 (s, 1H), 6.82-6.87 (m, 3H), 6.95-7.00 (m, 2H), 7.13 (d, 1H, 2.8 Hz); 7.39 (d, 1H, 8 Hz), 9.87 (brs, 1H). MS (EI) m/z: 468.7 (M + 1). |

Synthesis Type-N

Example N1

N-(5-Chloro-thiazol-2-yl)-2-(2-cyclopentylmethoxy-phenoxy)-2-methyl-propionamide

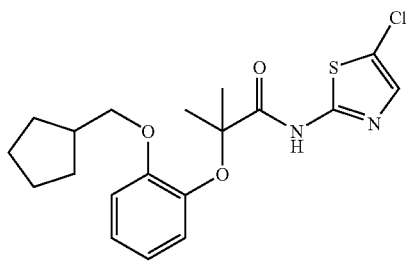 [SMILES: CC(C)(Oc1ccccc1OCC1CCCC1)C(=O)Nc1ncc(Cl)s1]

Preparation of N-(5-Chloro-thiazol-2-yl)-2-(2-cyclopentylmethoxy-phenoxy)-2-methyl-propionamide (N) is same as Typical example (A) using 2-(2-Cyclopentylmethoxy-phenoxy)-2-methyl-propionic acid as one of the precursors. ¹H-NMR (CDCl₃) δ 1.21-1.25 (m, 4H), 1.45-1.48 (m, 2H), 1.54 (s, 6H), 1.70-1.75 (m, 2H), 2.45-2.49 (m, 1H), 3.89-3.91 (d, 2H), 6.87-6.94 (m, 2H), 7.05-7.11 (m, 2H), 7.29 (s, 1H), 10.82 (s, 1H), MS (EI) m/z: 395 (M+1)

2-(2-Cyclopentylmethoxy-phenoxy)-2-methyl-propionic acid

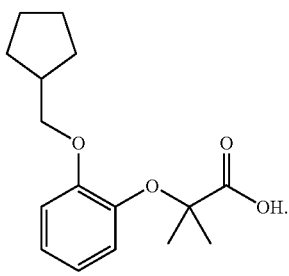 [SMILES: CC(C)(Oc1ccccc1OCC1CCCC1)C(=O)O]

To a solution of catacol (0.5 g, 4.54 mmol), triphenylphosphine (1.79 g, 6.8 mmol) and cyclopenylmethanol (0.68 g, 6.8 mmol) in THF (5 ml) DIAD (1.37 g, 6.8 mmol) is added drop wise over a period of 10-15 min at 0° C. The reaction mixture stirred at r.t. for 18 h, quenched with brine (5 ml), extracted in EtOAc (2×20 ml), and dried over Na₂SO₄. Solvent was evaporated under reduced pressure and crude product. To a solution of 2-Cyclopentylmethoxy-phenol (0.1 g, 0.52 mmol) and 2-bromoisobutyrate ethyl ester (0.15 g, 0.78 mmol) in DMSO (2 ml) Cs₂CO₃ (0.25 g, 0.78 mmol) was added and heated at 60° C. for 4 h. The reaction mixture was cooled to r.t. and poured on 10 ml of water, extracted in EtOAc (2×20 ml) dried over Na₂SO₄. Solvent was removed under reduced pressure to yield 2-(2-Cyclopentylmethoxy-phenoxy)-2-methyl-propionic acid ethyl ester (0.1 g, 63%) which was hydrolysed to give 2-(2-Cyclopentylmethoxy-phenoxy)-2-methyl-propionic acid using method Typical Example (A1-II).

Following compounds were prepared in an analogous manner of Example N1 from the appropriate intermediates

| Example | Structure | IUPAC name and analytical data |
|---|---|---|
| N2 | ![structure] | 2-[4-Chloro-3-(2-thiophen-3-yl-ethoxy)-phenoxy]-2-methyl-N-thiazol-2-yl-propionamide<br>¹H NMR (400 MHz, CDCl₃): δ 1.66 (s, 6H), 3.11 (t, 2H), 4.11 (t, 2H), 6.64-6.66 (m, 2H), 7.00-7.03 (m, 2H); 7.07 (s, 1H), 7.27-7.32 (m, 2H); 7.50 (d, J = 3.6 Hz, 1H); 10.40 (bs, 1H); MS (EI) m/z 423 (M + 1). |
| N3 | ![structure] | 2-[2-Chloro-5-(2-thiophen-3-yl-ethoxy)-phenoxy]-2-methyl-N-thiazol-2-yl-propionamide<br>¹H NMR (400 MHz, CDCl₃): δ 1.66 (s, 6H), 3.16 (t, 2H), 4.13 (t, 2H), 6.45-6.47 (m, 1H), 6.51 (d, J = 2 Hz, 1H), 7.02 (d, J = 3.2 Hz, 1H), 7.09 (d, J = 4.8 Hz, 1H), 7.15 (s, 1H), 7.24 (d, J = 8.8 Hz, 1H), 7.27-7.29 (m, 1H), 7.48 (d, J = 3.2, 1H), 10.15 (bs, 1H); MS (EI) m/z 423 (M + 1) |

Synthesis Type-O

Example O1

2-(2,4-Difluoro-phenoxy)-2-(4-methanesulfonyl-phenyl)-N-thiazol-2-yl-propionamide

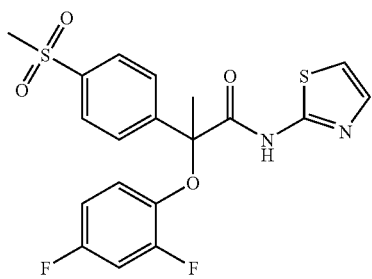 [SMILES: CC(Oc1ccc(F)cc1F)(C(=O)Nc1nccs1)c1ccc(S(C)(=O)=O)cc1]

To a mixture of 2-(2,4-Difluoro-phenoxy)-2-(4-methanesulfonyl-phenyl)-propionic acid (0.184 g, 0.52 mmol), 2-aminothiazole (0.59 g, 0.60 mmol) HOBt (0.070 g, 0.52 mmol), and EDCI 0.10 g, 0.52 mmol) in methylene dichloride (10 ml) was added triethyl amine (0.06 g, 0.59 mmol). The resulting mixture was stirred at room temperature for overnight followed by dilution with 10 ml methylene dichloride. The reaction mixture was poured onto water (20 ml), and organic layer separated, washed with water (2×20 ml), brine (20 ml), dried over sodium sulfate and solvent evaporated to get residue which was purified by preparative TLC using 50% ethyl acetate in hexane as mobile phase to give the desired compound (0.12 g). $^1$H NMR (400 MHz, CDCl$_3$): δ 1.90 (s, 3H), 3.08 (s, 3H), 6.64-6.71 (m, 2H), 6.94 (m, 1H), 7.05 (d, J=3.6 Hz, 1H), 7.51 (d, J=3.6 Hz, 1H), 7.86 (d, J=8.4 Hz, 2H), 8.01 (d, J=8.4 Hz, 2H), 10.20 (s, 1H); MS (EI) m/z: 439.00 (M+1); mp: 89-90° C.

The preparation of 2-(2,4-Difluoro-phenoxy)-2-(4-methanesulfonyl-phenyl)-propionic acid used in Example (O) is described below.

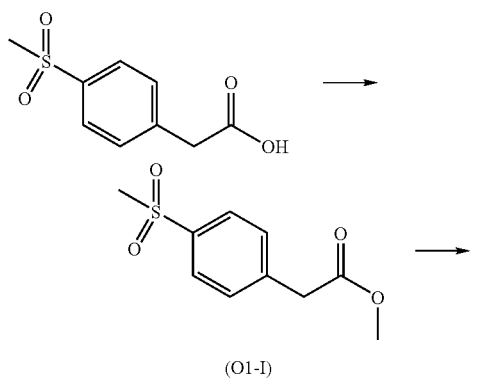

(O1-I)

(O1-II)

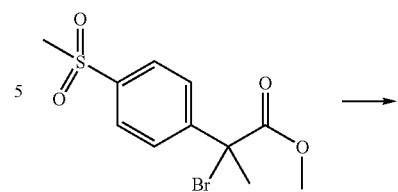

(O1-III)

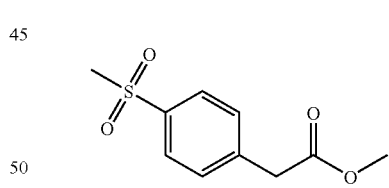

(O1-IV)

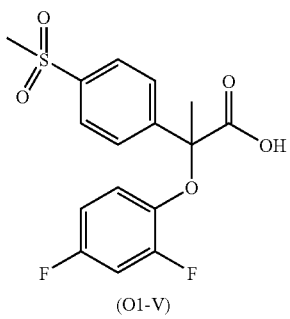

(O1-V)

(4-Methanesulfonyl-phenyl)-acetic acid methyl ester (O1-I)

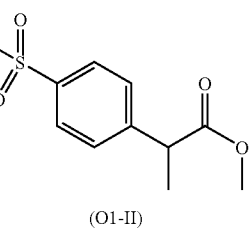

A solution of (4-Methanesulfonyl-phenyl)-acetic acid (25 g, 116.69 mmol) in methanol (300 ml) is treated with catalytic amount of sulfuric acid (2 ml). The reaction mixture was refluxed for 24 h. The solvent was then removed under reduced pressure, residue was dissolve in ethyl acetate (200 ml), the organic layer washed with water (2×100 ml), brine (100 ml), dried over sodium sulfate, and solvent was removed under reduced pressure to give (4-Methanesulfonyl-phenyl)-acetic acid methyl ester 26.37 g, 99%). $^1$H NMR (400 MHz, CDCl$_3$): δ 3.06 (s, 3H), 3.73 (s, 3H), 7.50 (d, J=8.4 Hz, 2H), 7.91 (d, J=8.4 Hz, 2H).

2-(4-Methanesulfonyl-phenyl)-propionic acid methyl ester (O1-II)

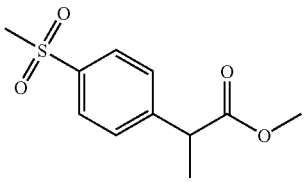

To a solution of diisopropylamide (0.46 g, 4.56 mmol) in THF (10 ml) was added n-Butyl lithium (3 ml of 1.6 M, 4.80 mmol) drop wise at −78° C. in nitrogen atmosphere and stirred for 30 minutes, to this slowly added solution of (4-Methanesulfonyl-phenyl)-acetic acid methyl ester (1.0 g, 4.38 mmol) and 1,3 dimethyl 3,4,5,6-tetrahydro-2-pyrimidone (3.17 g, 27.75 mmol), stirred for 1 hour at −78° C., followed by drop wise addition of solution of iodomethane in THF (1.14 g, 8.03 mmol in 10 ml) and stirred at the same temperature for one hour. Reaction mixture was allowed to come at RT and stirred for overnight. The reaction mixture was then poured into water (40 ml) under stirring, THF was removed under reduced pressure, and residue was extracted with ethyl acetate (2×25 ml), organic layer was washed with water (2×20 ml), dried over sodium sulfate and solvent was removed under reduced pressure to get oily residue which was purified by column chromatography over silica gel (100-200 mesh), using 50% ethyl acetate in hexanes as an eluent to afford 2-(4-Methanesulfonyl-phenyl)-propionic acid methyl ester (0.94 g, 88.5%) as white solid. $^1$H NMR (400 MHz, CDCl$_3$): δ 1.54 (d, J=7.2 Hz, 3H), 3.06 (s, 3H), 3.69 (s, 3H), 3.83 (q, J=7.2 Hz, 1H), 7.51 (d, J=8.4 Hz, 2H), 7.90 (d, J=8.4 Hz, 2H), 2-Bromo-2-(4-methanesulfonyl-phenyl)-propionic acid methyl ester (O1-III)

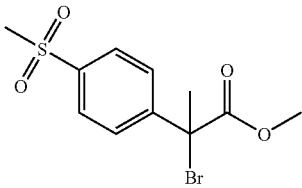

Mixture of 2-(4-Methanesulfonyl-phenyl)-propionic acid methyl ester (0.939 g, 0.3.88 mmol), N-bromosuccinimide (0.69 g, 3.88 mmol) and catalytic amount of benzoyl peroxide (0.01 g) in carbon tetrachloride (75 ml) was refluxed for 1 hour under nitrogen atmosphere, RM was cooled to room temperature and poured onto water (50 ml) under stirring, layer separated, organic layer was washed with water (2×25 ml). Removal of solvent gave the 2-Bromo-2-(4-methanesulfonyl-phenyl)-propionic acid methyl ester (1.22 g) as white solid which was used for the next step without further purification. $^1$H NMR (400 MHz, CDCl$_3$): δ 2.32 (s, 3H), 3.08 (s, 3H), 3.82 (s, 3H), 7.78 (d, J=8.4 Hz, 2H), 7.94 (d, J=8.4 Hz, 2H).

2-(2,4-Difluoro-phenoxy)-2-(4-methanesulfonyl-phenyl)-propionic acid (O1-V)

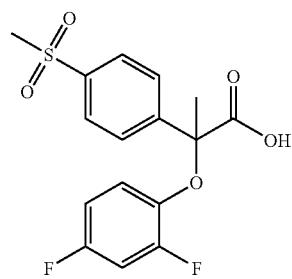 [SMILES: CC(Oc1ccc(F)cc1F)(C(=O)O)c1ccc(S(C)(=O)=O)cc1]

Potassium carbonate (0.15 g, 1.08 mmol) was added to a mixture of 2-Bromo-2-(4-methanesulfonyl-phenyl)-propionic acid methyl ester and 2,4-difluorophenol in DMF (5 ml) and heated at 60-70° C. for 2-3 Hrs then cool the reaction mixture to RT and poured onto water (25 ml) which was then extracted with ethyl acetate (2×25 ml), organic layer was washed with water (2×25 ml), dried over sodium sulfate and solvent was removed under reduced pressure to get 2-(2,4-Difluoro-phenoxy)-2-(4-methanesulfonyl-phenyl)-propionic acid methyl ester as oil which was taken in a mixture of methanol (5 ml) and sodium hydroxide in water (0.04 g in 5 ml). This mixture was stirred at room temperature for overnight. Methanol was removed from the reaction mixture, acidified with 1N HCl, extracted with ethyl acetate (2×25 ml), washed with brine (20 ml), solvent was removed to get the desired product 2-(2,4-Difluoro-phenoxy)-2-(4-methanesulfonyl-phenyl)-propionic acid. $^1$H NMR (400 MHz, CDCl$_3$): δ 1.82 (s, 3H), 3.45 (s, 3H), 6.71-6.75 (m, 1H), 6.81-6.93 (m, 2H), 7.86 (d, J=8.4 Hz, 2H), 7.95 (d, J=8.4 Hz, 2H).

Following compounds were prepared in an analogous manner of Example O1 from the appropriate intermediates

| Example | Structure | IUPAC name and analytical data |
|---|---|---|
| O2 | 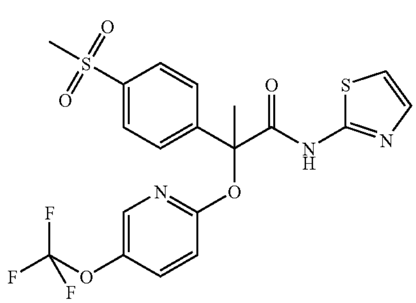 | 2-(4-Methanesulfonyl-phenyl)-N-thiazol-2-yl-2-(5-trifluoromethoxy-pyridin-2-yloxy)-propionamide.<br>$^1$H NMR (400 MHz, CDCl$_3$): δ 2.20 (s, 3H), 3.14 (s, 3H), 7.01 (d, J = 3.6 Hz, 1H), 7.16 (d, J = 8.8 Hz, 1H), 7.40 (d, J = 3.6 Hz, 1H), 7.82 (d, J = 8.8 Hz, 2H), 7.93-7.96 (m, 3H) 8.44 (s, 1H), 9.40 (bs, 1H).<br>MS (EI) m/z: 472.00 (M + 1). |

| Example | Structure | IUPAC name and analytical data |
|---|---|---|
| O3 | 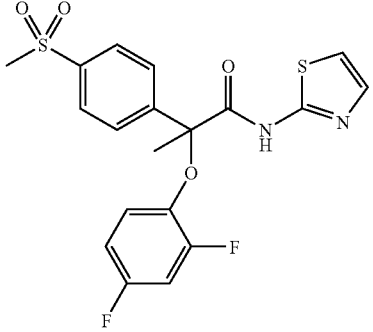 [SMILES: CC(Oc1ccc(F)cc1F)(C(=O)Nc1nccs1)c1ccc(S(C)(=O)=O)cc1] | 2-(2,4-Difluoro-phenoxy)-2-(4-methanesulfonyl-phenyl)-N-thiazol-2-yl-propionamide.<br>$^1$H NMR (400 MHz, CDCl$_3$): δ 1.90 (s, 3H), 3.08 (s, 3H), 6.64-6.71 (m, 2H), 6.94 (m, 1H), 7.05 (d, J = 3.6 Hz, 1H), 7.51 (d, J = 3.6 Hz, 1H), 7.86 (d, J = 8.4 Hz, 2H), 8.01 (d, J = 8.4 Hz, 2H), 10.20 (s, 1H).<br>MS (EI) m/z: 439.00 (M + 1). |
| O4 | 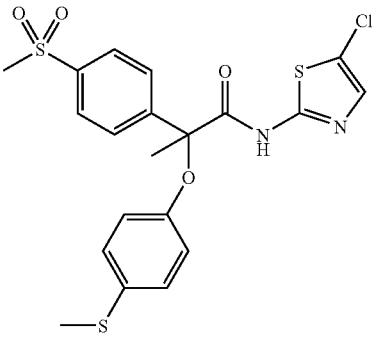 [SMILES: CSc1ccc(OC(C)(C(=O)Nc2ncc(Cl)s2)c2ccc(S(C)(=O)=O)cc2)cc1] | N-(5-Chloro-thiazol-2-yl)-2-(4-methanesulfonyl-phenyl)-2-(4-methylsulfanyl-phenoxy)-propionamide.<br>$^1$H NMR (400 MHz, CDCl$_3$): δ 1.90 (s, 3H), 2.40 (s, 3H), 3.06 (s, 3H), 6.71 (d, J = 8.8 Hz, 2H), 7.13 (d, J = 8.8 Hz, 2H), 7.31 (s, 1H), 7.81 (d, J = 8.4 Hz, 2H), 7.99 (d, J = 8.8 Hz, 2H), 10.10 (s, 1H).<br>MS (EI) m/z: 483.00 (M + 1).<br>mp: 67-68° C. |
| O5 | 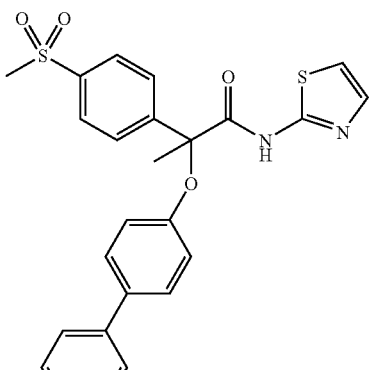 | 2-(Biphenyl-4-yloxy)-2-(4-methanesulfonyl-phenyl)-N-thiazol-2-yl-propionamide.<br>$^1$H NMR (400 MHz, CDCl$_3$): δ 2.00 (s, 3H), 3.06 (s, 3H), 6.86 (d, J = 8.8 Hz, 2H), 7.04 (d, J = 3.2 Hz, 1H), 7.40 (d, J = 8 Hz, 1H), 7.40-7.52 (m, 6H), 7.88 (d, J = 8.4 Hz, 2H), 8.01 (d, J = 8 Hz, 2H), 10.20 (s, 1H).<br>MS (EI) m/z: 479.10 (M + 1). |
| O6 | 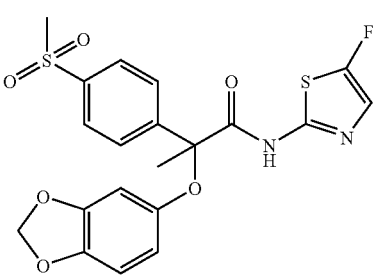 | 2-(Benzo[1,3]dioxol-5-yloxy)-N-(5-fluoro-thiazol-2-yl)-2-(4-methanesulfonyl-phenyl)-propionamide.<br>$^1$H NMR (400 MHz, CDCl$_3$): δ 1.90 (s, 3H), 3.07 (s, 3H), 5.94 (s, 2H), 6.22 (dd, J1 = 2.4 Hz, J = 2.4 Hz, 1H)), 6.32 (d, J = 8.4 Hz, 1H), 6.63 (d, J = 8.4 Hz, 1H), 7.07 (d, J = 2.8 Hz, 2H), 7.80 (d, J = 8.4 Hz, 1H), 8.00 (d, J = 8.4 Hz, 1H) 9.85 (bs, 1H).<br>MS (EI) m/z: 514.90 (M + 1). |

| Example | Structure | IUPAC name and analytical data |
| --- | --- | --- |
| O7 | 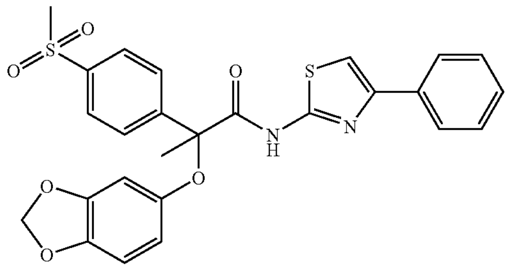 [SMILES: CC(Oc1ccc2c(c1)OCO2)(C(=O)Nc1nc(-c2ccccc2)cs1)c1ccc(S(C)(=O)=O)cc1] | 2-(Benzo[1,3]dioxol-5-yloxy)-2-(4-methanesulfonyl-phenyl)-N-(4-phenyl-thiazol-2-yl)-propionamide.<br>$^1$H NMR (400 MHz, CDCl$_3$): δ 1.95 (s, 3H), 3.07 (s, 3H), 5.94 (s, 2H), 6.28 (dd, J1 = 2.4 Hz, J = 2.4 Hz, 1H)), 6.35 (d, J = 2.4 Hz, 1H), 6.63 (d, J = 8.4 Hz, 1H), 7.47-7.49 (m, 3H), 7.85 (d, J = 8.4 Hz, 2H), 7.91-7.93 (m, 2H), 8.01 (d, J = 8.4 Hz, 2H), 10.41 (bs, 1H).<br>MS (EI) m/z: 523.80 (M + 1). |
| O8 | 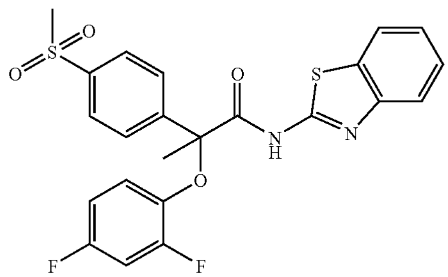 [SMILES: CC(Oc1ccc(F)cc1F)(C(=O)Nc1nc2ccccc2s1)c1ccc(S(C)(=O)=O)cc1] | N-Benzothiazol-2-yl-2-(2,4-difluorophenoxy)-2-(4-methanesulfonyl-phenyl)-propionamide.<br>$^1$H NMR (400 MHz, CDCl$_3$): δ 1.95 (s, 3H), 3.02 (s, 3H), 6.70 (m, 2H), 6.95 (m, 1H), 7.37 (m, 1H), 7.47 (m, 1H), 7.85 (m, 4H), 8.02 (d, J = 8.8 Hz, 2H), 10.25 (bs, 1H).<br>MS (EI) m/z: 489.00 (M + 1). |
| O9 | 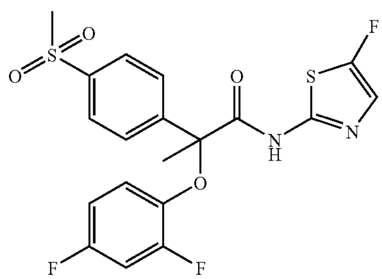 [SMILES: CC(Oc1ccc(F)cc1F)(C(=O)Nc1ncc(F)s1)c1ccc(S(C)(=O)=O)cc1] | 2-(2,4-Difluoro-phenoxy)-N-(5-fluoro-thiazol-2-yl)-2-(4-methanesulfonyl-phenyl)-propionamide.<br>$^1$H NMR (400 MHz, CDCl$_3$): δ 1.87 (s, 3H), 3.08 (s, 3H), 6.62-6.71 (m, 2H), 6.91-6.95 (m, 1H), 7.07 (d, J = 2.8 Hz, 1H), 7.83 (d, J = 8.8 Hz, 2H), 8.02 (d, J = 8.8 Hz, 2H), 9.99 (bs, 1H).<br>MS (EI) m/z: 456.70 (M + 1). |
| O10 | 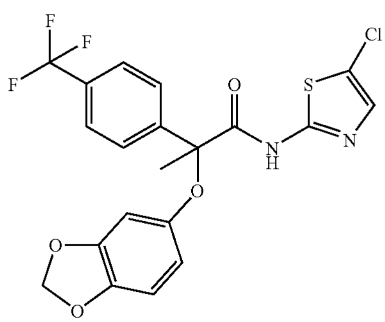 [SMILES: CC(Oc1ccc2c(c1)OCO2)(C(=O)Nc1ncc(Cl)s1)c1ccc(C(F)(F)F)cc1] | 2-(Benzo[1,3]dioxol-5-yloxy)-N-(5-chloro-thiazol-2-yl)-2-(4-trifluoromethyl-phenyl)-propionamide.<br>$^1$H NMR (400 MHz, CDCl$_3$): δ 1.91 (s, 3H), 5.95 (s, 2H), 6.25-6.27 (dd, J = 2.4, 8 Hz, 1H), 6.34 (d, J = 3.2 Hz, 1H), 6.65 (d, J = 8.8 Hz, 1H), 7.32 (s, 1H), 7.69 (d, J = 8.8 Hz, 2H), 7.73 (d, J = 8.8 Hz, 2H), 10.10 (s, 1H).<br>MS (EI) m/z: 470.7 (M + 1). |
| O11 | 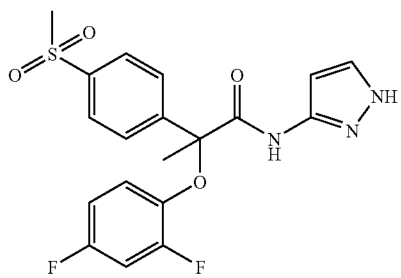 [SMILES: CC(Oc1ccc(F)cc1F)(C(=O)Nc1cc[nH]n1)c1ccc(S(C)(=O)=O)cc1] | 2-(2,4-Difluoro-phenoxy)-2-(4-methanesulfonyl-phenyl)-N-(1H-pyrazol-3-yl)-propionamide.<br>$^1$H NMR (400 MHz, CDCl$_3$): δ 1.75 (s, 3H), 3.23 (s, 3H), 6.51 (bs, 1H), 6.78-7.07 (m, 4H) 7.34 (bs, 1H), 7.55 (bs, 1H), 7.94-8.00 (m, 5H).<br>MS (EI) m/z: 422.00 (M + 1). |

| Example | Structure | IUPAC name and analytical data |
| --- | --- | --- |
| O12 | 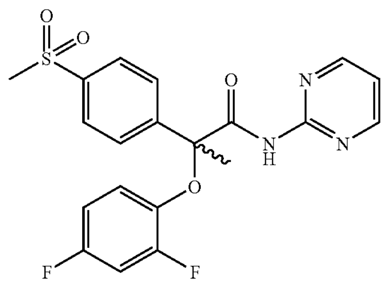 [SMILES: CC(Oc1ccc(F)cc1F)(C(=O)Nc1ncccn1)c1ccc(S(C)(=O)=O)cc1] | 2-(2,4-Difluoro-phenoxy)-2-(4-methanesulfonyl-phenyl)-N-pyrimidin-2-yl-propionamide.<br>$^1$H NMR (400 MHz, CDCl$_3$): 1.88 (s, 3H), 3.06 (s, 3H), 6.71-6.76 (m, 2H), 6.91-6.97 (m, 1H), 7.09-7.12 (m, 1H), 7.93 (d, J = 8.4 Hz, 2H), 7.99 (d, J = 8.4 Hz, 2H), 8.67 (d, J = 4.8 Hz, 2H), 9.61 (s, 1H).<br>MS (EI) m/z: 434.0 (M + 1). |
| O13 | 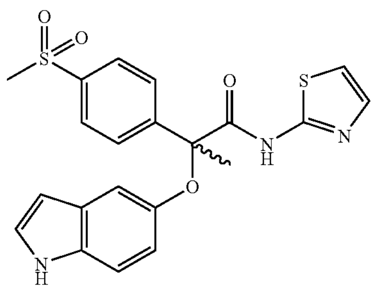 [SMILES: CC(Oc1ccc2[nH]ccc2c1)(C(=O)Nc1nccs1)c1ccc(S(C)(=O)=O)cc1] | 2-(1H-Indol-5-yloxy)-2-(4-methanesulfonyl-phenyl)-N-thiazol-2-yl-propionamide.<br>$^1$H NMR (400 MHz, CDCl$_3$): 1.89 (s, 3H), 3.05 (s, 3H), 6.43-6.44 (m, 1H), 6.70-6.73 (m, 1H), 7.02-7.04 (m, 2H), 7.21-7.23 (m, 1H), 7.50 (d, J = 3.6 Hz, 1H), 7.91 (d, J = 8.4 Hz, 2H), 7.99 (d, J = 8.4 Hz, 2H), 8.15 (s, 1H), 10.39 (s, 1H).<br>MS (EI) m/z: 442.00 (M + 1). |
| O14 | 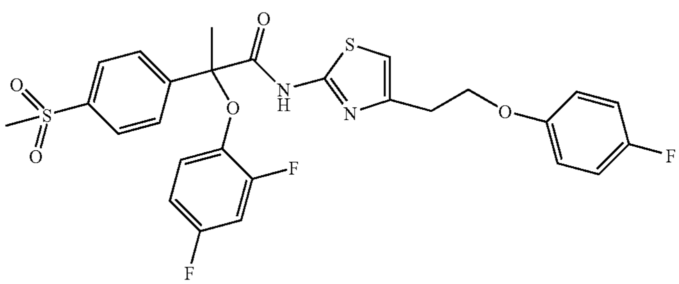 [SMILES: CC(Oc1ccc(F)cc1F)(C(=O)Nc1nc(CCOc2ccc(F)cc2)cs1)c1ccc(S(C)(=O)=O)cc1] | 2-(2,4-Difluoro-phenoxy)-N-{4-[2-(4-fluoro-phenoxy)-ethyl]-thiazol-2-yl}-2-(4-methanesulfonyl-phenyl)-propionamide<br>$^1$H NMR: (400 MHz, CDCl3): δ 1.89 (s, 3H), 3.08 (s, 3H), 3.15 (t, 2H), 4.25 (t, 2H), 6.65-6.72 (m, 2H), 6.78 (s, 1H), 6.83-6.86 (m, 2H), 6.92-6.99 (m, 3H), 6.86 (d, 2H, J = 8 Hz); 8.02 (d, 2H, J = 8 Hz), 10.1 (brs, 1H).<br>MS (EI) m/z: 577 (M + 1). |
| O15 | 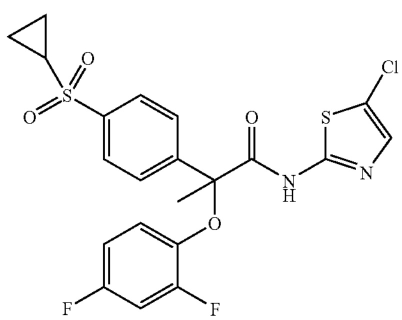 [SMILES: CC(Oc1ccc(F)cc1F)(C(=O)Nc1ncc(Cl)s1)c1ccc(S(=O)(=O)C2CC2)cc1] | N-(5-Chloro-thiazol-2-yl)-2-(4-cyclopropanesulfonyl-phenyl)-2-(2,4-difluoro-phenoxy)-propionamide.<br>$^1$H NMR (400 MHz, CDCl$_3$): δ 1.06-1.08 (m, 2H), 1.36-1.39 (m, 2H), 1.88 (s, 3H), 2.47 (m, 1H), 6.61-6.63 (m, 1H), 6.70-6.71 (m, 1H), 6.93 (m, 1H), 7.33 (s, 1H), 7.81 (d, J = 8.4 Hz, 2H), 7.96 (d, J = 8.4 Hz, 2H), 10.12 (s, 1H).<br>MS (EI) m/z: 499.0 (M + 1). |
| O16 | 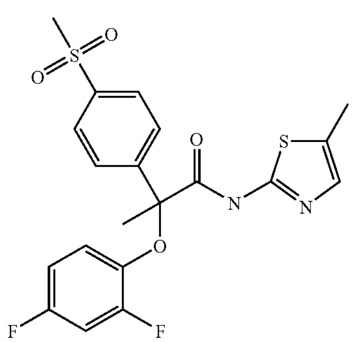 [SMILES: Cc1cnc(NC(=O)C(C)(Oc2ccc(F)cc2F)c2ccc(S(C)(=O)=O)cc2)s1] | 2-(2,4-Difluoro-phenoxy)-2-(4-methanesulfonyl-phenyl)-N-(5-methyl-thiazol-2-yl)-propionamide<br>1HNMR (400 MHz, CDCl3), δ 1.87 (s, 3H), 2.41 (s, 3H), 3.07 (s, 3H), 6.63-6.70 (m, 2H), 6.90-6.95 (m, 1H), 7.13 (s, 1H), 7.85 (d, J = 8.4 Hz, 2H), 8.00 (d, J = 8.4 Hz, 2H), 10.19 (bs, 1H).<br>MS (EI) m/z: 453.00 (M + 1). |

| Example | Structure | IUPAC name and analytical data |
|---|---|---|
| O17 | 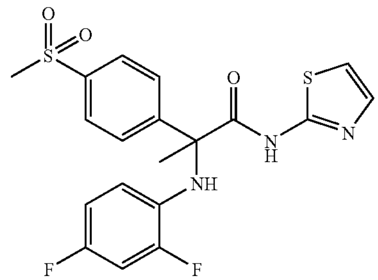 [SMILES: CC(Nc1ccc(F)cc1F)(C(=O)Nc1nccs1)c1ccc(S(C)(=O)=O)cc1] | 2-(2,4-Difluoro-phenylamino)-2-(4-methanesulfonyl-phenyl)-N-thiazol-2-yl-propionamide.<br>$^1$H NMR (400 MHz, CDCl$_3$): δ 1.97 (s, 3H), 3.06 (s, 3H), 4.85 (s, 1H), 6.22-6.27 (m, 1H), 6.56-6.61 (m, 1H), 6.84-6.89 (m, 1H), 7.03-7.04 (d, J = 3.6 Hz, 1H), 7.42-7.43 (d, J = 3.6 Hz, 1H), 7.86-7.88 (d, J = 8.8 Hz, 2H), 7.96-7.98 (d, J = 8.4 Hz, 2H), 10.46 (bs, 1H).<br>MS (EI) m/z: (M + 1). |
| O18 | 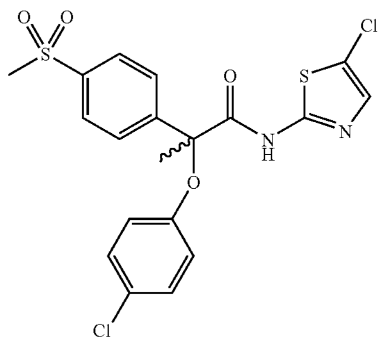 [SMILES: CC(Oc1ccc(Cl)cc1)(C(=O)Nc1ncc(Cl)s1)c1ccc(S(C)(=O)=O)cc1] | 2-(4-Chloro-phenoxy)-N-(5-chloro-thiazol-2-yl)-2-(4-methanesulfonyl-phenyl)-propionamide.<br>$^1$H NMR (400 MHz, CDCl$_3$): δ 1.90 (s, 3H), 3.08 (s, 3H), 6.72 (d, J = 9.2 Hz, 2H), 7.21 (d, J = 9.2 Hz, 2H), 7.31 (s, 1H), 7.80 (d, J = 8.8 Hz, 2H), 8.00 (d, J = 8.4 Hz, 2H), 10.00 (s, 1H).<br>MS (EI) m/z: 471.0 (M + 1). |
| O19 | 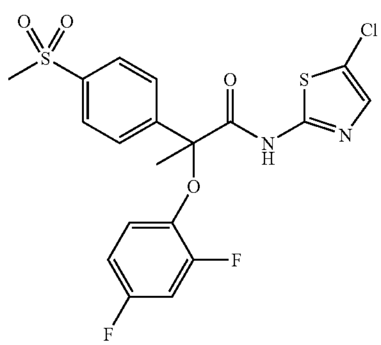 [SMILES: CC(Oc1ccc(F)cc1F)(C(=O)Nc1ncc(Cl)s1)c1ccc(S(C)(=O)=O)cc1] | N-(5-Chloro-thiazol-2-yl)-2-(2,4-difluorophenoxy)-2-(4-methanesulfonyl-phenyl)-propionamide<br>$^1$H NMR (400 MHz, CDCl$_3$): δ 1.90 (s, 3H), 3.08 (s, 3H), 6.63-6.66 (m, 1H), 6.69-6.71 (m, 1H), 6.91-6.96 (m, 1H), 7.33 (s, 1H), 7.84 (d, J = 8.4 Hz, 2H), 8.02 (d, J = 8.8 Hz, 2H), 10.20 (s, 1H).<br>MS (EI) m/z: 472.90 (M + 1). |
| O20 | 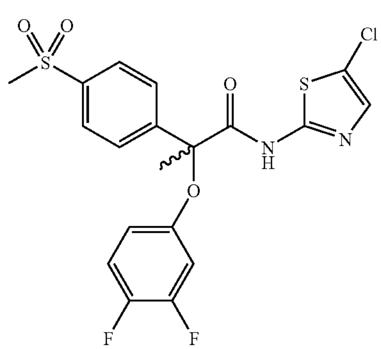 [SMILES: CC(Oc1ccc(F)c(F)c1)(C(=O)Nc1ncc(Cl)s1)c1ccc(S(C)(=O)=O)cc1] | N-(5-Chloro-thiazol-2-yl)-2-(3,4-difluoro-phenoxy)-2-(4-methanesulfonyl-phenyl)-propionamide<br>MS (EI) m/z: 473.0 (M + 1). |

Synthesis Type-P

Example P1

{5-Chloro-2-[2-(2,4-difluoro-phenoxy)-2-(4-methanesulfonyl-phenyl)-propionylamino]-thiazol-4-yl}-acetic acid

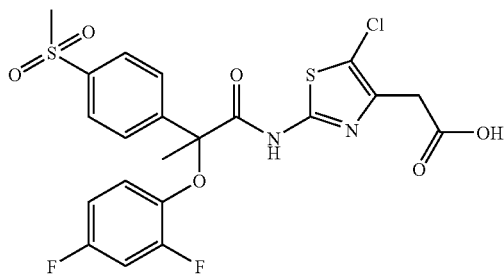 [SMILES: CC(Oc1ccc(F)cc1F)(C(=O)Nc1nc(CC(=O)O)c(Cl)s1)c1ccc(S(C)(=O)=O)cc1]

To a solution of {5-Chloro-2-[2-(2,4-difluoro-phenoxy)-2-(4-methanesulfonyl-phenyl)-propionylamino]-thiazol-4-yl}-acetic acid methyl ester (0.03 g, 0.05 mmol) in THF: Ethanol:water (1 ml+0.3 ml+0.3 ml) was added lithium hydroxide (0.0046 g, 0.11 mmol). The resulting mixture was stirred for 5 hours at room temperature followed by removal of solvent under reduced pressure. The residue was suspended in water (15 ml), extracted with ethyl acetate to remove impurities. The aqueous layer was acidified with 1N HCl (0.5 ml) and extracted with ethyl acetate (2×10 ml), This ethyl acetate layer was washed with water (15 ml), brine (20 ml), dried over anhydrous sodium sulfate and solvent was removed under reduced pressure to give solid product {5-Chloro-2-[2-(2,4-difluoro-phenoxy)-2-(4-methanesulfonyl-phenyl)-propionylamino]-thiazol-4-yl}-acetic acid (9 mg). $^1$H NMR (400 MHz, CDCl$_3$): δ 1.85 (s, 3H), 3.07 (s, 3H), 3.72 (s, 2H), 6.64-6.69 (m, 2H), 6.89-6.91 (m, 1H), 7.84 (d, J=8.4 Hz, 2H), 8.00 (d, J=8.8 Hz, 2H). MS (EI) m/z: 530.70 (M+1), mp: 109-111° C.

Preparation of {5-Chloro-2-[2-(2,4-difluoro-phenoxy)-2-(4-methanesulfonyl-phenyl)-propionylamino]-thiazol-4-yl}-acetic acid methyl ester used in Example P1

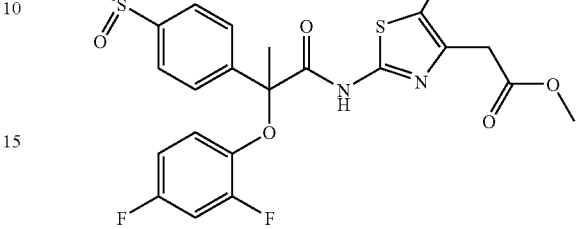

To a mixture of 2-(2,4-Difluoro-phenoxy)-2-(4-methanesulfonyl-phenyl)-propionic acid (0.110 g, 0.22 mmol), (2-Amino-5-chloro-thiazol-4-yl)-acetic acid methyl ester (0.071 g, 0.32 mmol), HOBt (0.052 g, 0.38 mmol), and EDCI (0.074 g, 0.38 mmol) in methylene dichloride (10 ml) was added N-methylmorpholine (0.039 g, 0.38 mmol). The resulting mixture was stirred at room temperature for overnight followed by dilution with 10 ml methylene dichloride. The reaction mixture was poured onto water (20 ml), and organic layer separated, washed with water (2×20 ml), brine (20 ml), dried over sodium sulfate and solvent evaporated to get residue which was purified by preparative TLC using 50% ethyl acetate in hexane as mobile. To give desired compound (0.30 g). $^1$H NMR (400 MHz, CDCl$_3$): δ 1.45 (t, J=7.2 Hz, 3H), 1.93 (s, 3H), 3.14 (s, 3H), 3.77 (d, J=2.8 Hz, 1H), 4.26 (q, J=7.2 Hz, 1H), 6.69-6.77 (m, 2H), 6.96-7.02 (m, 1H), 7.89 (d, J=8.4 Hz, 2H), 8.07 (d, J=8.4 Hz, 1H); MS (D) m/z: 559.00 (M+1).

The following compounds were prepared in an analogous manner of Example P1 from the appropriate intermediates:

| Example | Structure | IUPAC name and analytical data |
|---|---|---|
| P2 | 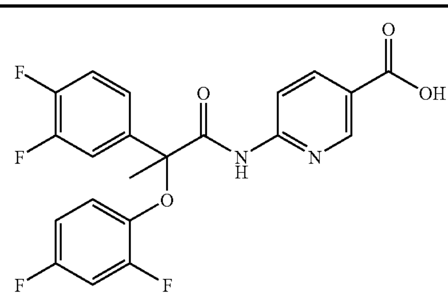 | 6-[2-(2,4-Difluoro-phenoxy)-2-(3,4-difluoro-phenyl)-propionylamino]-nicotinic acid. $^1$H NMR (400 MHz, CDCl$_3$): 1.85 (s, 3H), 6.66-6.70 (m, 2H), 6.89-6.92 (m, 1H), 7.20-7.23 (m, 1H), 7.36-7.39 (m, 1H), 7.45-7.55 (m, 1H), 8.33-8.37 (m, J = 8.8 Hz, 2.0 Hz, 2H), 9.01-9.01 (d, J = 1.6 Hz, 1H), 9.79 (bs, 1H). MS (EI) m/z: 434.8 (M + 1). |
| P3 | 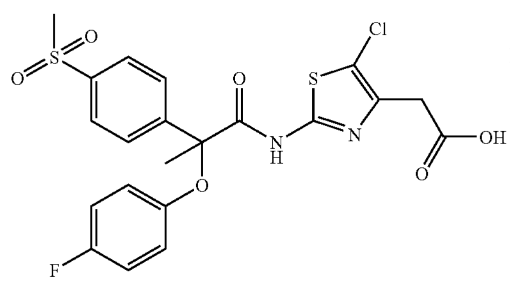 [SMILES: CC(Oc1ccc(F)cc1)(C(=O)Nc1nc(CC(=O)O)c(Cl)s1)c1ccc(S(C)(=O)=O)cc1] | {5-Chloro-2-[2-(4-fluoro-phenoxy)-2-(4-methanesulfonyl-phenyl)-propionylamino]-thiazol-4-yl}-acetic acid. $^1$H NMR (400 MHz, CDCl$_3$): δ 1.95 (s, 3H), 3.08 (s, 3H), 6.70-6.73 (m, 2H), 7.07 (d, J = 3.2 Hz, 1H), 7.19-7.22 (m, 2H), 7.79-7.81 (m, 2H), 7.99-7.01 (m, 2H), 9.90 (bs, 1H). MS (EI) m/z: (M + 1). |

| Example | Structure | IUPAC name and analytical data |
|---|---|---|
| P4 | 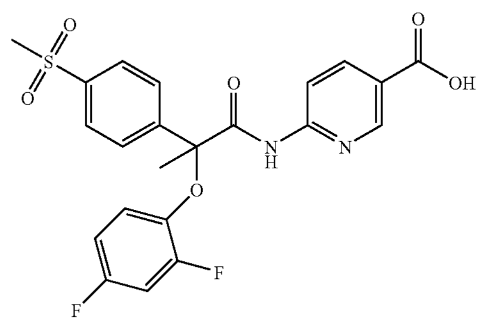 [SMILES: CC(Oc1ccc(F)cc1F)(C(=O)Nc1ccc(C(=O)O)cn1)c1ccc(S(C)(=O)=O)cc1] | 6-[2-(2,4-Difluoro-phenoxy)-2-(4-methanesulfonyl-phenyl)-propionylamio]-nicotinic acid<br>$^1$HNMR (400 MHz, CDCl$_3$): δ 1.89 (s, 3H), 3.08 (s, 3H), 6.67-6.72 (m, 2H), 6.91-6.94 (m, 1H), 7.88-7.91 (m, 2H), 8.00-8.03 (m, 2H), 8.31-8.39 (m, 2H 9.01 (s, 1H), 9.78 (s, 1H).<br>MS (EI) m/z: 477.10 (M + 1). |
| P5 | 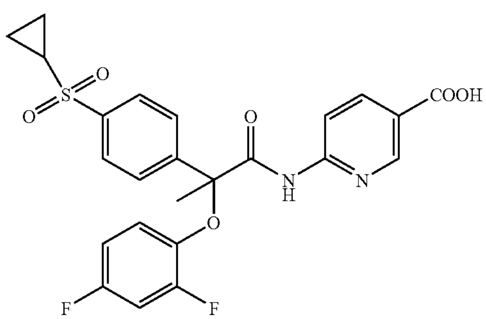 [SMILES: CC(Oc1ccc(F)cc1F)(C(=O)Nc1ccc(C(=O)O)cn1)c1ccc(S(=O)(=O)C2CC2)cc1] | 6-[2-(4-Cyclopropanesulfonyl-phenyl)-2-(2,4-difluoro-phenoxy)-propionylamino]-nicotinic acid.<br>$^1$H NMR (400 MHz, CDCl$_3$): 1.05-1.08 (m, 2H), 1.36-1.40 (m, 2H), 1.89 (s, 3H), 2.45-2.49 (m, 1H), 6.66-6.71 (m, 2H), 6.91-6.96 (m, 1H), 7.87 (d, J = 8.4 Hz, 2H), 7.97 (d, J = 8.4 Hz, 2H), 8.33 (d, J = 8.4 Hz, 1H), 8.37-8.39 (m, 1H), 9.02 (d, J = 1.6 Hz, 1H), 9.75 (bs, 1H);<br>MS (ES+) m/z 503.1 (M + 1)<br>MS (EI) m/z: 503.10 (M + 1). |

The below list of examples, but not to be limited to these numbers, can also be synthesized following the general synthesis described above:

2-methyl-N-(thiazol-2-yl)-2-(benzothiophen-5-yloxy)propionamide;
2-(benzoxazin-6-yloxy)-2-methyl-N-(thiazol-2-yl)-propionamide;
N-(5-Chloro-thiazol-2-yl)-2-methyl-2-[2-(2-thiophen-2-yl-ethoxy)-phenoxy]-propionamide;
2-(1H-Indol-5-yloxy)-2-methyl-N-thiazol-2-yl-propionamide;
2-(Biphenyl-4-yloxy)-2-methyl-N-thiazol-2-yl-propionamide;
2-(Indan-5-yloxy)-2-methyl-N-thiazol-2-yl-propionamide;
2-(3,4-Difluoro-phenoxy)-N-isoxazol-3-yl-2-methyl-propionamide;
2-(2,4-Difluoro-phenoxy)-2-methyl-N-(4-methyl-pyrimidin-2-yl)-propionamide;
2-Methyl-2-(3-oxo-3,4-dihydro-2H-benzo[1,4]oxazin-7-yloxy)-N-thiazol-2-yl-propionamide;
6-[2-Methyl-2-(3-oxo-3,4-dihydro-2H-benzo[1,4]oxazin-7-yloxy)-propionylamino]-nicotinic acid methyl ester;
{2-[2-(Benzo[1,3]dioxol-5-yloxy)-2-methyl-propionylamino]-thiazol-4-yl}-acetic acid;
{2-[2-(2,4-Difluoro-phenoxy)-2-methyl-propionylamino]-thiazol-4-yl}-acetic acid;
2-[2-(2,4-Difluoro-phenoxy)-2-methyl-propionylamino]-thiazole-4-carboxylic acid;
2-[2-(Benzo[1,3]dioxol-5-yloxy)-2-methyl-propionylamino]-5-chloro-thiazole-4-carboxylic acid;
2-[2-(Benzo[1,3]dioxol-5-yloxy)-2-methyl-propionylamino]-thiazole-4-carboxylic acid;
5-Chloro-2-[2-(2,4-difluoro-phenoxy)-2-methyl-propionylamino]-thiazole-4-carboxylic acid;
{2-[2-(Benzo[1,3]dioxol-5-yloxy)-2-methyl-propionylamino]-5-chloro-thiazol-4-yl}-acetic acid;
{2-[2-Methyl-2-(naphthalen-2-yloxy)-propionylamino]-thiazol-4-yl}-acetic acid;
{5-Chloro-2-[2-(4-chloro-phenoxy)-2-methyl-propionylamino]-thiazol-4-yl}-acetic acid;
{5-Chloro-2-[2-(3,4-difluoro-phenoxy)-2-methyl-propionylamino]-thiazol-4-yl}-acetic acid;
6-[2-(4-Chloro-phenoxy)-2-methyl-propionylamino]-nicotinic acid;
{2-[2-(4-Methanesulfonyl-phenoxy)-2-methyl-propionylamino]-thiazol-4-yl}-acetic acid;
{2-[2-(4-tert-Butyl-phenoxy)-2-methyl-propionylamino]-5-chloro-thiazol-4-yl}-acetic acid;
2-{[1-(4-Methanesulfonyl-phenoxy)-cyclohexanecarbonyl]-amino}-thiazole-4-carboxylic acid
2-(4-Chloro-phenoxy)-N-(5-chloro-thiazol-2-yl)-2-methyl-4-thiophen-2-yl-butyramide;
{2-[2-(4-Chloro-phenoxy)-3-cyclopentyl-2-methyl-propionylamino]-thiazol-4-yl}-acetic acid;
3-{5-Chloro-2-[2-(2,4-difluoro-phenoxy)-2-methyl-propionylamino]-thiazol-4-yl}-propionic acid;
{2-[2-(4-Acetylamino-phenoxy)-2-methyl-propionylamino]-5-chloro-thiazol-4-yl}-acetic acid.
2-Methyl-N-thiazol-2-yl-2-[4-(2-thiophen-2-yl-ethylamino)-phenoxy]-propionamide;
N-(5-Chloro-thiazol-2-yl)-2-methyl-2-{4-[2-(4-trifluoromethyl-phenyl)-ethylamino]-phenoxy}-propionamide
2-[2-(2,4-Difluoro-phenoxy)-2-methyl-propionylamino]-thiazole-4-carboxylic acid (4-fluoro-phenyl)-amide;
6-[2-(Benzo[1,3]dioxol-5-yloxy)-2-methyl-propionylamino]-N-(4-fluoro-phenyl)-nicotinamide;
2-(Benzo[1,3]dioxol-5-yloxy)-N-{5-chloro-4-[(4-fluoro-phenylcarbamoyl)-methyl]-thiazol-2-yl}-2-methyl-propionamide;
N-{4-[(2,4-Difluoro-phenylcarbamoyl)-methyl]-thiazol-2-yl}-2-(1H-indol-5-yloxy)-2-methyl-propionamide;

{4-[1-(5-Chloro-thiazol-2-ylcarbamoyl)-1-methyl-ethoxy]-3-fluoro-phenyl}-acetic acid
2-(Benzo[1,3]dioxol-5-yloxy)-N-{4-[2-(4-fluoro-phenoxy)-ethyl]-thiazol-2-yl}-2-methyl-propionamide
2-(4-Chloro-phenylsulfanyl)-2-(4-methanesulfonyl-phenyl)-N-thiazol-2-yl-propionamide;
2-(2,4-Difluoro-phenoxy)-2-(4-methanesulfonyl-phenyl)-N-(4-phenyl-thiazol-2-yl)-propionamide;
2-(2,4-Difluoro-phenoxy)-2-(4-methanesulfonyl-phenyl)-N-(5-phenyl-[1,3,4]thiadiazol-2-yl)-propionamide;
2-(2,4-Difluoro-phenoxy)-N-(6-fluoro-benzothiazol-2-yl)-2-(4-methanesulfonyl-phenyl)-propionamide;
N-(4-Chloro-benzothiazol-2-yl)-2-(2,4-difluoro-phenoxy)-2-(4-methanesulfonyl-phenyl)-propionamide;
N-(6-Chloro-benzothiazol-2-yl)-2-(2,4-difluoro-phenoxy)-2-(4-methanesulfonyl-phenyl)-propionamide;
2-(2,4-Difluoro-phenoxy)-2-(4-methanesulfonyl-phenyl)-N-(4-methyl-pyrimidin-2-yl)-propionamide;
2-(4-(tetrahydropyran-4-ylsulfonyl)phenyl)-2-(2,4-difluoro-phenoxy)-N-(5-fluoro-thiazol-2-yl)-propionamide;
2-(2,4-Difluoro-phenoxy)-2-(4-methanesulfonyl-phenyl)-N-pyrazin-2-yl-propionamide;
2-[3-Chloro-4-((cyclopentanon-3-yl)sulfonyl-phenyl)-2-(2,4-difluoro-phenoxy)-N-(5-fluoro-thiazol-2-yl]-propionamide;
2-[2-(2,4-Difluoro-phenoxy)-2-(4-methanesulfonyl-phenyl)-propionylamino]-4-methyl-thiazole-5-carboxylic acid;
6-[2-(2,5-Difluoro-phenoxy)-2-(4-trifluoromethyl-phenyl)-propionylamino]-nicotinic acid;
3-{2-[2-(2,4-Difluoro-phenoxy)-2-(4-methanesulfonyl-phenyl)-propionylamino]-thiazol-4-yl}-propionic acid;
3-{2-[2-(2,4-Difluoro-phenoxy)-2-methyl-propionylamino]-thiazol-4-yl}-propionic acid;
{2-[2-(6-Chloro-pyridin-3-yloxy)-2-(4-methanesulfonyl-phenyl)-propionylamino]-5-fluoro-thiazol-4-yl}-acetic acid;
{2-[2-(4-Cyclopentanesulfonyl-phenyl)-2-(2,4-difluoro-phenoxy)-propionylamino]-5-fluoro-thiazol-4-yl}-acetic acid;
{2-[2-(6-Chloro-pyridin-3-yloxy)-2-(4-cyclopropanesulfonyl-phenyl)-propionylamino]-5-fluoro-thiazol-4-yl}-acetic acid;
{2-[2-(4-Cyclohexanesulfonyl-phenyl)-2-(2,4-difluoro-phenoxy)-propionylamino]-5-fluoro-thiazol-4-yl}-acetic acid;

Measurement of Glucokinase Activity:

Glucokinase (GK) activity, in vitro, has been measured using a coupled enzymatic assay (Ref: Hariharan et al (1997) Diabetes 46: 11-16). GK catalyzes the first step, the conversion of glucose to glucose-6-phosphate (G6P) in the presence of ATP. G6P in turn is converted by glucose-6-phosphate dehydrogenase (G6PD) to 6-phosphogluconate, a process that requires NAD, resulting in NADH formation. Since the GK-catalyzed step is the rate-limiting step of this coupled enzymatic process, the rate of accumulation of 6-phosphogluconate and NADH is directly proportional to the rate of glucose phosphorylation by GK. The rate of the GK-catalyzed reaction can therefore be measured by monitoring the increase in NADH absorbance at 340 nm.

The assay is carried out according to the protocol outlined in Hariharan et al (1997), Diabetes 46: 11-16. Briefly, the test compounds are incubated in a reaction mix containing 25 mM HEPES (pH 7.2), 10 mM $MgCl_2$, 100 mM KCl, 5 mM ATP, 2 mM DTT, 0.5 mM NAD, 1 U/ml *Leuconostoc mesenteroides* G6PD, 0.3 U/ml of purified human recombinant GK, and different concentrations of glucose. Enzymatic activity is calculated from the initial reaction velocity, measured from the change in NADH absorbance as a function of time.

Compounds described in formula (I), in concentration ranges from 1.0 nM to 500 μM, are tested in purified human recombinant Glucokinase assay described above.

A compound is considered to be a glucokinase activator if it, in its testable range of concentrations, yields a higher rate of glucose phosphorylation than in its absence.

The Glucokinase activation data of some representative compounds of the present invention, which are illustrative but not to be construed as limiting the scope or spirit of the invention, are given in the table 1 below.

TABLE 1

Glucokinase activation ($EC_{50}$ values for GK activation at 5 mM Glucose conc) data

| Example | Structure | $EC_{50}$ (μM) |
|---------|-----------|----------------|
| J1 | 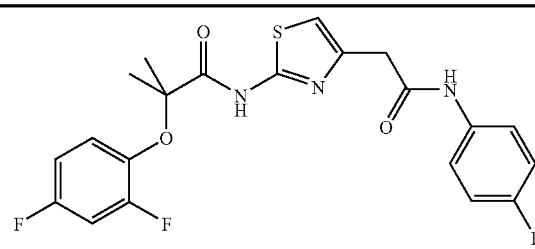 | 4.5 |
| A10 | 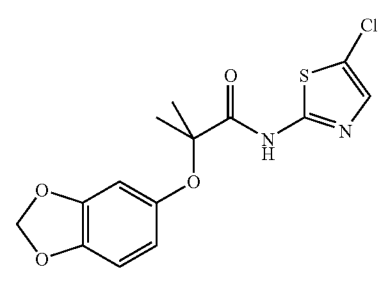 [SMILES: CC(C)(Oc1ccc2c(c1)OCO2)C(=O)Nc1ncc(Cl)s1] | 2.2 |

TABLE 1-continued

Glucokinase activation (EC$_{50}$ values for GK activation at 5 mM Glucose conc) data

| Example | Structure | EC$_{50}$ (μM) |
|---|---|---|
| A11 | 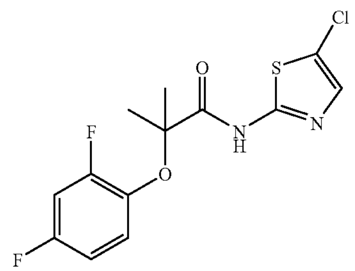 [SMILES: CC(C)(Oc1ccc(F)cc1F)C(=O)Nc1ncc(Cl)s1] | 1.8 |
| A27 | 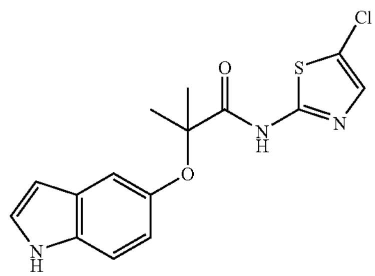 [SMILES: CC(C)(Oc1ccc2[nH]ccc2c1)C(=O)Nc1ncc(Cl)s1] | 7.0 |
| G7 | 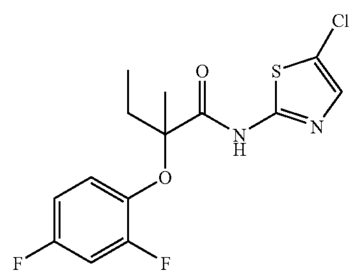 [SMILES: CCC(C)(Oc1ccc(F)cc1F)C(=O)Nc1ncc(Cl)s1] | 7.1 |
| P1 | 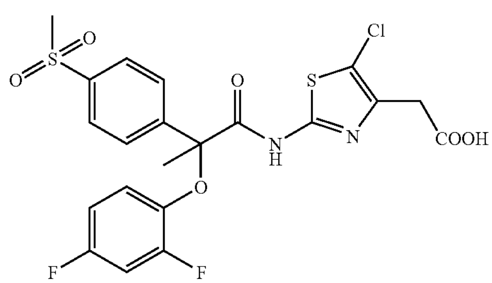 [SMILES: CC(Oc1ccc(F)cc1F)(C(=O)Nc1nc(CC(=O)O)c(Cl)s1)c1ccc(S(C)(=O)=O)cc1] | 7.0 |
| P4 | 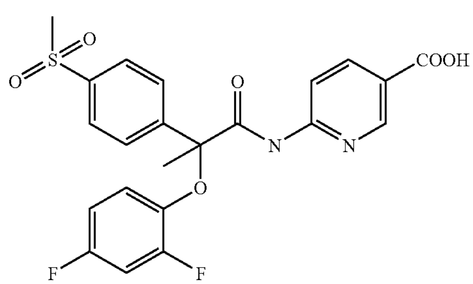 [SMILES: CC(Oc1ccc(F)cc1F)(C(=O)Nc1ccc(C(=O)O)cn1)c1ccc(S(C)(=O)=O)cc1] | >14 |

TABLE 1-continued

Glucokinase activation (EC$_{50}$ values for GK activation at 5 mM Glucose conc) data

| Example | Structure | EC$_{50}$ (µM) |
|---------|-----------|----------------|
| O15 | [Structure] | 1.8 |
| O16 | [Structure] | 5.4 |

Measurement of Glycogen Synthesis in Primary Rat Hepatocytes:

Primary hepatocytes are collected from male Wistar rats, and tested for viability by trypan blue exclusion. Primary hepatocytes cultures with viability greater than 95% are selected for the glycogen synthesis assay. The cells are seeded in a 48-well plate at a density of 200,000 cells/well in 250 µl Minimal Essential Medium (MEM) containing 10% foetal calf serum (FCS) and 1.7 µM insulin, and incubated for 4 hours at 37° C. to allow attachment. The medium is replaced with fresh MEM containing 10% FCS, 1.7 µM insulin and 10 nM dexamethasone, and the cells are incubated for 16 hours at 37° C. The medium is then replaced with fresh MEM (serum-free) containing 2 µCi/ml of D-[U$^{14}$C]-Glucose along with 10 µM of the compound in a final DMSO concentration of 0.1%. The final glucose concentration is brought to 10 mM by the addition of D-Glucose (MEM already contains 5 mM glucose). The cells are incubated for 3 hours at 37° C. The cells are washed twice with 150 mM NaCl, lysed with 0.1 N NaOH, and the lysate precipitated with 8% w/v trichloroacetic acid (TCA) and 1 mg/well unlabeled glycogen as carrier. Cell debris is pelleted by centrifugation, the supernatant is removed, and the glycogen is precipitated with 63% ethanol. After another round of centrifugation, the supernatant is removed, and the pellet containing the precipitated glycogen is dried overnight. De novo synthesized glycogen is estimated in a scintillation counter (MicroBeta Trilux, Perkin Elmer), and expressed as fold increase over DMSO control.

The protocol for the glycogen assay is based on the method described in "Biochem J. 1990 Feb. 15; 266(1): 91-102" with a few minor modifications. The protocol for isolation of primary rat hepatocytes is based on the method described in "Methods in Enzymology, Vol. III. pp 34-50. Ed. by S. P. Colowick and N. O. Kaplan. New York, Academic Press, 1957" with a few minor modifications.

Compounds described in formula (I), in concentration ranges from 1.0 nM to 500 µM, are tested in glycogen synthesis assay described above.

A compound is considered to be a glucokinase activator in a cellular environment if it demonstrates significant increase of glycogen synthesis over DMSO control as described in the above mentioned glycogen synthesis assay.

The glycogen synthesis data of some representative compounds of the present invention, which are illustrative but not limiting, is given in the table 2 below.

TABLE 2

Glycogen synthesis data

| Example No. | Structure | Fold increase in glycogen synthesis at 10 µM Compound |
|---|---|---|
| A17 | *(structure: indole-O-C(CH₃)₂-C(O)NH-thiazole-Cl)* | 2.9 |
| P5 | *(structure: cyclopropylsulfonyl-phenyl-C(CH₃)(O-2,4-difluorophenyl)-C(O)NH-pyridine-COOH)* | 3.2 |

Characterization of Partial Glucokinase Activators from In Vitro Glucokinase Assay:

Compounds of interest are tested in GK assay to monitor dose dependent effect on Glucokinase activation (in kinetic mode), as described above, at various glucose concentration. Characterization data of some representative compounds of the present invention, which are illustrative but not limiting, are given here.

Representative dose response curve for Ro-28-1675 and for Examples-A11, O15, J1 are given in FIGS. 1, 3, 4, 5 respectively.

Figure 6:
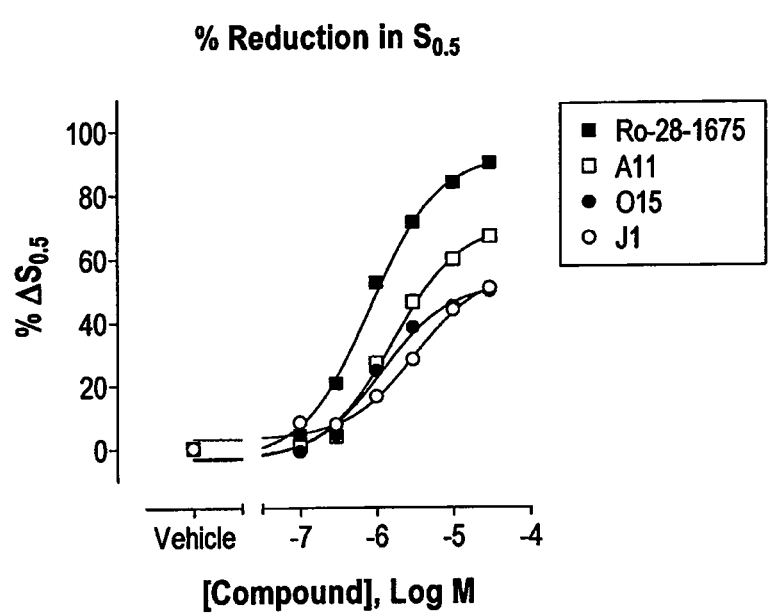
FIG. 6: Dose dependent effect of Examples A11, O15 and J1 on the % $\Delta S_{0.5}$ of glucokinase for glucose—a head to head comparison with Ro-28-1675. The change in the $S_{0.5}$ of glucokinase ($\Delta S_{0.5}$) for glucose in the presence of Examples A11, O15 and J1 is calculated by subtracting the $S_{0.5}$ at each concentration of each Example from the $S_{0.5}$ in the vehicle control. The $\Delta S_{0.5}$ is then normalized to a percent scale, where the $S_{0.5}$ in the vehicle control is set to 0% and 0 mM glucose is set to 100%. The % $\Delta S_{0.5}$ is then plotted against the log of the concentration of each Example. For comparison, the % $\Delta S_{0.5}$ in the presence of Ro-28-1675 is also shown.

The four representative GK activators, mentioned above are further characterized by analyzing secondary plots of %$\Delta S_{0.5}$ values vs. concentration of GK activators (shown in FIG. 6). Now, one can see that Examples-A11, O15, J1 are partial GK activators when compared to Ro-28-1675.

The maximum efficacy ($E_{max}$) and potency ($EC_{50}$) of these partial glucokinase activators and two compounds from literature are listed in Table 3.

TABLE 3

$E_{max}$ and $EC_{50}$ of partial GK activators (measured against % $\Delta S_{0.5}$)

| Example | Structure | $EC_{50}$ (µM) | $E_{max}$(% $\Delta S_{0.5}$) |
|---|---|---|---|
| A11 | *(structure: 2,4-difluorophenyl-O-C(CH₃)₂-C(O)NH-thiazole-Cl)* | 1.25 | 7.0 |

TABLE 3-continued

E*max* and EC$_{50}$ of partial GK activators (measured against % ΔS$_{0.5}$)

| Example | Structure | EC$_{50}$ (μM) | E$_{max}$(% ΔS$_{0.5}$) |
|---|---|---|---|
| O15 | 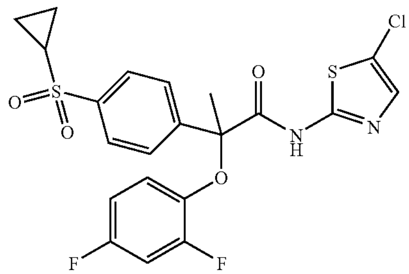 [SMILES: CC(Oc1ccc(F)cc1F)(C(=O)Nc1ncc(Cl)s1)c1ccc(S(=O)(=O)C2CC2)cc1] | 1.2 | 55 |
| J1 | 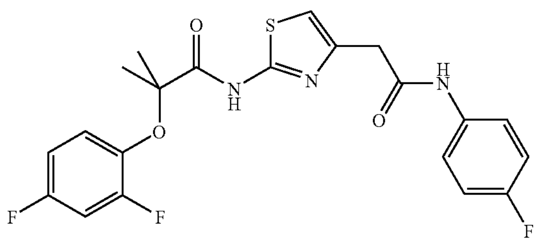 [SMILES: CC(C)(Oc1ccc(F)cc1F)C(=O)Nc1nc(CC(=O)Nc2ccc(F)cc2)cs1] | 3 | 55 |
| Ro-28-1675 | 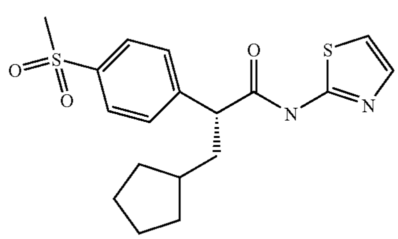 [SMILES: CS(=O)(=O)c1ccc([C@@H](CC2CCCC2)C(=O)Nc2nccs2)cc1] | 0.77 | 90 |
| PSN-GK1 | 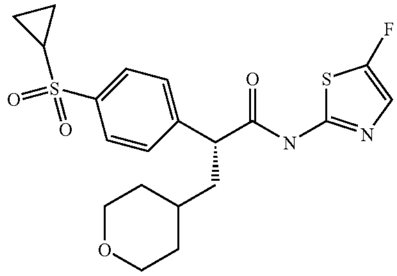 [SMILES: O=C(Nc1ncc(F)s1)[C@H](CC1CCOCC1)c1ccc(S(=O)(=O)C2CC2)cc1] | 0.065 | >95 |

Table 4 briefs some more examples of partial glucokinase activators and their corresponding E$_{max}$ (% ΔS$_{0.5}$) values in glucokinase activation assay.

TABLE 4
Example of partial glucokinase activators and $E_{max}$ values:
| Example | Structure | $E_{max}$(% $\Delta S_{0.5}$) |
|---|---|---|
| A10 | 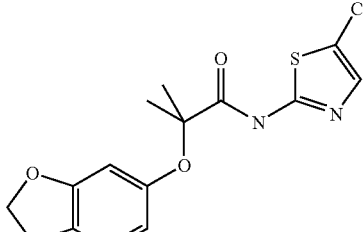 | 75 |
| G7 | 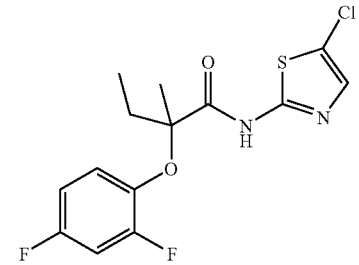 [SMILES: CCC(C)(Oc1ccc(F)cc1F)C(=O)Nc1ncc(Cl)s1] | 60 |
| O18 | 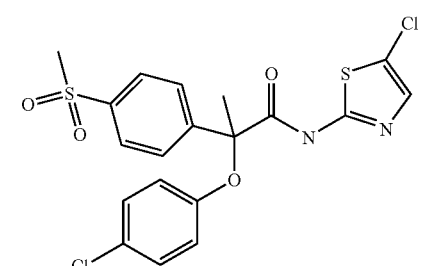 | 60 |
| O19 | 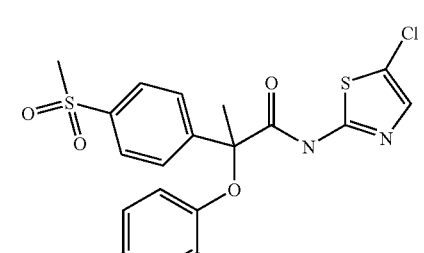 | 75 |
| O20 | 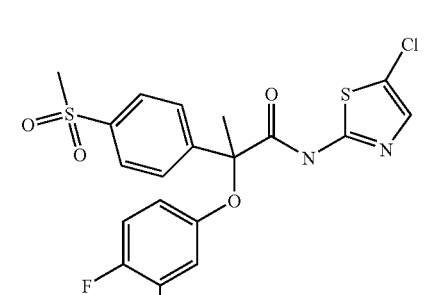 | 50 |

TABLE 4-continued

Example of partial glucokinase activators and $E_{max}$ values:

| Example | Structure | $E_{max}(\% \Delta S_{0.5})$ |
|---|---|---|
| J2 | *[structure: 2-methyl-2-(benzo[d][1,3]dioxol-5-yloxy)propanamide linked to thiazole-acetamide-(4-fluorophenyl)]* | 40 |
| J4 | *[structure: 2-methyl-2-(2,4-difluorophenoxy)propanamide linked to 5-chlorothiazole-acetamide-(4-fluorophenyl)]* | 50 |

Characterization of Partial Glucokinase Activators in Glycogen Synthesis Assay:

Compounds, of interest, are tested in glycogen synthesis assay as described above in concentration ranges from 1.0 nM to 500 µM, The glycogen synthesis data of some representative compounds as partial glucokinase activator of the present disclosure, which are illustrative but not limiting, is given in table 5 below.

TABLE 5

Glycogen synthesis data

| Example No. | Structure; Mass characterization data | Fold increase in glycogen synthesis at 10 µM Compound |
|---|---|---|
| A22 | *[structure: 2-(2,4-difluorophenoxy)-2-methyl-N-(5-fluorothiazol-2-yl)propanamide]* | 2.3 |
| O9 | *[structure: 2-(4-(methylsulfonyl)phenyl)-2-(2,4-difluorophenoxy)-N-(5-fluorothiazol-2-yl)propanamide]* | 2.8 |

TABLE 5-continued

Glycogen synthesis data

| Example No. | Structure; Mass characterization data | Fold increase in glycogen synthesis at 10 μM Compound |
|---|---|---|
| J2 | | 1.8 |
| Ro-28-1675 | | 6.0 |
| PSN-GK1 | | 12.9 |

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A compound of formula (I)

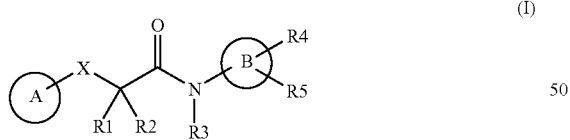

(I)

or its stereoisomer, or a pharmaceutically acceptable salt thereof, wherein,

Ring-A is selected from a group consisting of phenyl, pyridinyl, naphthyl, indolyl, indanyl, and benzodioxolyl;
  wherein said ring A is further substituted with 0 to 4 numbers of substitutions independently selected from a group consisting of alkyl, alkenyl, alkynyl, halo, mono, di or per haloalkyl, nitrile, nitro, oxo, —$NR^6R^7$, —$OR^6$, —$SR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_n(CO)OR^6$, —$(CR^8R^9)_nC(O)R^6$, —$S(O)_p(NR^6)R^7$, cycloalkyl, cycloalkylalkyl, heterocyclyl, heterocycloalkyl, aryl, arylalkyl, heteroaryl, and heteroarylalkyl groups; which are further optionally substituted with common substituents;

p=0-2; n=0-4;

$R^6$ and $R^7$ are independently selected from a group consisting of hydrogen, alkyl, alkenyl, alkynyl, aryl, arylalkyl, heteroaryl, heteroarylalkyl, cycloalkyl, cycloalkylalkyl, heterocyclyl, and heterocyclylalkyl, and further substituted with common substituents;

$R^8$ and $R^9$ are independently selected from a group consisting of hydrogen, fluorine, $OR^6$, alkyl, and perfluoroalkyl;

X is selected from a group consisting of O and $NR^6$;
  wherein $R^6$ is as described above;
  with a proviso that, X is not connected to another heteroatom from ring-A;

$R^1$ and $R^2$ are independently selected from a group consisting of fluoro, alkyl, aryl, aralkyl, heteroaryl, heteroarylalkyl, heterocyclyl, heterocyclylalkyl, cycloalkyl, and cycloalkylalkyl, or are combined together to form a 3-7 membered ring;

$R^3$ is selected from a group consisting of hydrogen and alkyl;

Ring-B is selected from a group consisting of thiazolyl and benzothiazolyl; with a proviso that the amide nitrogen of formula-(I) is not connected through any heteroatom of ring-B;

$R^4$ and $R^5$ are independently selected from a group consisting of halogen, alkyl, —$(CR^8R^9)_n(CO)OR^6$, —(CR$^8$ R⁹)ₙ(CO)NR⁶R⁷, —(CR⁸R⁹)ₙS(O)ₚNR⁶R⁷, —(CR⁸R⁹)ₙN(R⁶)C(O)R⁶, —(CR⁸R⁹)ₙOR⁶, —(CR⁸R⁹)ₙNR⁶R⁷, —(CR⁸R⁹)ₙCO(R⁶), cycloalkyl, cycloalkylalkyl, heterocyclyl, heterocycloalkyl, aryl, arylalkyl, heteroaryl, heteroarylalkyl, tetrazole, and tetrazolylalkyl, which are further optionally substituted with one or more substituents selected from a group consisting of halo, straight chain or branched chain alkyl, alkenyl, alkynyl, cycloalkyl, aryl, heteroaryl, heterocycle, alkylsulphonyl, oxo, nitro, cyano, —COOR⁶, —C(O)NR⁶R⁷, —OR⁶, —SR⁶, and —NR⁶R⁷;

wherein p=0-2; n=0-4; and

R⁶, R⁷, R⁸, and R⁹ are as described above.

2. A compound as claimed in claim 1, wherein the compound is:

2-(4-Chloro-phenoxy)-2-methyl-N-thiazol-2-yl-propionamide;
2-Methyl-2-(4-methylsulfanyl-phenoxy)-N-thiazol-2-yl-propionamide;
2-(6-Chloro-pyridin-2-yloxy)-2-methyl-N-thiazol-2-yl-propionamide;
2-Methyl-2-(naphthalen-1-yloxy)-N-thiazol-2-yl-propionamide;
2-Methyl-2-(naphthalen-2-yloxy)-N-thiazol-2-yl-propionamide;
2-(2,4-Difluoro-phenoxy)-2-methyl-N-thiazol-2-yl-propionamide;
2-Methyl-2-(4-phenoxy-phenoxy)-N-thiazol-2-yl-propionamide;
2-Methyl-N-thiazol-2-yl-2-(4'-trifluoromethoxy-biphenyl-4-yloxy)-propionamide;
2-(Benzo[1,3]dioxol-5-yloxy)-N-(5-chloro-thiazol-2-yl)-2-methyl-propionamide;
N-(5-Chloro-thiazol-2-yl)-2-(2,4-difluoro-phenoxy)-2-methyl-propionamide;
2-(5-Chloro-pyridin-3-yloxy)-N-(5-chloro-thiazol-2-yl)-2-methyl-propionamide;
N-(5-Chloro-thiazol-2-yl)-2-methyl-2-(3-nitro-phenoxy)-propionamide;
2-(2-Chloro-pyridin-3-yloxy)-N-(5-chloro-thiazol-2-yl)-2-methyl-propionamide;
2-(Biphenyl-4-yloxy)-N-(5-chloro-thiazol-2-yl)-2-methyl-propionamide;
N-(5-Chloro-thiazol-2-yl)-2-(indan-5-yloxy)-2-methyl-propionamide;
N-(5-Chloro-thiazol-2-yl)-2-(1H-indol-5-yloxy)-2-methyl-propionamide;
N-(5-Chloro-thiazol-2-yl)-2-(4-methanesulfonyl-phenoxy)-2-methyl-propionamide;
N-(5-Chloro-thiazol-2-yl)-2-(2,4-difluoro-phenoxy)-2,2-difluoro-acetamide;
2-(2,4-Difluoro-phenoxy)-N-(6-fluoro-benzothiazol-2-yl)-2-methyl-propionamide;
2-(2,4-Difluoro-phenoxy)-2-methyl-N-(4-phenyl-thiazol-2-yl)-propionamide;
2-(2,4-Difluoro-phenoxy)-N-(5-fluoro-thiazol-2-yl)-2-methyl-propionamide;
1-(2,4-difluorophenoxy)-N-(5-fluorothiazol-2-yl)cyclobutanecarboxamide;
{5-Chloro-2-[2-(2,4-difluoro-phenoxy)-2-methyl-propionylamino]-thiazol-4-yl}-acetic acid ethyl ester;
{2-[2-Methyl-2-(naphthalen-1-yloxy)-propionylamino]-thiazol-4-yl}-acetic acid;
{2-[2-(5-Chloro-pyridin-2-yloxy)-2-methyl-propionylamino]-thiazol-4-yl}-acetic acid;
{5-Chloro-2-[2-methyl-2-(4-nitro-phenoxy)-propionylamino]-thiazol-4-yl}-acetic acid;
{5-Chloro-2-[2-(2,4-difluoro-phenoxy)-2-methyl-propionylamino]-thiazol-4-yl}-acetic acid;
{5-Chloro-2-[2-(2,6-difluoro-phenoxy)-2-methyl-propionylamino]-thiazol-4-yl}-acetic acid;
{5-Chloro-2-[2-(2,5-difluoro-phenoxy)-2-methyl-propionylamino]-thiazol-4-yl}-acetic acid;
{5-Chloro-2-[2-methyl-2-(3-nitro-phenoxy)-propionylamino]-thiazol-4-yl}-acetic acid;
2-[2-(2,4-Difluoro-phenoxy)-2-methyl-propionylamino]-4-methyl-thiazole-5-carboxylic acid;
(2-{[1-(2,4-Difluoro-phenoxy)-cyclobutanecarbonyl]-amino}-thiazol-4-yl)-acetic acid;
1-(4-Methanesulfonyl-phenoxy)-cyclohexanecarboxylic acid, thiazol-2-yl amide;
(2-{[1-(4-Methanesulfonyl-phenoxy)-cyclohexanecarbonyl]-amino}-thiazol-4-yl)-acetic acid;
2-Methyl-N-thiazol-2-yl-2-(3-trifluoromethyl-phenylamino)-propionamide;
N-(5-Chlorothiazol-2-yl)-2-(2,4-difluorophenylamino)-2-methyl-propionamide;
2-Methyl-N-thiazol-2-yl-2-(4-thiophen-3-yl-phenoxy)-propionamide;
{2-[2-(2,4-Difluoro-phenoxy)-2-methyl-butyrylamino]-thiazol-4-yl}-acetic acid ethyl ester;
2-(4-Chloro-phenoxy)-2,5-dimethyl-hexanoic acid thiazol-2-ylamide;
2-(4-Chloro-phenoxy)-4-(4-fluoro-phenyl)-2-methyl-N-thiazol-2-yl-butyramide;
2-(4-Chloro-phenoxy)-2-methyl-N-thiazol-2-yl-4-thiophen-3-yl-butyramide;
2-(2,4-Difluoro-phenoxy)-2-methyl-N-thiazol-2-yl-4-thiophen-3-yl-butyramide;
N-(5-Chloro-thiazol-2-yl)2-(2,4-difluoro-phenoxy)-2-methyl-4-thiaphen-3-yl-butyl amide;
N-(5-Chloro-thiazol-2-yl)-2-(2,4-difluoro-phenoxy)-2-methyl-butyramide;
2-(2,4-Difluoro-phenoxy)-N-(6-fluoro-benzothiazol-2-yl)-2-methyl-butyramide;
2-(2,4-Difluoro-phenoxy)-N-(5-fluoro-thiazol-2-yl)-2-methyl-butyramide;
2-(2,4-Difluoro-phenoxy)-2-methyl-N-(4-phenyl-thiazol-2-yl)-butyramide;
{2-[2-(2,4-Difluoro-phenoxy)-2-methyl-butyrylamino]-thiazol-4-yl}-acetic acid;
2-(3-Acetylamino-phenoxy)-2-methyl-N-thiazol-2-yl-propionamide;
2-(3-Methanesulfonylamino-phenoxy)-2-methyl-N-thiazol-2-yl-propionamide;
2-Methyl-2-(3-pyrrolidin-1-yl-phenoxy)-N-thiazol-2-yl-propionamide;
2-(3-Acetylamino-phenoxy)-N-(5-chloro-thiazol-2-yl)-2-methyl-propionamide;
N-(5-Chloro-thiazol-2-yl)-2-(4-diethylamino-phenoxy)-2-methyl-propionamide;
2-(4-Isopropylamino-phenoxy)-2-methyl-N-thiazol-2-yl-propionamide;
2-[4-(2,5-Dimethyl-pyrrol-1-yl)-phenoxy]-2-methyl-N-thiazol-2-yl-propionamide;
2-(2,4-Difluoro-phenoxy)-N-{4-[(4-fluoro-phenylcarbamoyl)-methyl]-thiazol-2-yl}-2-methyl-propionamide;
2-(Benzo[1,3]dioxol-5-yloxy)-N-{4-[(4-fluoro-phenylcarbamoyl)-methyl]-thiazol-2-yl}-2-methyl-propionamide;

N-{5-Chloro-4-[(4-fluoro-phenylcarbamoyl)-methyl]-thiazol-2-yl}-2-(2,4-difluoro-phenoxy)-2-methyl-propionamide;
2-(2,4-Difluoro-phenoxy)-N-{4-[(4-fluoro-phenylcarbamoyl)-methyl]-thiazol-2-yl}-2-methyl-butyramide;
2-(5-Chloro-pyridin-3-yloxy)-N-{4-[(4-fluoro-phenylcarbamoyl)-methyl]-thiazol-2-yl}-2-methyl-propionamide;
2-(2,4-Difluoro-phenoxy)-N-{4-[(2,4-difluoro-phenylcarbamoyl)-methyl]-thiazol-2-yl}-2-methyl-propionamide;
2-(2,4-Difluoro-phenoxy)-2-methyl-N-[4-(thiazol-2-ylcarbamoylmethyl)-thiazol-2-yl]-propionamide;
N-{5-Chloro-4-[(4-fluoro-phenylcarbamoyl)-methyl]-thiazol-2-yl}-2-methyl-2-(4-nitro-phenoxy)-propionamide;
N-{4-[(4-Fluoro-phenylcarbamoyl)-methyl]-thiazol-2-yl}-2-(1H-indol-5-yloxy)-2-methyl-propionamide;
2-(2,4-Difluoro-phenoxy)-2-methyl-N-[4-(pyridin-3-ylcarbamoylmethyl)-thiazol-2-yl]-butyramide;
3-[1-Methyl-1-(thiazol-2-ylcarbamoyl)-ethoxy]-benzoic acid;
3-[1-(5-Chloro-thiazol-2-ylcarbamoyl)-1-methyl-ethoxy]-benzoic acid;
4-[1-Methyl-1-(thiazol-2-ylcarbamoyl)-ethoxy]-benzoic acid;
4-[1-(5-Chloro-thiazol-2-ylcarbamoyl)-1-methyl-ethoxy]-benzoic acid;
1-(2,4-Difluoro-phenoxy)-cyclopropanecarboxylic acid, thiazol-2-ylamide;
1-(2,4-Difluoro-phenoxy)-cyclopropanecarboxylic acid, (5-chloro-thiazol-2-yl)-amide;
(5-Chloro-2-[1-(2,4-difluoro-phenoxy)-cyclopropanecarbonyl]-amino-thiazol-4-yl)-acetic acid;
N-(5-Chloro-thiazol-2-yl)-2-methyl-2-{3-[2-(4-trifluoromethyl-phenyl)-ethylamino]-phenoxy}-propionamide;
2-(2,4-Difluoro-phenoxy)-N-{4-[2-(4-fluoro-phenoxy)-ethyl]-thiazol-2-yl}-2-methyl-propionamide;
2-(3,4-Dichloro-phenoxy)-N-{4-[2-(4-fluoro-phenoxy)-ethyl]-thiazol-2-yl}-2-methyl-propionamide;
N-(5-Chloro-thiazol-2-yl)-2-(2-cyclopentylmethoxy-phenoxy)-2-methyl-propionamide;
2-[4-Chloro-3-(2-thiophen-3-yl-ethoxy)-phenoxy]-2-methyl-N-thiazol-2-yl-propionamide;
2-[2-Chloro-5-(2-thiophen-3-yl-ethoxy)-phenoxy]-2-methyl-N-thiazol-2-yl-propionamide;
2-(2,4-Difluoro-phenoxy)-2-(4-methanesulfonyl-phenyl)-N-thiazol-2-yl-propionamide;
2-(4-Methanesulfonyl-phenyl)-N-thiazol-2-yl-2-(5-trifluoromethoxy-pyridin-2-yloxy)-propionamide;
2-(2,4-Difluoro-phenoxy)-2-(4-methanesulfonyl-phenyl)-N-thiazol-2-yl-propionamide;
N-(5-Chloro-thiazol-2-yl)-2-(4-methanesulfonyl-phenyl)-2-(4-methylsulfanyl-phenoxy)-propionamide;
2-(Biphenyl-4-yloxy)-2-(4-methanesulfonyl-phenyl)-N-thiazol-2-yl-propionamide;
2-(Benzo[1,3]dioxol-5-yloxy)-N-(5-fluoro-thiazol-2-yl)-2-(4-methanesulfonyl-phenyl)-propionamide;
2-(Benzo[1,3]dioxol-5-yloxy)-2-(4-methanesulfonyl-phenyl)-N-(4-phenyl-thiazol-2-yl)-propionamide;
N-Benzothiazol-2-yl-2-(2,4-difluorophenoxy)-2-(4-methanesulfonyl-phenyl)-propionamide;
2-(2,4-Difluoro-phenoxy)-N-(5-fluoro-thiazol-2-yl)-2-(4-methanesulfonyl-phenyl)-propionamide;
2-(Benzo[1,3]dioxol-5-yloxy)-N-(5-chloro-thiazol-2-yl)-2-(4-trifluoromethyl-phenyl)-propionamide;
2-(1H-Indol-5-yloxy)-2-(4-methanesulfonyl-phenyl)-N-thiazol-2-yl-propionamide;
2-(2,4-Difluoro-phenoxy)-N-{4-[2-(4-fluoro-phenoxy)-ethyl]-thiazol-2-yl}-2-(4-methanesulfonyl-phenyl)-propionamide;
N-(5-Chloro-thiazol-2-yl)-2-(4-cyclopropanesulfonyl-phenyl)-2-(2,4-difluoro-phenoxy)-propionamide;
2-(2,4-Difluoro-phenoxy)-2-(4-methanesulfonyl-phenyl)-N-(5-methyl-thiazol-2-yl)-propionamide;
2-(2,4-Difluoro-phenylamino)-2-(4-methanesulfonyl-phenyl)-N-thiazol-2-yl-propionamide;
{5-Chloro-2-[2-(2,4-difluoro-phenoxy)-2-(4-methanesulfonyl-phenyl)-propionylamino]-thiazol-4-yl}-acetic acid;
{5-Chloro-2-[2-(4-fluoro-phenoxy)-2-(4-methanesulfonyl-phenyl)-propionylamino]-thiazol-4-yl}-acetic acid;
2-methyl-N-(thiazol-2-yl)-2-(benzothiophen-5-yloxy) propionamide;
N-(5-Chloro-thiazol-2-yl)-2-methyl-2-[2-(2-thiophen-2-yl-ethoxy)-phenoxy]-propionamide;
2-(1H-Indol-5-yloxy)-2-methyl-N-thiazol-2-yl-propionamide;
2-(Biphenyl-4-yloxy)-2-methyl-N-thiazol-2-yl-propionamide;
2-(Indan-5-yloxy)-2-methyl-N-thiazol-2-yl-propionamide;
{2-[2-(Benzo[1,3]dioxol-5-yloxy)-2-methyl-propionylamino]-thiazol-4-yl}-acetic acid;
{2-[2-(2,4-Difluoro-phenoxy)-2-methyl-propionylamino]-thiazol-4-yl}-acetic acid;
2-[2-(2,4-Difluoro-phenoxy)-2-methyl-propionylamino]-thiazole-4-carboxylic acid;
2-[2-(Benzo[1,3]dioxol-5-yloxy)-2-methyl-propionylamino]-5-chloro-thiazole-4-carboxylic acid;
2-[2-(Benzo[1,3]dioxol-5-yloxy)-2-methyl-propionylamino]-thiazole-4-carboxylic acid;
5-Chloro-2-[2-(2,4-difluoro-phenoxy)-2-methyl-propionylamino]-thiazole-4-carboxylic acid;
{2-[2-(Benzo[1,3]dioxol-5-yloxy)-2-methyl-propionylamino]-5-chloro-thiazol-4-yl}-acetic acid;
{2-[2-Methyl-2-(naphthalen-2-yloxy)-propionylamino]-thiazol-4-yl}-acetic acid;
{5-Chloro-2-[2-(4-chloro-phenoxy)-2-methyl-propionylamino]-thiazol-4-yl}-acetic acid;
{5-Chloro-2-[2-(3,4-difluoro-phenoxy)-2-methyl-propionylamino]-thiazol-4-yl}-acetic acid;
{2-[2-(4-Methanesulfonyl-phenoxy)-2-methyl-propionylamino]-thiazol-4-yl}-acetic acid;
{2-[2-(4-tert-Butyl-phenoxy)-2-methyl-propionylamino]-5-chloro-thiazol-4-yl}-acetic acid;
2-{[1-(4-Methanesulfonyl-phenoxy)-cyclohexanecarbonyl]-amino}-thiazole-4-carboxylic acid;
2-(4-Chloro-phenoxy)-N-(5-chloro-thiazol-2-yl)-2-methyl-4-thiophen-2-yl-butyramide;
{2-[2-(4-Chloro-phenoxy)-3-cyclopentyl-2-methyl-propionylamino]-thiazol-4-yl}-acetic acid;
3-{5-Chloro-2-[2-(2,4-difluoro-phenoxy)-2-methyl-propionylamino]-thiazol-4-yl}-propionic acid;
{2-[2-(4-Acetylamino-phenoxy)-2-methyl-propionylamino]-5-chloro-thiazol-4-yl}-acetic acid;
2-Methyl-N-thiazol-2-yl-2-[4-(2-thiophen-2-yl-ethylamino)-phenoxy]-propionamide;
N-(5-Chloro-thiazol-2-yl)-2-methyl-2-{4-[2-(4-trifluoromethyl-phenyl)-ethylamino]-phenoxy}-propionamide;
2-[2-(2,4-Difluoro-phenoxy)-2-methyl-propionylamino]-thiazole-4-carboxylic acid (4-fluoro-phenyl)-amide;

2-(Benzo[1,3]dioxol-5-yloxy)-N-{5-chloro-4-[(4-fluoro-phenylcarbamoyl)-methyl]-thiazol-2-yl}-2-methyl-propionamide;

N-{4-[(2,4-Difluoro-phenylcarbamoyl)-methyl]-thiazol-2-yl}-2-(1H-indol-5-yloxy)-2-methyl-propionamide;

{4-[1-(5-Chloro-thiazol-2-ylcarbamoyl)-1-methyl-ethoxy]-3-fluoro-phenyl}-acetic acid;

2-(Benzo[1,3]dioxol-5-yloxy)-N-{4-[2-(4-fluoro-phenoxy)-ethyl]-thiazol-2-yl}-2-methyl-propionamide;

2-(2,4-Difluoro-phenoxy)-2-(4-methanesulfonyl-phenyl)-N-(4-phenyl-thiazol-2-yl)-propionamide;

2-(2,4-Difluoro-phenoxy)-N-(6-fluoro-benzothiazol-2-yl)-2-(4-methanesulfonyl-phenyl)-propionamide;

N-(4-Chloro-benzothiazol-2-yl)-2-(2,4-difluoro-phenoxy)-2-(4-methanesulfonyl-phenyl)-propionamide;

N-(6-Chloro-benzothiazol-2-yl)-2-(2,4-difluoro-phenoxy)-2-(4-methanesulfonyl-phenyl)-propionamide;

2-(4-(tetrahydropyran-4-ylsulfonyl)phenyl)-2-(2,4-difluoro-phenoxy)-N-(5-fluoro-thiazol-2-yl)-propionamide;

2-[3-Chloro-4-((cyclopentanon-3-yl)sulfonyl-phenyl)-2-(2,4-difluoro-phenoxy)-N-(5-fluoro-thiazol-2-yl]-propionamide;

2-[2-(2,4-Difluoro-phenoxy)-2-(4-methanesulfonyl-phenyl)-propionylamino]-4-methyl-thiazole-5-carboxylic acid;

3-{2-[2-(2,4-Difluoro-phenoxy)-2-(4-methanesulfonyl-phenyl)-propionylamino]-thiazol-4-yl}-propionic acid;

3-{2-[2-(2,4-Difluoro-phenoxy)-2-methyl-propionylamino]-thiazol-4-yl}-propionic acid;

{2-[2-(6-Chloro-pyridin-3-yloxy)-2-(4-methanesulfonyl-phenyl)-propionylamino]-5-fluoro-thiazol-4-yl}-acetic acid;

{2-[2-(4-Cyclopentanesulfonyl-phenyl)-2-(2,4-difluoro-phenoxy)-propionylamino]-5-fluoro-thiazol-4-yl}-acetic acid;

{2-[2-(6-Chloro-pyridin-3-yloxy)-2-(4-cyclopropane-sulfonyl-phenyl)-propionylamino]-5-fluoro-thiazol-4-yl}-acetic acid;

{2-[2-(4-Cyclohexanesulfonyl-phenyl)-2-(2,4-difluoro-phenoxy)-propionylamino]-5-fluoro-thiazol-4-yl}-acetic acid;

2-(4-Chloro-phenoxy)-N-(5-chloro-thiazol-2-yl)-2-(4-methanesulfonyl-phenyl)-propionamide;

N-(5-Chloro-thiazol-2-yl)-2-(2,4-difluorophenoxy)-2-(4-methanesulfonyl-phenyl)-propionamide; or N-(5-Chloro-thiazol-2-yl)-2-(3,4-difluoro-phenoxy)-2-(4-methanesulfonyl-phenyl)-propionamide;

or a stereoisomer thereof, or a pharmaceutically acceptable salt thereof.

3. A method for the treatment of a disease through Glucokinase activation, the method comprising administering an effective amount of a pharmaceutical composition comprising, as an active ingredient, at least one compound having a structure according to formula (I), as claimed in claim 1 or claim 2, or its stereoisomer, or a pharmaceutically acceptable salt thereof, and at least one pharmaceutically acceptable carrier or excipient, wherein the disease is one or more of hyperglycemia, diabetes, impaired glucose tolerance, dyslipidemia or obesity.

4. A method for the therapeutic treatment of hyperglycemia or type II diabetes, the method comprising administering an effective amount of a pharmaceutical composition comprising, as an active ingredient, at least one compound having a structure according to formula (I), as claimed in claim 1 or claim 2, or its stereoisomer or a pharmaceutically acceptable salt thereof, and at least one pharmaceutically acceptable carrier or excipient.

5. A method for the treatment of type II diabetes in a human demonstrating pre-diabetic hyperglycemia or impaired glucose tolerance, the method comprising administering an effective amount of a pharmaceutical composition comprising, as an active ingredient, at least one compound having a structure according to formula (I), as claimed in claim 1 or claim 2, or its stereoisomer, or a pharmaceutically acceptable salt thereof, and at least one pharmaceutically acceptable carrier or excipient.

6. A method for the combined treatment of diabetes and obesity, the method comprising administering an effective amount of a pharmaceutical composition comprising, as an active ingredient, at least one compound having a structure according to formula (I), as claimed in claim 1 or claim 2, or its stereoisomer, or a pharmaceutically acceptable salt thereof, and at least one pharmaceutically acceptable carrier or excipient.

7. A method for the treatment of obesity, the method comprising administering an effective amount of a pharmaceutical composition comprising, as an active ingredient, at least one compound having a structure according to formula (I), as claimed in claim 1 or claim 2, or its stereoisomer, or a pharmaceutically acceptable salt thereof, and at least one pharmaceutically acceptable carrier or excipient.

8. A method for the treatment of dyslipidemia, the method comprising administering an effective amount of a pharmaceutical composition comprising, as an active ingredient, at least one compound having a structure according to formula (I), as claimed in claim 1 or claim 2, or its stereoisomer, or a pharmaceutically acceptable salt thereof, and at least one pharmaceutically acceptable carrier or excipient.

9. A method of therapeutic treatment of Glucokinase activator mediated diseases by administering an effective amount of a compound of formula (I), as claimed in claim 1 or claim 2, or its polymorph, stereoisomer, prodrug, solvate or a pharmaceutically acceptable salt thereof, to a mammal in need of such treatment.

10. A method of combined treatment of diabetes and obesity by administering an effective amount of a compound of formula (I), as claimed in claim 1 or claim 2, or its polymorph, stereoisomer, prodrug, solvate or a pharmaceutically acceptable salt thereof, to a mammal in need of such treatment.

11. A method of treatment of obesity by administering an effective amount of a compound of formula (I), as claimed in claim 1 or claim 2, or its polymorph, stereoisomer, prodrug, solvate or a pharmaceutically acceptable salt thereof, to a mammal in need of such treatment.

12. A method for the treatment of hyperglycemia, IGT, Syndrome X, type 2 diabetes, type 1 diabetes, dyslipidemia, hyperlipidemia, hypertension, obesity, or for lowering of food intake, for appetite regulation, for regulating feeding behaviour, or for enhancing the secretion of GLP-1 enterioncretins, the method comprising administering an effective amount of a pharmaceutical composition comprising, as an active ingredient, at least one compound having a structure according to formula (I), as claimed in claim 1 or claim 5, or its stereoisomer, or a pharmaceutically acceptable salt thereof, and at least one pharmaceutically acceptable carrier or excipient.

13. A pharmaceutical composition comprising, as an active ingredient, at least one compound of formula (I), as claimed in claim 1 or claim 2, or its stereoisomer, or a pharmaceutically acceptable salt thereof, together with one or more pharmaceutically acceptable carriers or excipients.

14. A pharmaceutical composition comprising, as an active ingredient, at least one compound of formula (I), as claimed in claim 1 or claim 2, or its stereoisomer, or a pharmaceutically acceptable salt thereof, together with one or more pharmaceutically acceptable therapeutically active agents.

15. A process for the preparation of a compound of formula (I) as claimed in claim 1 or claim 2 or its polymorph, stereoisomer, prodrug, or a solvate thereof, said process comprising:

reacting an acid of formula (II) or activated derivative thereof,

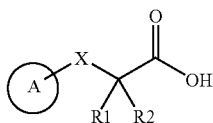

II with a compound of formula (III) or activated derivative thereof,

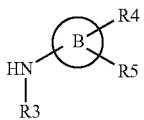

III in presence of a suitable amide coupling reagent, optionally hydrolysing and optionally further coupling with an amine of formula (VII), to obtain the compound of formula (I);

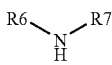

VII wherein ring A, X, R¹, R², ring B, R³, R⁴, R⁵, R⁶, R⁷, R⁸ and R⁹ are as defined above.

16. A process for the preparation of a compound of formula (I) as claimed in claim 1 or claim 2 or its polymorph, stereoisomer, prodrug or solvate thereof, said process comprising:

reacting a substituted ketone of formula

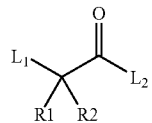

with a compound of formula (III) or activated derivative thereof,

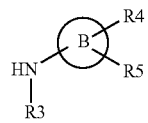

III in presence of a suitable organic acid or inorganic bases and a suitable solvent, to obtain a compound of formula (IV);

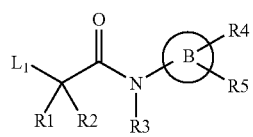

IV further reacting compound of formula (IV) with a nucleophile of formula

optionally hydrolysing and optionally further coupling with an amine of formula (VII), to obtain the compound of formula (I);

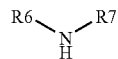

VII wherein A, X, R¹, R², B, R³, R⁴, R⁵, R⁶, R⁷, R⁸ and R⁹ are as defined above, L₁ and L₂ are suitable leaving groups selected from the group consisting of chloro, bromo, iodo, methane sulfonyl and trifluoromethane sulfonyl.

* * * * *